United States Patent
Steinmetz et al.

(10) Patent No.: US 12,156,947 B2
(45) Date of Patent: *Dec. 3, 2024

(54) MELT PROCESSED VIRAL NANOPARTICLE CONSTRUCTS

(71) Applicant: CASE WESTERN RESERVE UNIVERSITY, Cleveland, OH (US)

(72) Inventors: Nicole F. Steinmetz, San Diego, CA (US); Jonathan Pokorski, San Diego, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,828

(22) Filed: May 23, 2023

(65) Prior Publication Data

US 2024/0091165 A1    Mar. 21, 2024

Related U.S. Application Data

(63) Continuation of application No. 16/347,503, filed as application No. PCT/US2017/059935 on Nov. 3, 2017, now Pat. No. 11,654,117.

(60) Provisional application No. 62/417,000, filed on Nov. 3, 2016.

(51) Int. Cl.
| | |
|---|---|
| *A61K 9/51* | (2006.01) |
| *A61K 9/00* | (2006.01) |
| *A61K 39/00* | (2006.01) |
| *C12N 7/00* | (2006.01) |

(52) U.S. Cl.
CPC .......... *A61K 9/5184* (2013.01); *A61K 9/0021* (2013.01); *A61K 9/5153* (2013.01); *C12N 7/00* (2013.01); *A61K 2039/5258* (2013.01); *C12N 2770/18071* (2013.01)

(58) Field of Classification Search
CPC .. A61K 9/5184; A61K 9/0021; A61K 9/5153; A61K 2039/5258; A61K 2039/812; A61K 39/001106; A61K 2039/545; A61K 2039/55555; A61K 2039/585; A61K 2039/892; A61K 39/39; A61K 39/12; A61K 9/0019; C12N 7/00; C12N 2770/18071; C12N 2770/00023; C12N 2770/00034; C12N 2770/18023; C12N 2770/18034; C12N 2795/00023; C12N 2795/00034; A61P 31/14; B82Y 5/00; C07K 14/005
See application file for complete search history.

(56) References Cited

U.S. PATENT DOCUMENTS

| | | | |
|---|---|---|---|
| 2005/0019270 A1 | 1/2005 | Finlay et al. | |
| 2007/0248617 A1 | 10/2007 | Bachmann et al. | |
| 2007/0258889 A1 | 11/2007 | Douglas et al. | |
| 2007/0284545 A1 | 12/2007 | Isacsson et al. | |
| 2015/0033418 A1 | 1/2015 | Lommel et al. | |
| 2015/0265696 A1* | 9/2015 | Gourapura | A61K 35/76 424/501 |
| 2020/0179468 A1 | 6/2020 | Steinmetz | |

FOREIGN PATENT DOCUMENTS

| | | |
|---|---|---|
| JP | 2009524699 A | 7/2009 |
| WO | 200118199 A1 | 3/2001 |
| WO | 2001/0026682 A2 | 4/2001 |
| WO | 2003092623 A2 | 11/2003 |
| WO | 2012078069 A1 | 6/2012 |
| WO | 2013181557 A1 | 12/2013 |
| WO | 2014/059021 A1 | 4/2014 |
| WO | 2015/0039255 A1 | 3/2015 |
| WO | 2015/188110 A1 | 12/2015 |
| WO | WO-2016019393 A1 * | 2/2016 ........ B01L 3/502746 |
| WO | 2016073972 A1 | 5/2016 |
| WO | 2016/149264 A1 | 9/2016 |
| WO | 2017/004123 A1 | 1/2017 |

OTHER PUBLICATIONS

Lee et al. ("PEGylation to Improve Protein Stability During Melt Processing", Macromol Biosci. Oct. 2015;15(10):1332-7) (Year: 2015).*
Yildiz et al. ("Applications of viral nanoparticles in medicine") (Year: 2011).*
Canadian Application No. 3,042,695, Office Action dated Feb. 22, 2024.
"CWRU researcher to turn plant virus shells against human cancers", The Daily, CWRU Researcher to Turn Plant Virus Shells Against Human Cancers. Case Western Reserve University, Apr. 18, 2016.
Agrawal Arpita et al: "Differential Uptake of Chemically Modified Cowpea Mosaic Virus Nanoparticles in Macrophage Subpopulations Present in Inflammatory and Tumor Microenvironments", BIOMACROMOLECULES, vol. 13, No. 10, Oct. 2012 pp. 3320-3326, XP002780313.
Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Applicant: Case Western Reserve University; "Cancer Immunotherapy Using Virus Particles"; Canadian Office Action, dated Aug. 4, 2020; 3 pgs.
Applicant: Case Western Reserve University; "Cancer Immunotherapy Using Virus Particles"; European Patent Application No. 18764856.3 for Supplementary European Search Report dated Dec. 22, 2020; 8 pgs.

(Continued)

*Primary Examiner* — Robert A Wax
*Assistant Examiner* — Quanglong N Truong
(74) *Attorney, Agent, or Firm* — Tarolli, Sundheim, Covell & Tummino LLP

(57) ABSTRACT

A melt processed viral nanoparticle construct for delivery of virus or virus-like particles to a site of interest includes a degradable polymer matrix and a plurality of virus or virus-like particles encapsulated within the degradable polymer matrix. The nanoparticle construct upon administration to the site of interest providing a sustained release of the virus or virus-like particles and/or nanoparticles upon degradation of the polymer matrix.

20 Claims, 34 Drawing Sheets

Specification includes a Sequence Listing.

(56) References Cited

OTHER PUBLICATIONS

Applicant: Case Western Reserve University; "Cancer Immunotherapy Using Virus Particles"; European Patent Application No. 21201960.8; Extended European Search Report dated Jan. 19, 2022; 11 pgs.
Applicant: Case Western Reserve University; "Plant Virus Particles for Delivery of Antimitotic Agents"; Extended European Search Report; dated Aug. 25, 2020; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Canan Uluog, et al.: "Intermediate dose of methotrexate toxicity in non-Hodgkin lymphoma", General Pharmacology, vol. 32, 1999, pp. 215-218, XP55711259.
Chariou, et al., "Detection and Imaging of Aggressive Cancer Cells Using an Epidermal Growth Factor Receptor (EGFR)—Targeted Filamentous Plant Virus-Based Nanoparticle", Bioconjug Chem. Feb. 18, 2015; 26(2): 262-269.
Chinese Patent Appl. No. 201580063662.6; Chinese Office Action; May 5, 2022; 3 pgs.
Czapar, Anna et al. Tobacco Mosaic Virus Delivery of Phenanthriplatin for Cancer therapy. American Chemical Society. Nano 2016 (10) pp. 4119-4126 (Year: 2016).
European Search Report for Patent Application No. 15857504.3-1111/3215520, dated May 7, 2018.
Francisco, Joseph A., et al.; "CAC 10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
Gonzalez Maria Jet al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.
International Search Report for Application No. PCT/US15/59675 (2016).
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).
Le, Duc et al. Chemical addressability of potoato virus X for its applications in bio/nanotechnology. El Sevier. Journal of Structural Biology 200 (2017). pp. 360-368. (Year: 2017).
Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).
Lee et al. "Biodegradable Viral Nanoparticle/Polymer Implants Prepared via Melt-Processing", ACS Nano ePub Sep. 13, 2017 vol. 11 No. 9 pp. 8777-8780.
Lee et al., "PEGylation to Improve Protein Stability During Melt Processing", Macromol Biosci 1-43, 57-75, Oct. 2015 vol. 15 No. 10 pp. 1332-1337.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Lizotte, et al., "Plant-derived viral-like nanoparticle immunotherapy suppress development of metastatic lung cancer", Journal of Immunology, vol. 194, Issue 1 Supplement, May 2015; 4 pgs.
Nicole F. Steinmetz, U.S. Appl. No. 16/998,210, filed Aug. 7, 2020; Non-Final OA dated Dec. 7, 2022.
Nicole F. Steinmetz; U.S. Appl. No. 16/347,503, filed May 3, 2019; NonFinal Rejection dated Jun. 15, 2022; 36 pgs.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Office action for Chinese Patent Application No. 201580063662.6, dated Mar. 4, 2020.
Office action for European Patent Application No. 15 857 504.3-1111, dated Mar. 18, 2020.
Office action for Japanese Patent Application No. 2017-524349, drafted Jan. 31, 2020; Mailed Feb. 10, 2020; 6 pgs.
Patrick h. Iizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Plchova et al. Expression of Human papillomavirus 16 E7ggg oncoprotein on N- and C-terminus of Potato virus X coat protein in bacterial and plant cells. Protein Expression and Purification 77 (2011); p. 146-152.
Saunders Ket al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Sheen et al., "Stimulating Antitumor Immunity with Nanoparticles", Wiley Interdiscip Rev Nanomed Nanobiotechnol, Oct. 2014, vol. 6, pp. 496-505.
Smyth et al. Treatment of rapidly growing K-BALB and CT26 mouse tumours using Semliki Forest virus and its derived vector. Gene Therapy (2005) 12, 147-159.
Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Wen et al. Design of virus-based nanomaterials for medicine, biotechnology, and energy. Chem. Soc. Rev., 2016, 45, 4074. DOI: 10.1039/c5cs00287g (Year: 2016).
Yildiz, et al., "Applications of viral nanoparticles in medicine", Current Opinion in Biotechnology, vol. 22, Issue 6, (2011); pp. 901-908.
Australian Application No. 2023203281, Examination Report dated May 30, 2024.

* cited by examiner

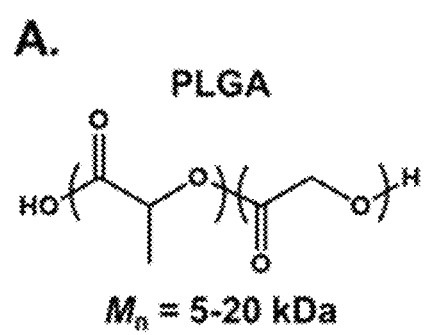
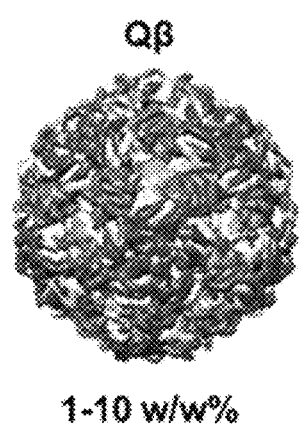
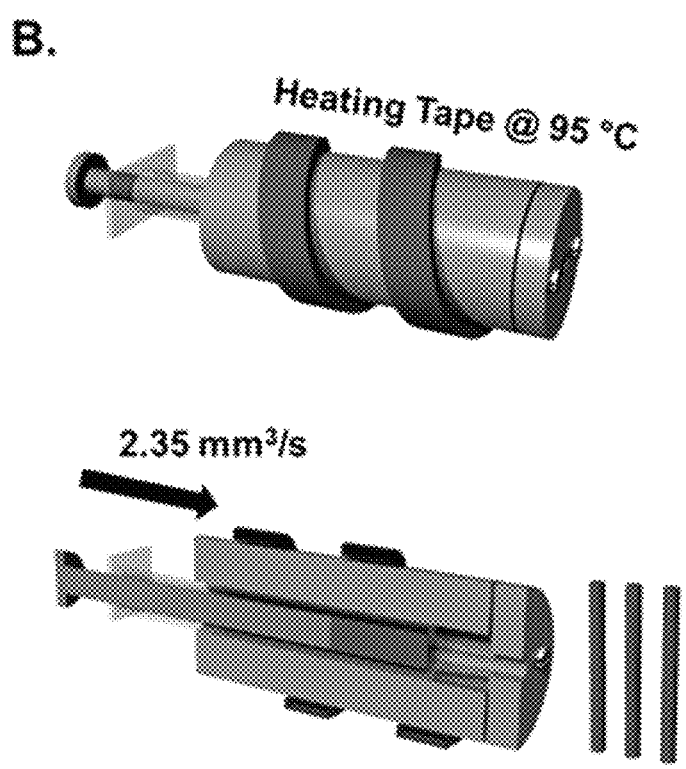
Fig. 1A
Fig. 1B

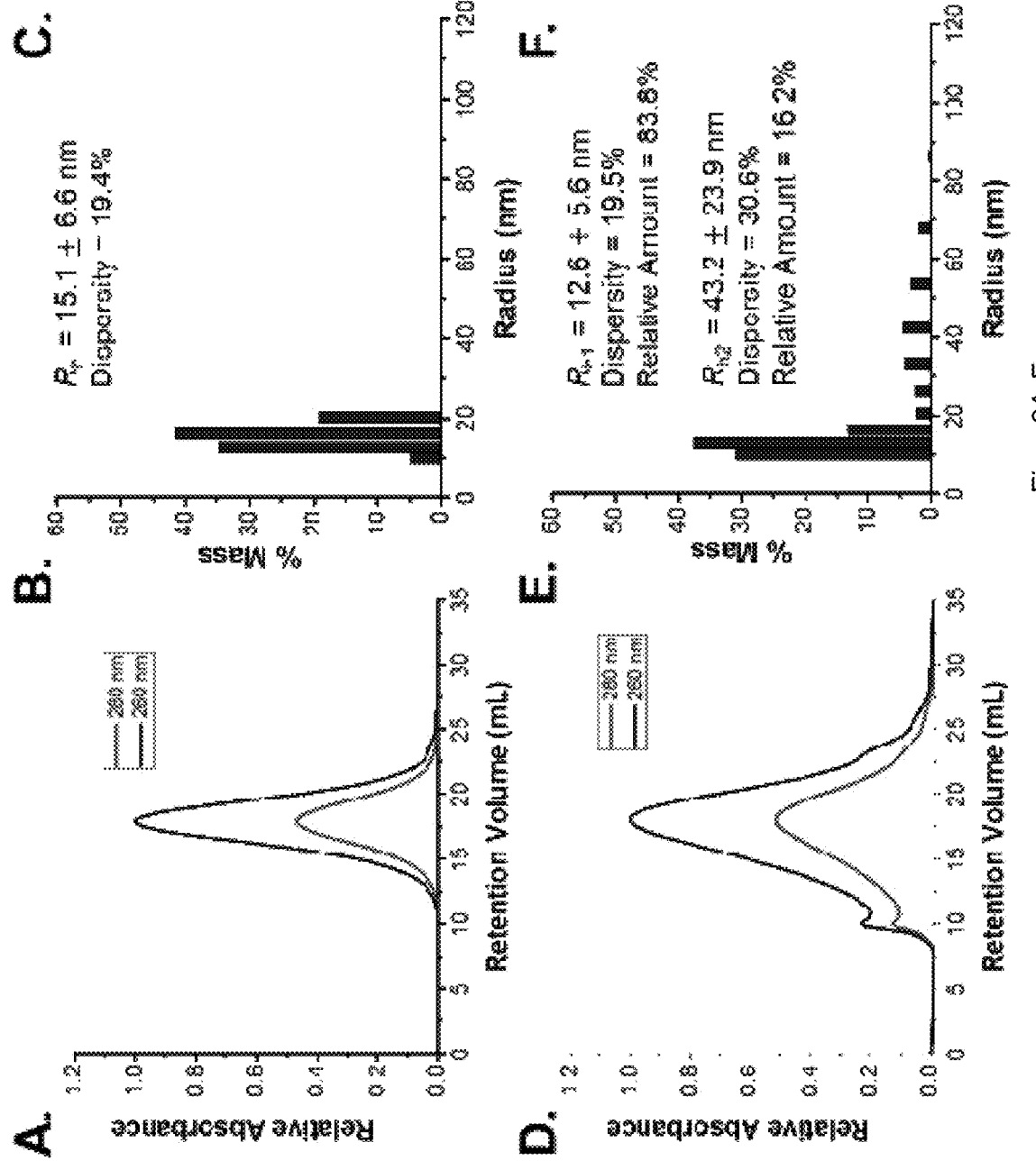
Figs. 2A-F

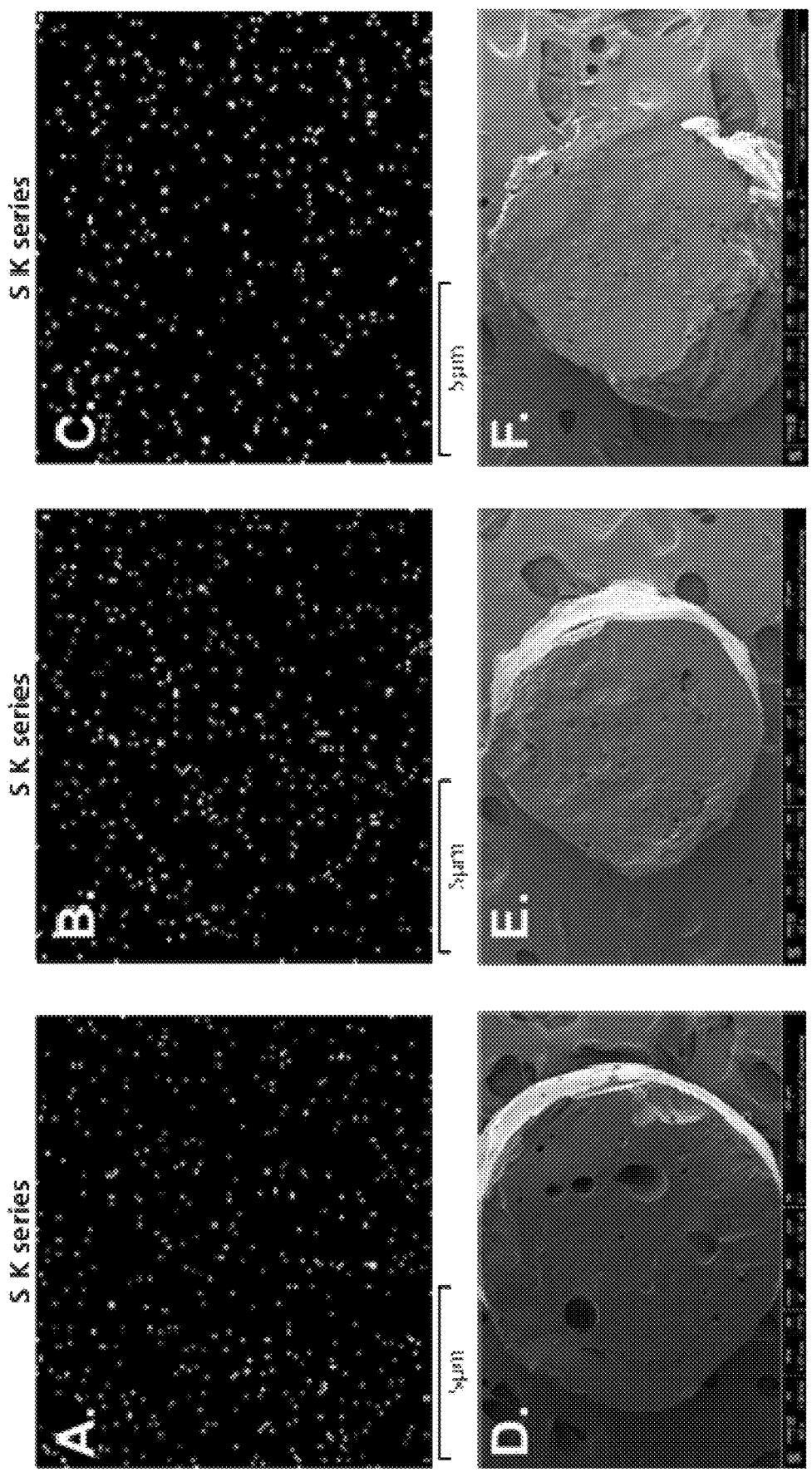
Figs. 3A-F

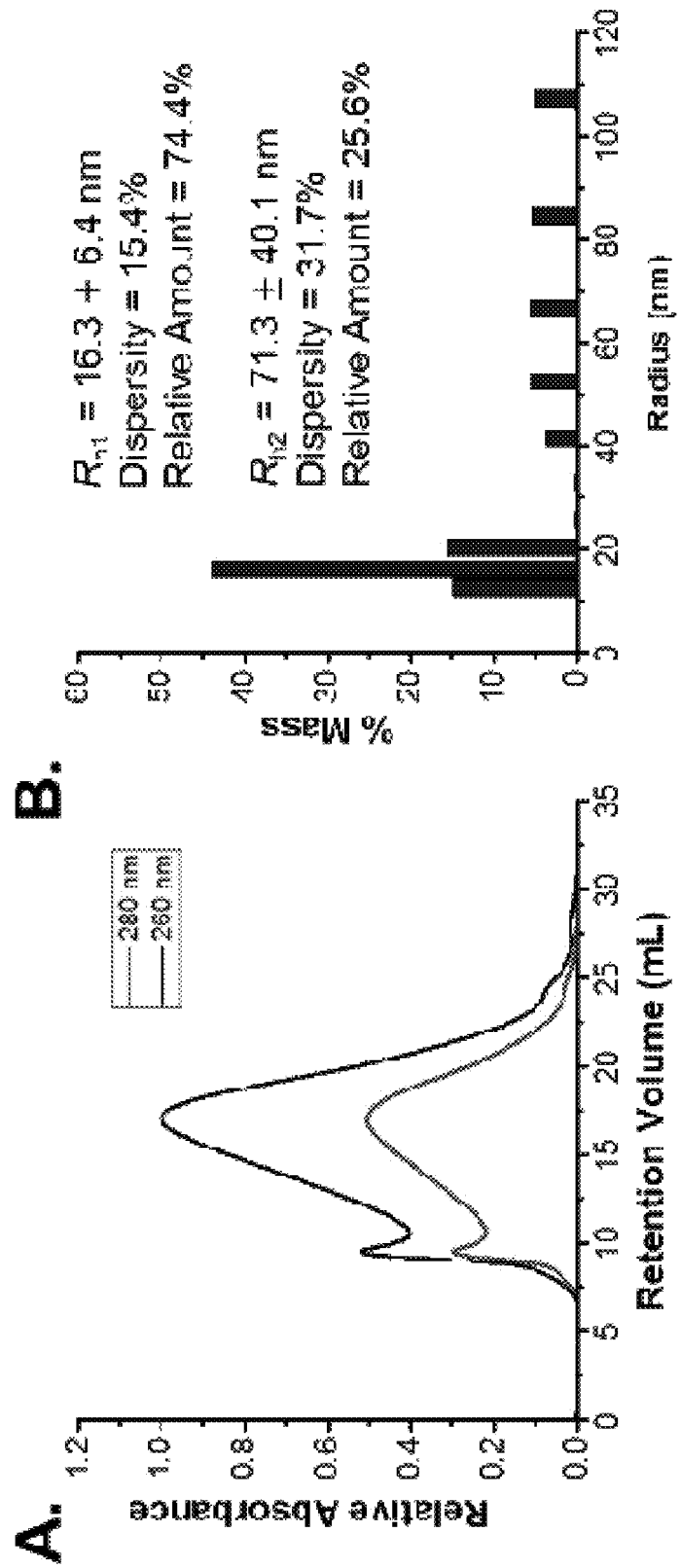
Figs. 4A-B

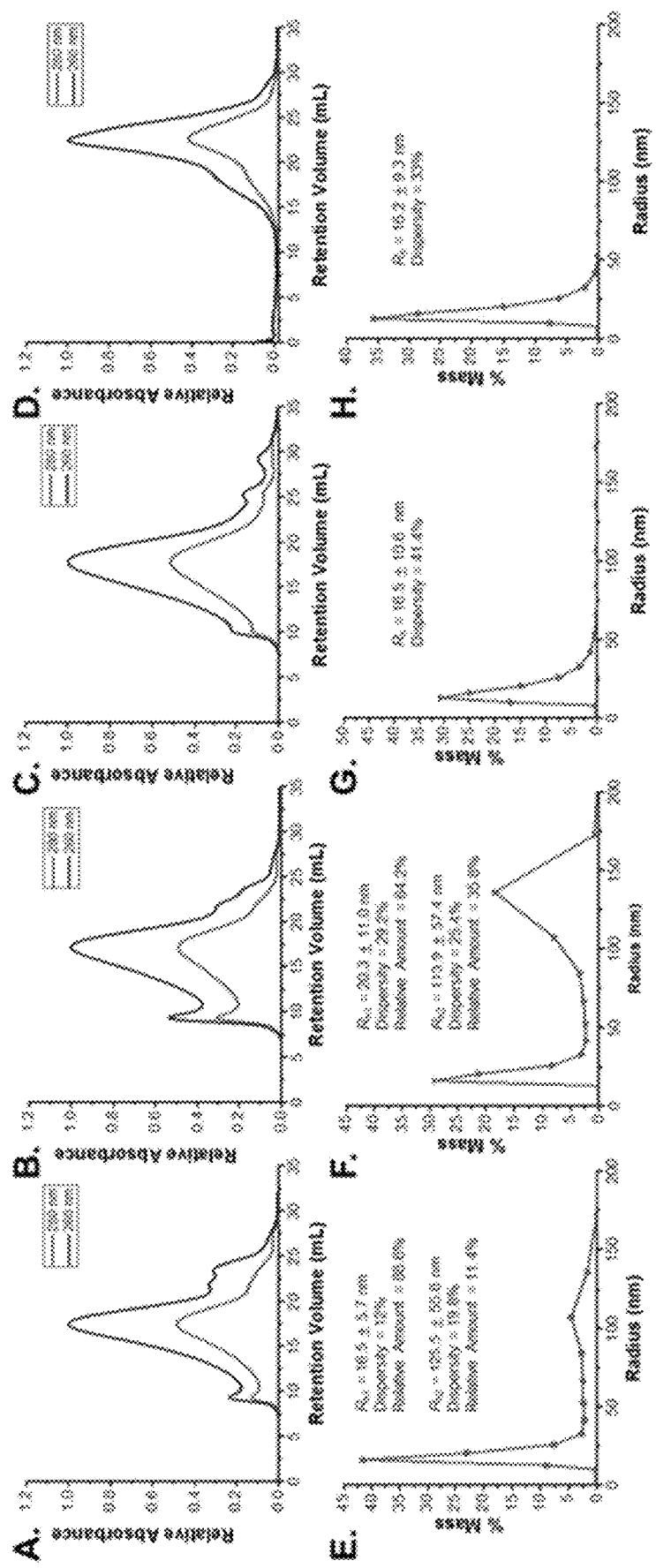
Figs. 5A-H

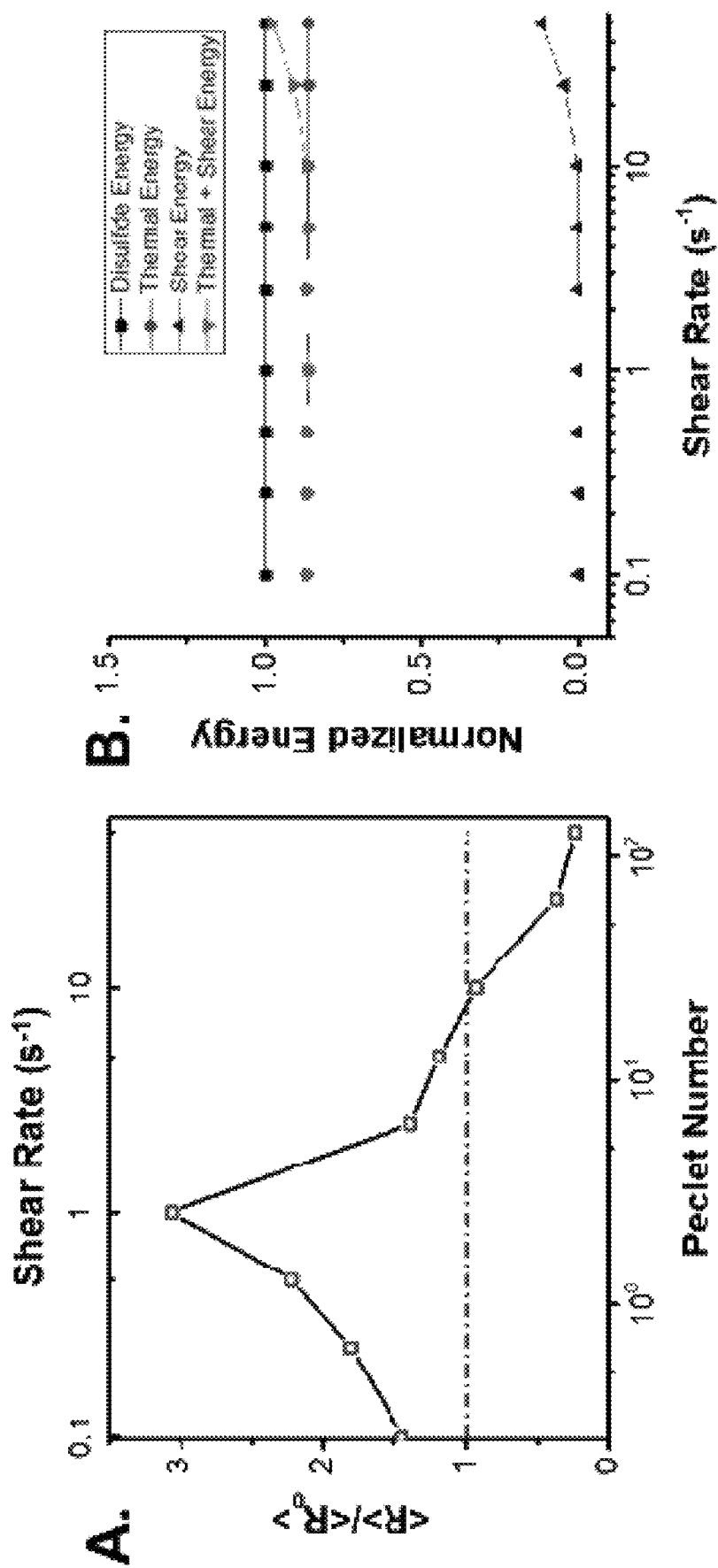
Figs. 6A-B

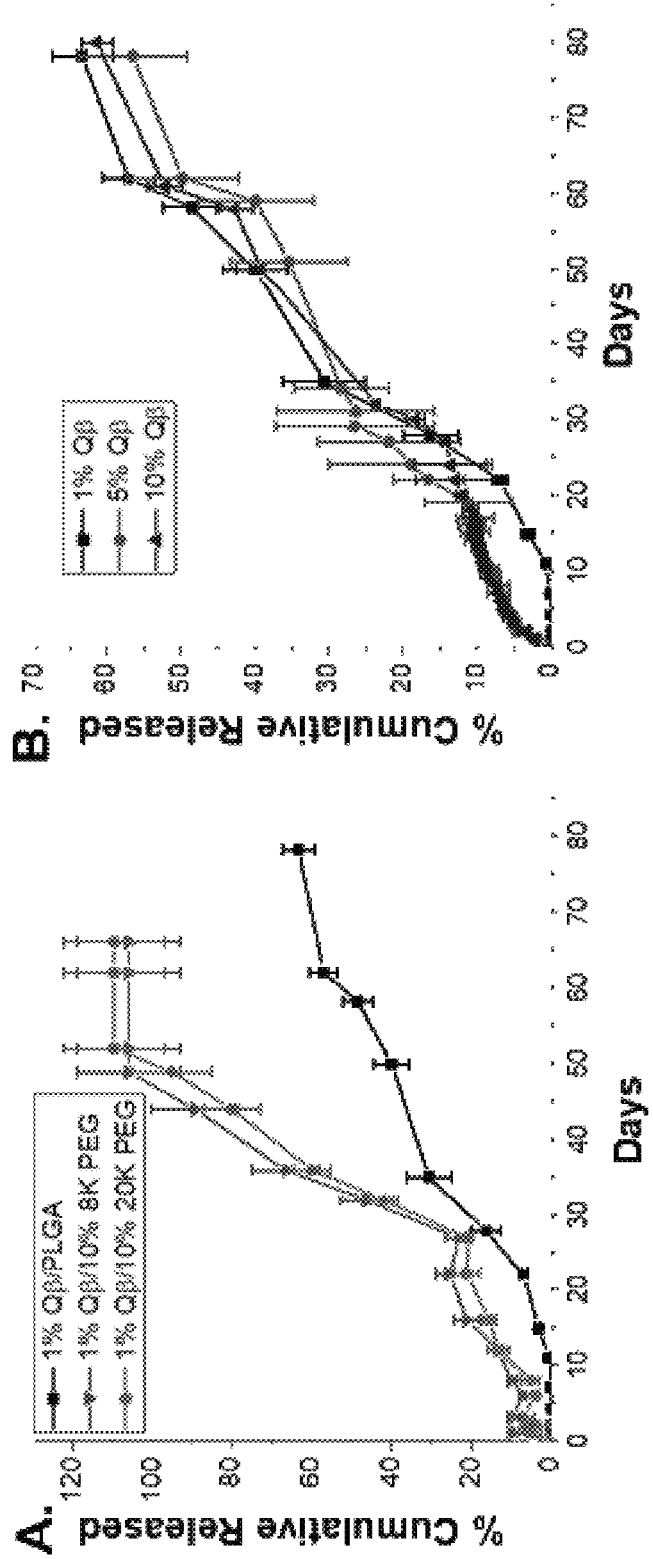
Figs. 7A-B

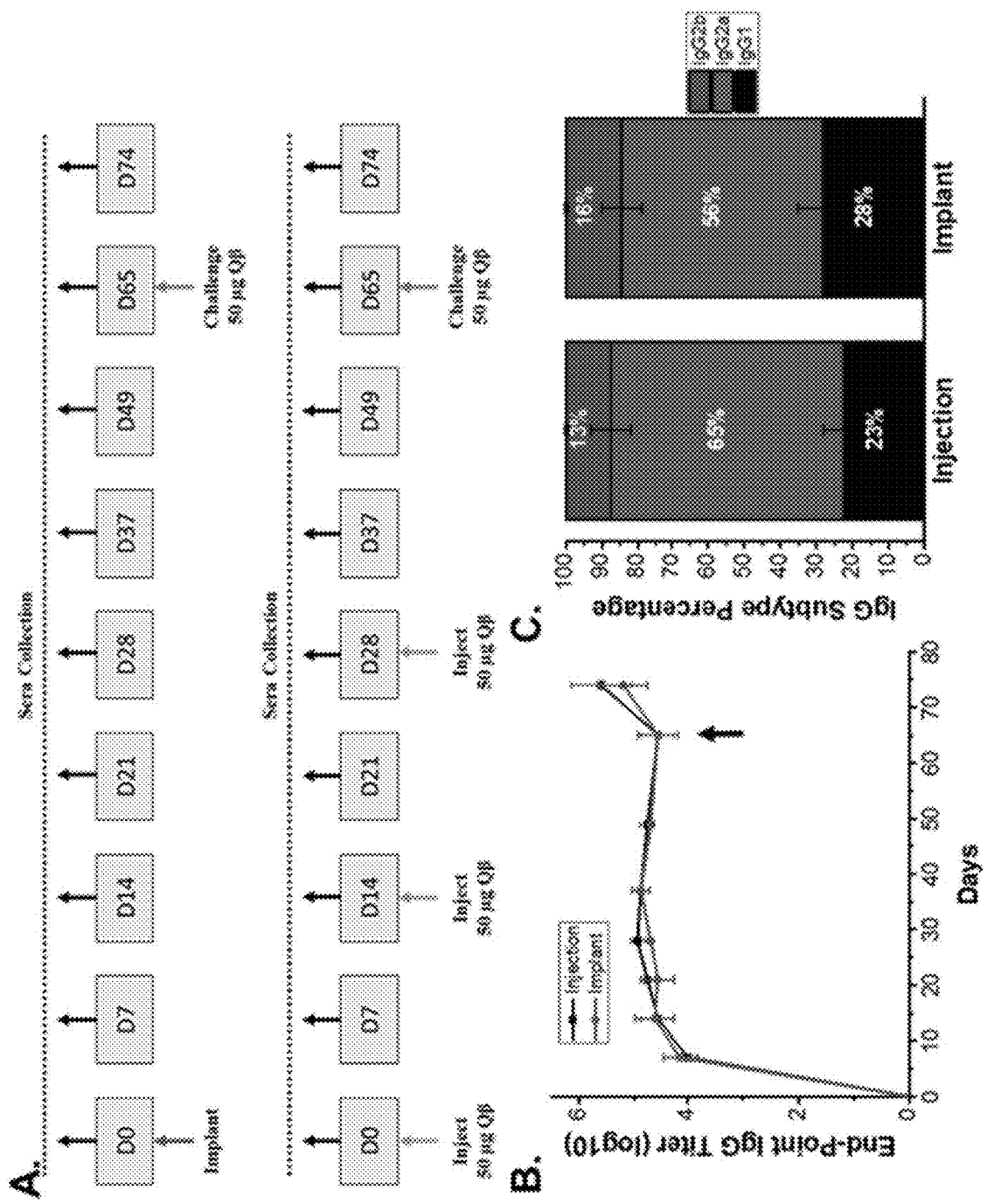
Figs. 8A-C

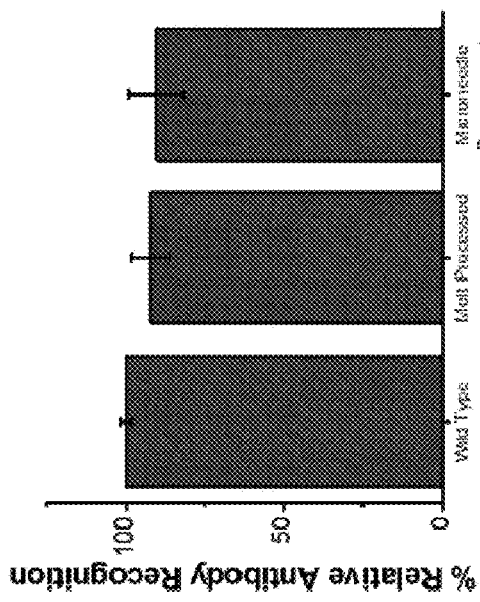
Fig. 11
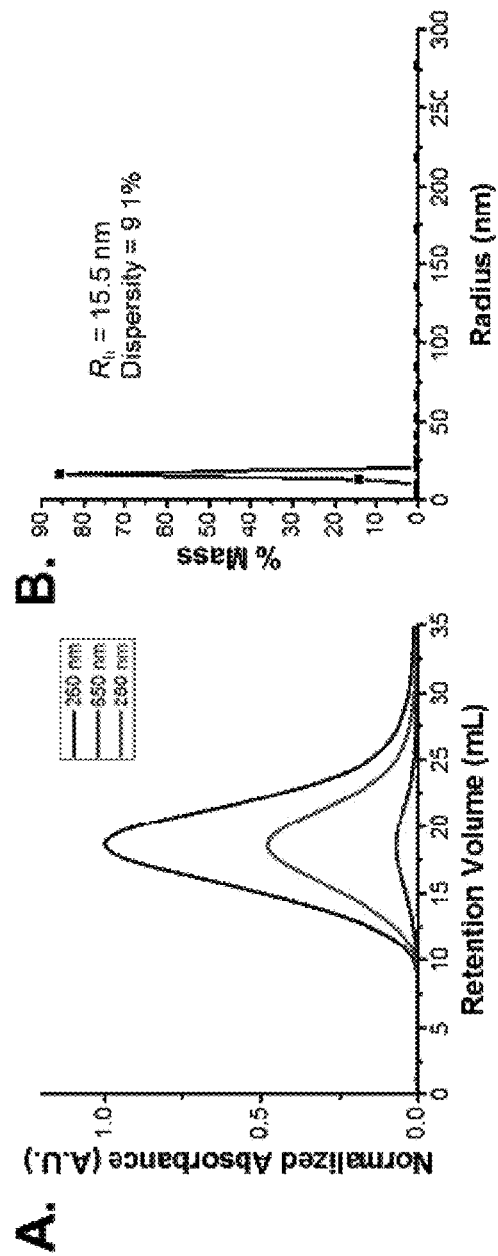
Figs. 12A-B

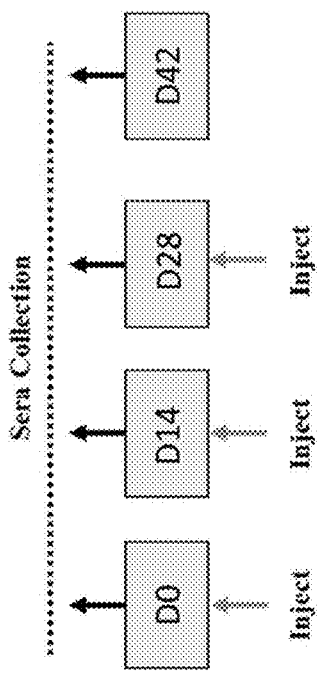
Fig. 17
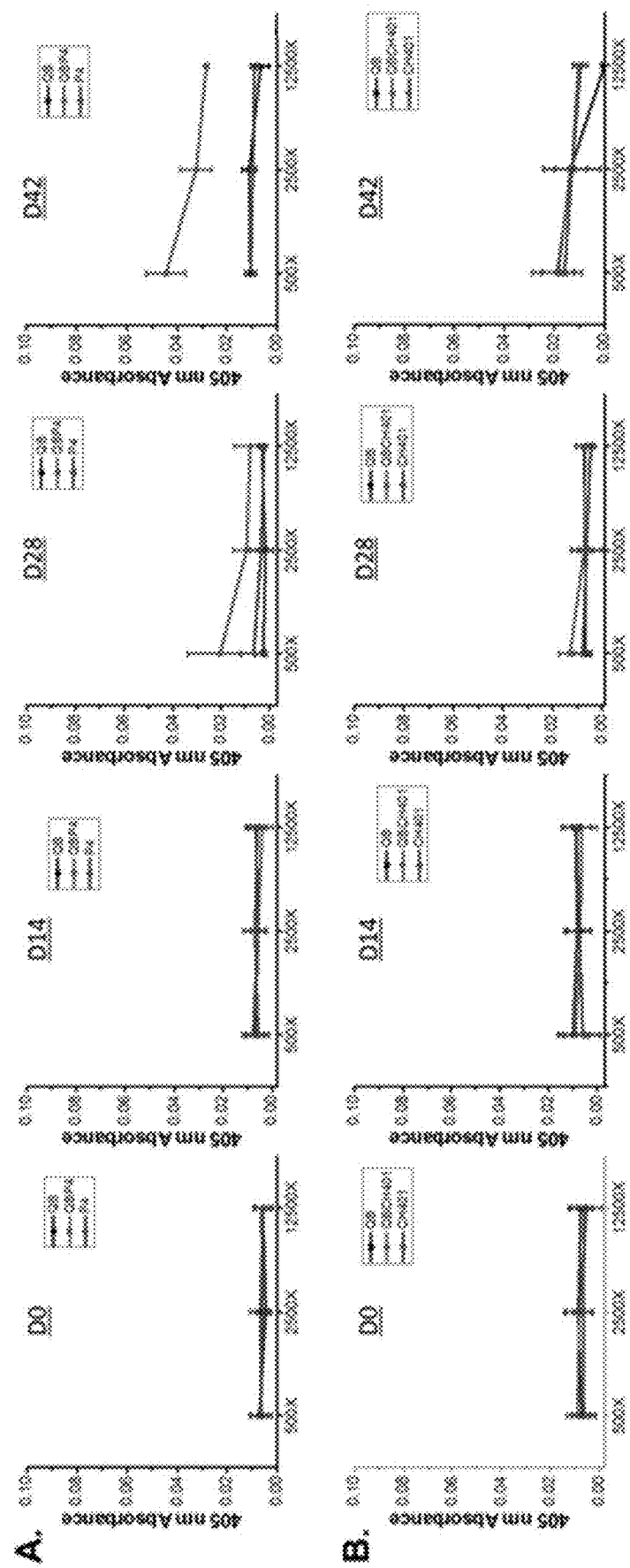
Figs 18A-B

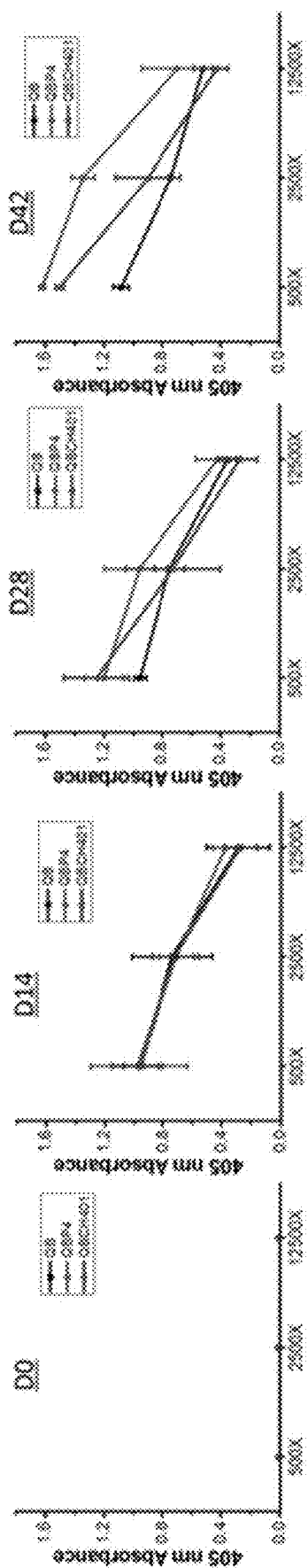
Fig. 19
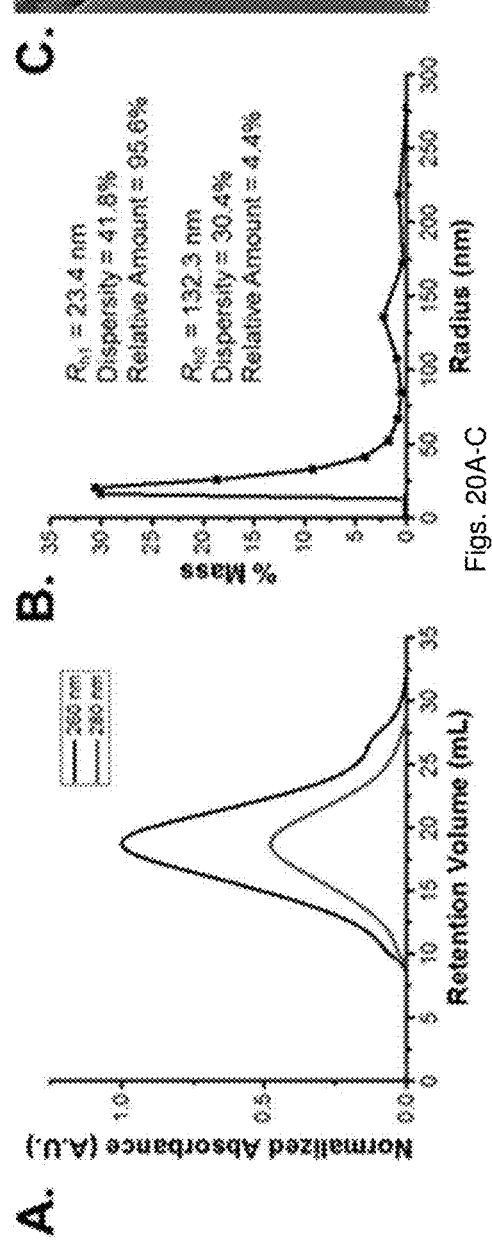
Figs. 20A-C

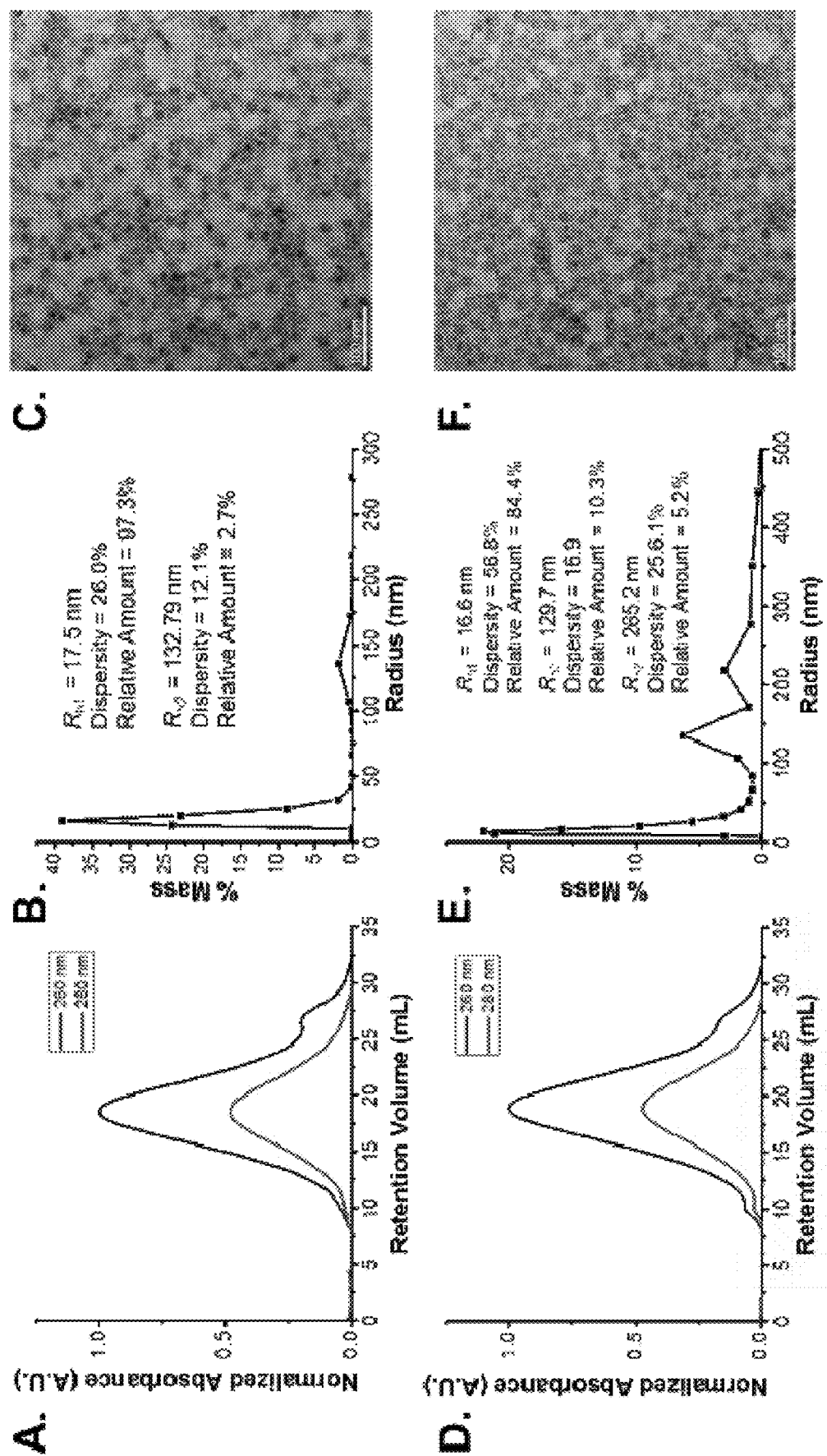
Figs. 21A-F

E.

F.

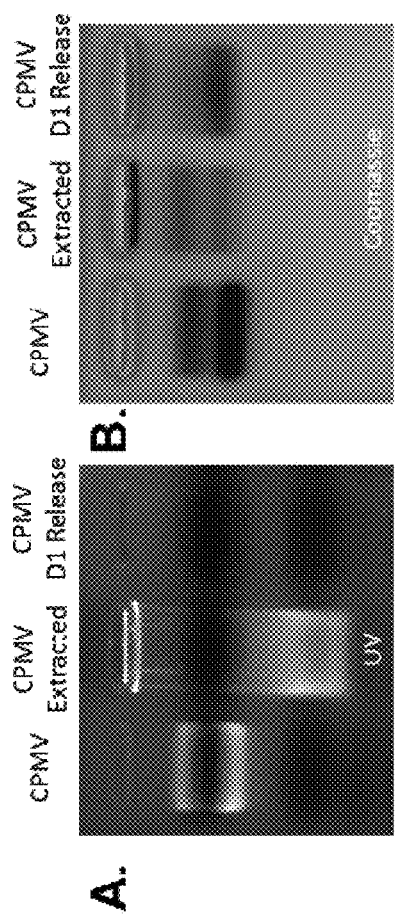
Figs. 24A-B
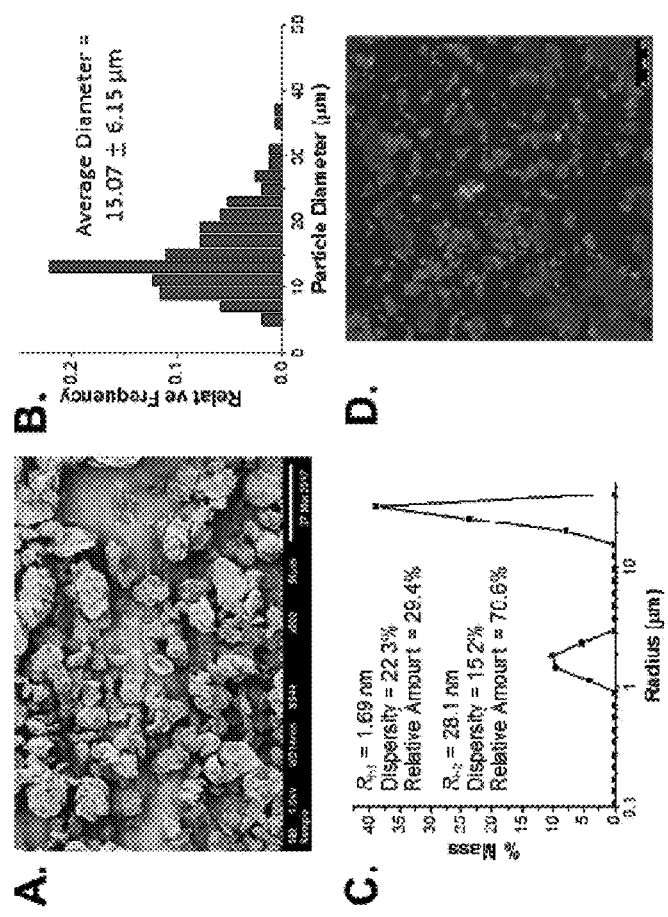
Figs. 25A-D

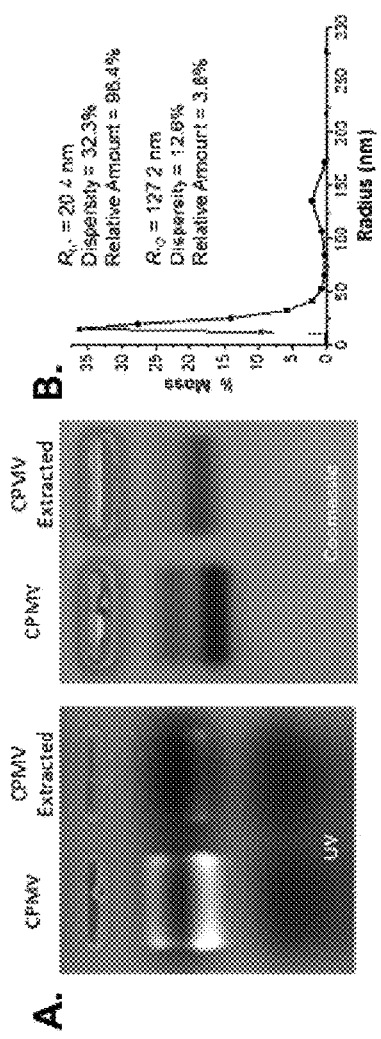
Figs. 26A-B
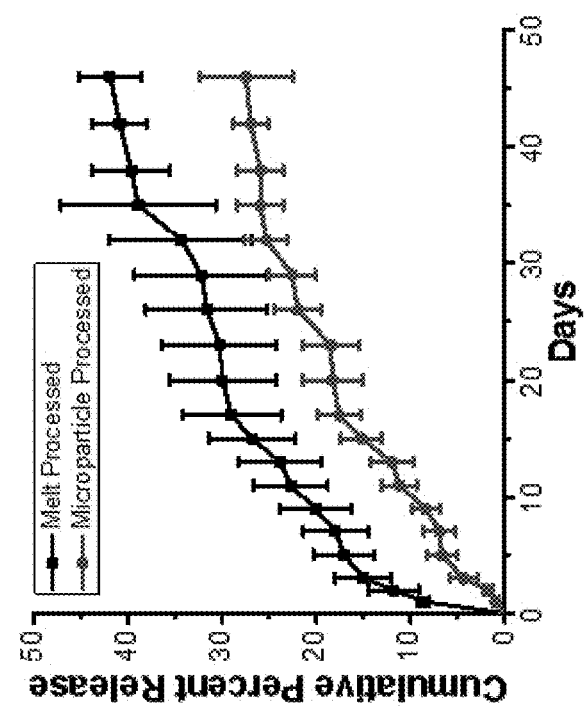
Fig. 27

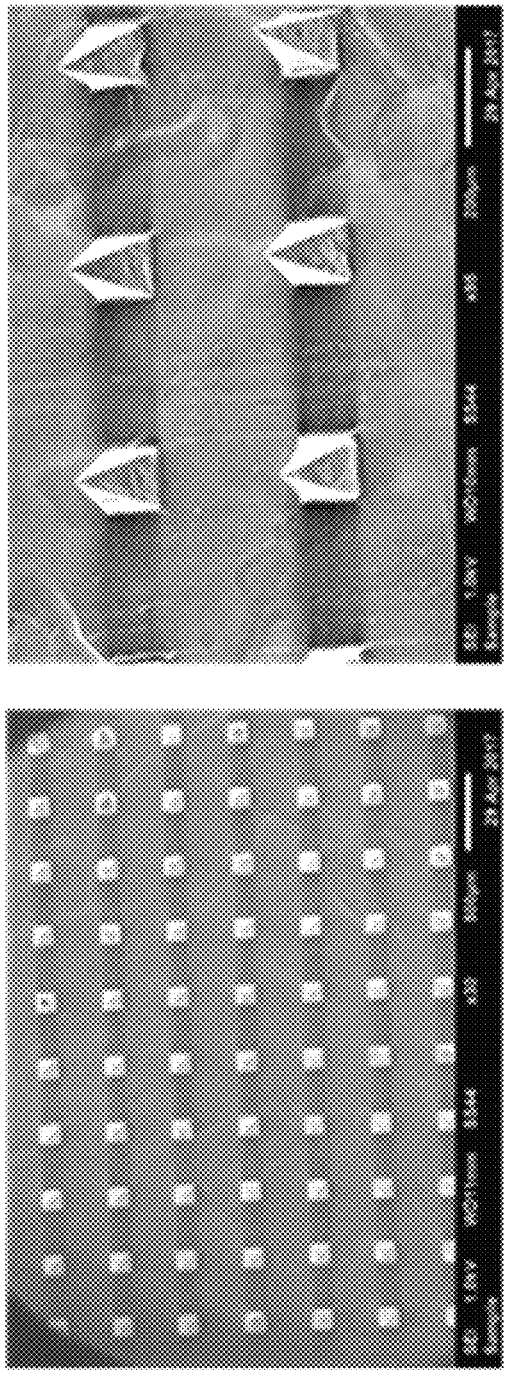
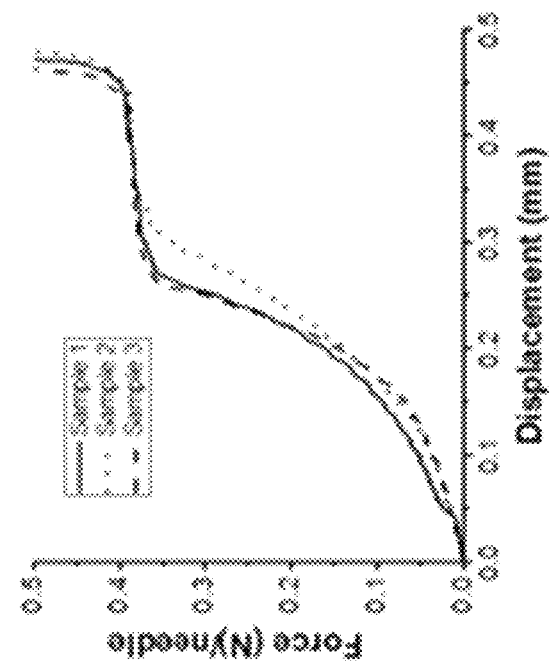
Figs. 28A-B

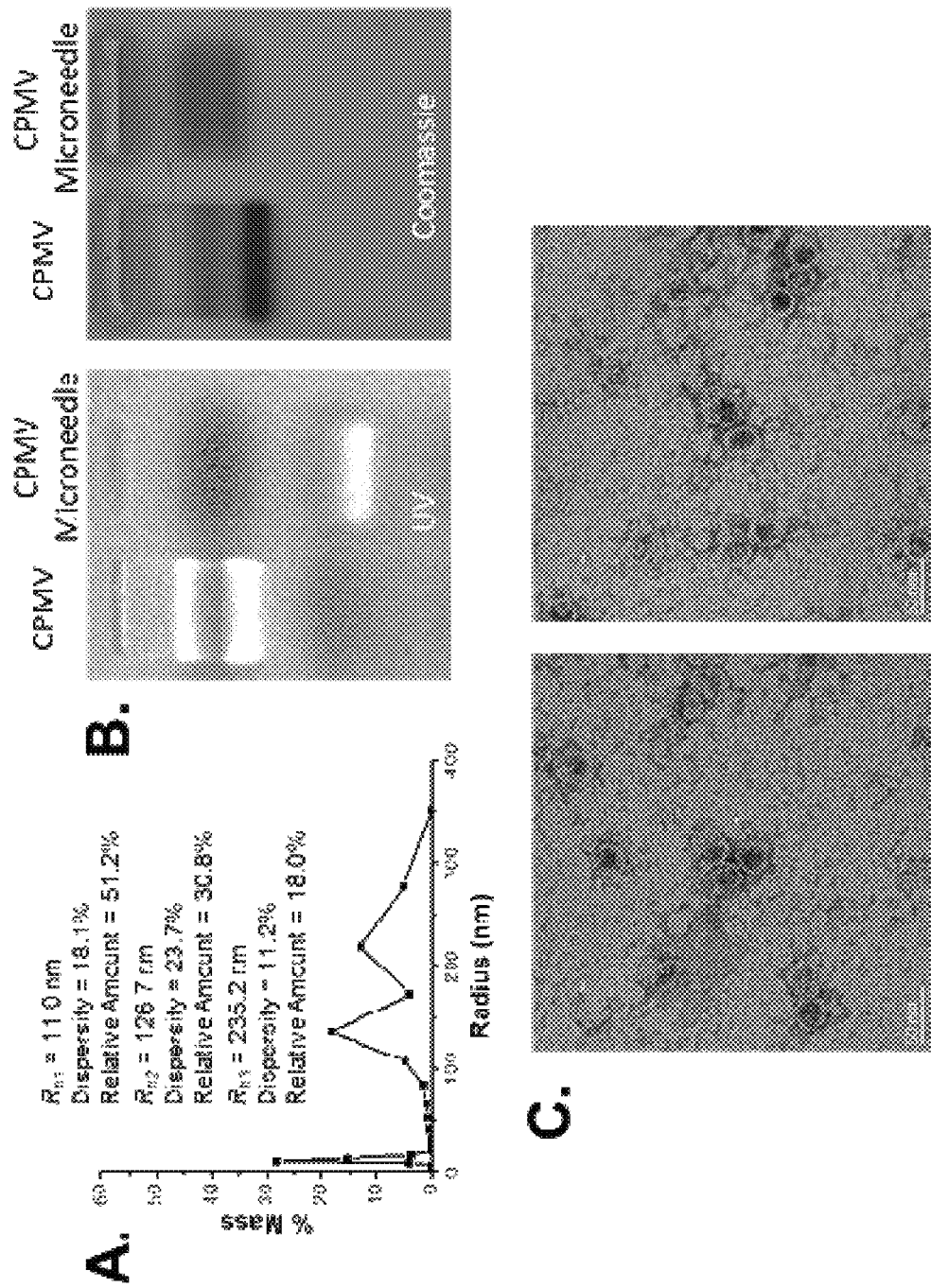
Figs. 29A-C

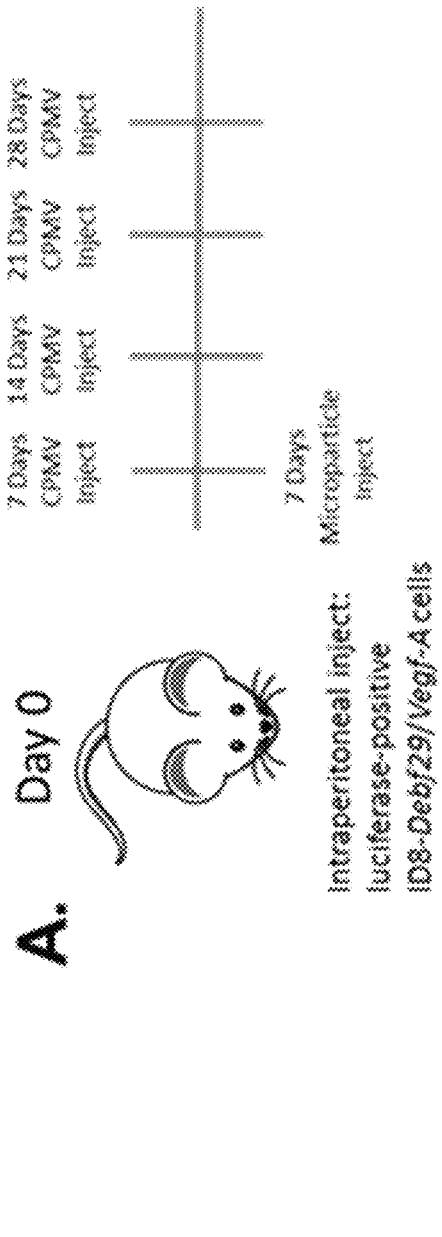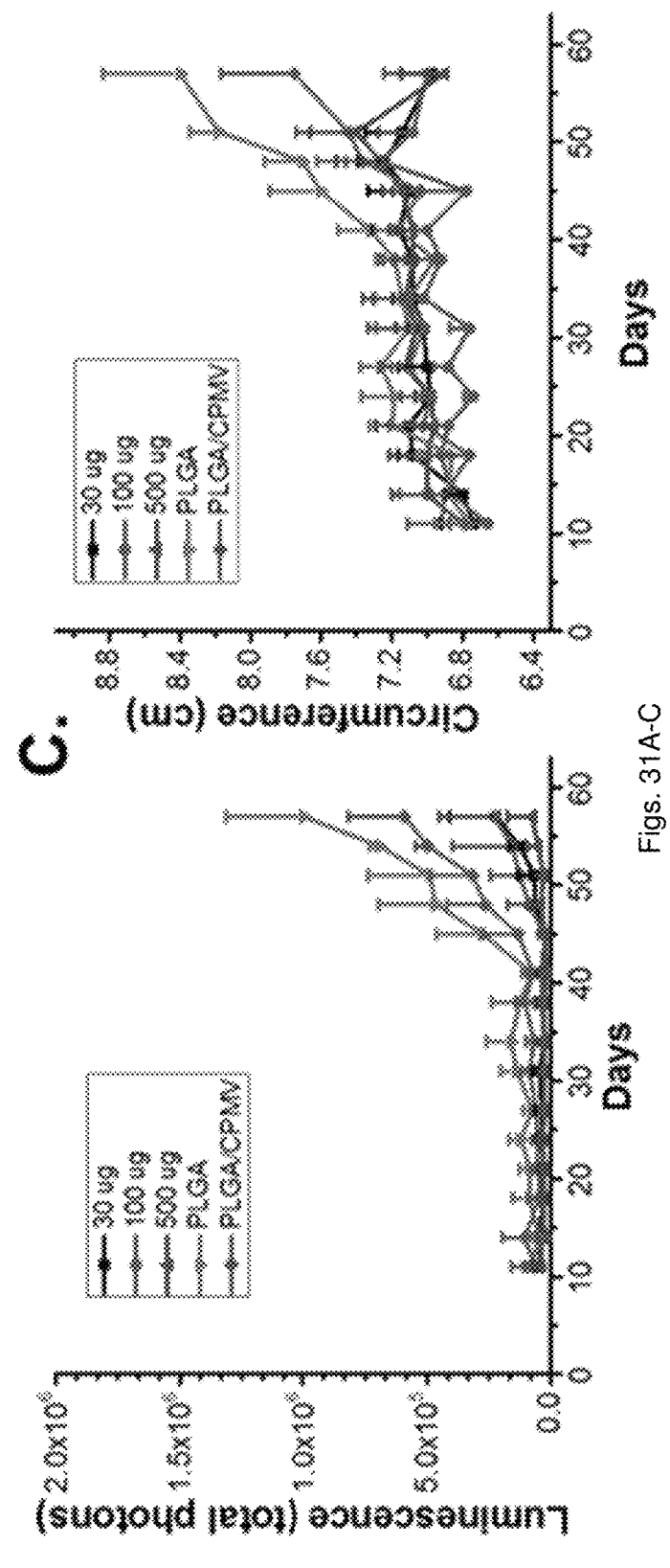
Figs. 31A-C

MELT PROCESSED VIRAL NANOPARTICLE CONSTRUCTS

RELATED APPLICATION

This application claims priority from U.S. Provisional Application No. 62/417,000, filed Nov. 3, 2016, the subject matter of which is incorporated herein by reference in its entirety.

GOVERNMENT FUNDING

This invention was made with government support under Grant No. CMMI-1333651 awarded by The National Science Foundation. The United States government has certain rights in the invention.

SEQUENCE LISTING

The instant application contains a Sequence Listing which has been submitted electronically in XML format and is hereby incorporated by reference in its entirety. Said XML copy, created on Nov. 14, 2023, is named CWR-026164US CON-1.st.26 and is 8,353 bytes in size.

BACKGROUND

Biodegradable polymeric devices have been designed for drug delivery. Among the different classes of biodegradable polymers, the thermoplastic aliphatic poly(esters), such as poly(lactide) (PLA), poly(glycolide) (PGA), and especially the copolymer of lactide and glycolide referred to as poly(lactide-co-glycolide) (PLGA) have generated interest because of their excellent biocompatibility, biodegradability, and mechanical strength. These polymers are easy to formulate into various devices for carrying a variety of drug classes, such as vaccines, peptides, proteins, and micromolecules, and have been approved by the United States Food and Drug Administration (FDA) for drug delivery.

Viral nanoparticles (VNPs) are a class of protein-based nanoparticles that have been extensively studied for immunology, biomedical, and agricultural applications. VNPs can consist of native or modified viral capsid proteins encapsidating the viral genome, or self-assembled capsid proteins that are non-infectious, also termed virus-like particles (VLPs). The proteinaceous nature of VNPs makes them inherently more biocompatible than synthetic nanoparticles derived from metals or polymers. The precise self-assembly of VNPs yields monodisperse sizes, overcoming heterogeneity and lack of reproducibility often seen with synthetic nanoparticles. The size range of VNPs is 20-500 nm, which promotes uptake by antigen presenting cells (APCs) and induction of an immune response. Furthermore, the surface of VNPs can be modified by covalent coupling or genetic engineering to display multiple epitopes in a regular array to direct an immune response against a non-viral target. Five FDA approved VNP vaccines are currently on the market, with several more in clinical trials, further bolstering interest in developing new VNP delivery systems for immunology, drug delivery, and agriculture.

SUMMARY

Embodiments described herein relate to a melt processed viral nanoparticle construct that includes a degradable polymer matrix and a plurality of virus or virus-like particles encapsulated within the degradable polymer matrix. The nanoparticle construct can upon delivery and/or administration to a site of interest provide a sustained and/or controlled release of the virus or virus-like particles to the site. The nanoparticle construct can also serve as a substrate for the incorporation and/or attachment of at least one cargo agent and/or bioactive agent.

Advantageously, the melt processed nanoparticle construct can be formed without solvent (i.e., solvent-free or solventless), and the virus or virus-like particles upon release from the degradable polymer matrix can have the same or substantially similar structural and biochemical characteristics as the virus or virus-like particles prior to melt processing.

In some embodiments, where the nanoparticle construct is used for therapeutic applications, the site of interest can be a cell or tissue of a subject. In other embodiments, where the nanoparticle construct is used for agricultural applications, the site of interest can be a plant propagation material, a plant, part of a plant and/or plant organ.

In some embodiments, the melt processed nanoparticle construct can be provided in shape (e.g., plurality of microparticles or microneedles) that can be readily delivered to a subject to provide controlled and/or sustained release of the virus or virus-like particles as well as cargo molecules and/or bioactive agents coupled to and/or loaded on the construct to cells and/or tissue of a subject. The melt processed nanoparticle construct can be administered, injected, or implanted in a minimally invasive fashion in a subject in need thereof to treat diseases (e.g., cancer) and/or disorder in the subject.

In some embodiments, the degradable polymer matrix can include a melt processable degradable polymer material that is biocompatible and, upon degradation, produces substantially non-toxic products. The virus or virus-like particles can have a release profile from the degradable polymer matrix at least partially defined by the degradation of the degradable polymer material under environmental and/or physiological conditions.

In other embodiments, the degradable polymer material can be melt processed at a Peclet number of about 5 to about 25. The degradable polymer material can also have a melt temperature below a degradation temperature of the virus or virus-like particles.

In some embodiments, the degradable polymer material includes poly(lactic-co-glycolic acid) (PLGA) or a copolymer thereof. The polymer matrix can also include at least one porogen, such as polyethylene glycol.

In some embodiments, the virus or virus-like particle is a bacteriophage or plant virus or virus like particle. The bacteriophage virus or virus-like particle can be Qβ-phage, AP 205-phage, GA-phage, fr-phage, or M2 phage. The plant virus or virus-like particle used to for the nanoparticle construct can be a plant picornavirus or a filamentous plant virus or virus like particle. The plant virus or virus-like particle can be of the Secoaviridoe genus or Alphafexiviridae family. For example, the plant virus or virus-like particle can be a cowpea mosaic virus-like particle or potato virus X virus-like particle. In other embodiments, the plant virus particle or virus like particle can be a rod-shaped virus particle. The rod-shaped virus can be a tobacco mosaic virus.

Other embodiments described herein relate to methods of treating cancer in a subject in need thereof by administering in situ to cancer of the subject a therapeutically effective amount of a melt processed nanoparticle construct. The melt processed nanoparticle construct can include a biodegradable polymer matrix and a plurality of virus or virus-like particles encapsulated within the biodegradable polymer matrix. The virus or virus-like particles can be nonreplicating and noninfectious in the subject to avoid infection of the subject. In some embodiments, the in situ administration of the nanoparticle construct can be proximal to a tumor in the subject or directly to the tumor site to provide a high local concentration and sustained and/or controlled release of the virus or virus like particles in the tumor microenvironment. The method represents a type of sustained or slow release in situ vaccination, in which application of an immunostimulatory reagent directly to the tumor modifies the tumor microenvironment so that the immune system is able to respond to the tumor.

In some embodiments, a dose of the virus or virus-like particles can be coadministered with the nanoparticle construct in situ to cancer of the subject to provide an initial immune response prior to sustained release of the virus or virus-like particles from the nanoparticle construct.

BRIEF DESCRIPTION OF THE DRAWINGS

FIGS. 1(A-B) illustrate A) structures of PLGA and Qβ. B) A schematic diagram of the syringe-die melt-encapsulation device showing the internal structure of device and resulting cylindrical extrudates.

FIGS. 2(A-F) illustrate (A) FPLC chromatogram, (B) DLS histogram, and (C) TEM image of Qβ showing the typical Gaussian peak on the chromatogram and expected sizes in the DLS and TEM results before melt encapsulation. (D) FPLC chromatogram, (E) DLS histogram, and (F) TEM image of recovered Qβ after melt-encapsulation with PLGA. The peak at 10 mL in the FPLC chromatogram corresponded to aggregated species eluting at the void volume, which also appear as the larger peak in the DLS histogram. The TEM result, along with the FPLC and DLS result, indicated that a large proportion of the particles remain intact and are of the correct size.

FIGS. 3(A-F) illustrate EDS spectrum sulfur K-series emission signal (S K series) map of (A) 1 wt % Qβ, (B) 5 wt % Qβ, and (C) 10 wt % Qβ loaded PLGA material cross-sections indicating good dispersion of Qβ within the polymeric matrix. Full-scale SEM images of (D) 1 wt % Qβ, (E) 5 wt % Qβ, and (F) 10 wt % Qβ loaded PLGA material cross-sections.

FIGS. 4(A-B) illustrate (A) FPLC chromatogram and (B) DLS histogram of melt-pressed and recovered Qβ indicating an increase in aggregated species eluting at 10 mL in the chromatogram and an increase in the size of aggregated species centered at $R_h$=71.3 nm in the DLS histogram.

FIGS. 5(A-H) illustrate FPLC chromatograms of recovered Qβ samples subjected to shear rates of (A) 0.1 $s^{-1}$, (B) 1 $s^{-1}$, (C) 10 $s^{-1}$, and (D.) 50 $s^{-1}$. DLS plots of recovered Qβ samples subjected to shear rates of (E.) 0.1 $s^{-1}$, (F.) 1 $s^{-1}$, (G.) 10 $s^{-1}$, and (H.) 50 $s^{-1}$. Both FPLC and DLS results indicate that low shear rates, from 0.1 to 1 $s^{-1}$ resulted in an increase in aggregated species. Higher shear rates, up to 10 $s^{-1}$, dispersed aggregated species due to the higher shear forces applied. Shear rates exceeding 10 $s^{-1}$ induced particle break-up as evidenced by the appearance of a large peak at 22.5 mL on the FPLC chromatogram.

FIGS. 6(A-B) illustrate (A) Plot of the mass average normalized radius versus applied shear rate (top axis) and Peclet number (bottom axis). Plotting the aggregation behavior versus the shear rate and Peclet number allows for the determination of ideal processing parameters to prevent excessive aggregation and particle break-up of Qβ in PLGA and other polymeric systems during melt-processing (B) Applied energy to the particles versus total particle disulfide energy analysis indicating the thermal and shear energy approached the level of disulfide energy in the Qβ particles at 25 and 50 $s^{-1}$ shear rates, resulting in the observed particle break-up.

FIGS. 7(A-B) illustrate release profiles of (A) 1 wt % Qβ loaded PLGA samples with 10 wt % PEG 8K and PEG 20K additives and (B) 1, 5, and 10 wt % loaded Qβ loaded PLGA. Reported as the average and standard deviation of 3 samples.

FIGS. 8(A-C) illustrate (A) Immunization and bleeding schedule of mice implanted with 0.5 cm of 10 wt % Qβ loaded PLGA and mice immunized via 3 subcutaneous injections of 50 µg Qβ. (B) End-point titers of anti-Qβ IgG indicating the implanted PLGA/Qβ devices immunize as effectively as repeated Qβ administration and (C.) IgG subtype percentages of mice immunized via subcutaneous injection and device implantation, which indicate similar immune response via the same IgG subtype generation between mice immunized via injection and implantation. The arrow indicates a challenge with 50 µg Qβ for all mice and the IgG subtypes were measured using sera collected on day 65. Titers and subtype percentages are reported as the average and standard deviation of measurements from 5 mice.

FIG. 11 illustrates ELISA response from wild type, melt processed, and microneedle reprocessed Qβ. The absorbance at 405 nm, indicative of the antibody binding to Qβ, was normalized to the wild type Qβ value to yield a percent antibody recognition. The results are reported as the average and standard deviation from results using sera from 2 immunized mice with sera for each sample read in triplicate.

FIGS. 12(A-B) illustrate (A) FPLC chromatogram and (B) DLS histogram of Qβ conjugated with Cy5. The 650 nm absorbance shown in the chromatogram was indicative of the Cy5 dye.

FIG. 17 illustrates vaccination and sera collection scheme for treatment groups. 5 groups of 5 mice each were immunized via subcutaneous injection of either 50 μg of wild type Qβ, Qβ-P4, or CH401(Rat) or 2 μg of free P4 or CH401(Rat) peptide. Serum was collected prior to injections.

FIGS. 18(A-B) illustrate (A) P4 specific ELISA response for mice immunized with Qβ, Qβ-P4, and P4 from sera collected on day 0, 14, 28, and 42. (B) CH401(Rat) specific ELISA response for mice immunized with Qβ, Qβ-CH401 (Rat), and CH401(Rat) from sera collected on day 0, 14, 28 and 42. All results were reported as the average and standard deviation of measurements of sera from 5 mice.

FIG. 19 illustrates Qβ specific ELISA response for mice immunized with Qβ, Qβ-P4, and Qβ-CH401(Rat) from sera collected on day 0, 14, 28, and 42. All results were reported as the average and standard deviation of measurements of sera from 5 mice.

FIGS. 20(A-C) illustrate (A) FPLC chromatogram, (B) DLS histogram, and (C) TEM micrograph of wild type Qβ melt processed at 10 wt % with PLGA.

FIGS. 21(A-F) illustrate (A) FPLC chromatogram, (B) DLS histogram, and (C) TEM micrograph of Qβ-P4 melt processed at 10 wt % with PLGA. (D) FPLC chromatogram, (E) DLS histogram, and (F) TEM micrograph of Qβ-CH401 (Rat) melt processed at 10 wt % with PLGA.

FIGS. 24(A-B) illustrate Agarose gel results for CPMV, CPMV recovered via organic extraction, and CPMV recovered via 24 hour aqueous release. (A) UV image of the gel showing RNA stained with 1% ethidium bromide and (B) optical image of the gel showing protein stained with Coomassie.

FIGS. 25(A-D) illustrate (A) SEM image of CPMV/ PLGA/PEG8000 microparticles collected at 500× magnification and 1.0 kV accelerating voltage. (B) Frequency histogram of microparticle diameter determined from microparticle SEM images. Due to the range of round to elliptical shapes exhibited by the particles, the diameter was defined as the longest distance across a particle. The histogram was determined from 150 particle measurements from 2 SEM images. (C) DLS histogram of microparticles suspended in phosphate buffered saline. (D) Confocal image of microparticles containing 5 wt % PLGA-FPI749 with particles shown in green ($\lambda_{ex}$=635 nm, $\lambda_{em}$=700-800 nm).

FIGS. 26(A-B) illustrate Agarose gel results for CPMV and CPMV recovered via 24 hour aqueous release from microparticles. (A) UV image of the gel showing RNA stained with 1% ethidium bromide and optical image of the gel showing protein stained with Coomassie. (B) DLS histogram of CPMV released from microparticles.

FIG. 27 illustrates in vitro release profile of CPMV released from rod-shaped melt processed samples and CPMV released from cryo-milled microparticle samples. Reported as the average and standard deviation of 3 samples.

FIGS. 28(A-B) illustrate (A) SEM image of PLGA/ PEG8000 microneedle arrays collected at 30× (left) and 95× (right) magnification and 1.0 kV accelerating voltage. (B) Force versus displacement curves for the microneedle samples normalized as the force per single needle. The maximum strength was defined as the first plateau of the force and the curves are representative of 3 individual samples.

FIGS. 29(A-C) illustrate (A) DLS histogram of CPMV extracted from the microneedle array. (B) Agarose gel results for CPMV and CPMV recovered via extraction from the microneedle array with the UV image of the gel showing RNA stained with 1% ethidium bromide on the left and the optical image of the gel showing protein stained with Coomassie on the right. (C) TEM image of extracted CPMV from the microneedle array. The irregular white signal arose due to the polymer background in the sample.

FIGS. 31(A-C) illustrate (A) Schematic of the injection schedule for OVCA treatment. Doses of 30, 100, and 500 μg were injected 4 times on a weekly schedule, denoted as 'CPMV Inject'. A single dosage of either PLGA/PEG8000 microparticles or CPMV/PLGA/PEG8000 microparticles were injected at day 7, denoted as 'Microparticle Inject'. (B) Total luminescence from the luciferase reporter gene in the ID8-DebJ29/Vegf-A ovarian cancer cells. The luminescence value was representative of tumor growth. Reported as the average and standard deviation of 5 mice for each group. (C) Abdominal circumference measurement for each treatment group, representative of fluid retention and tumor growth in the intraperitoneal space. Reported as the average and standard deviation of 5 mice for each group.

DETAILED DESCRIPTION

Figure 9A:
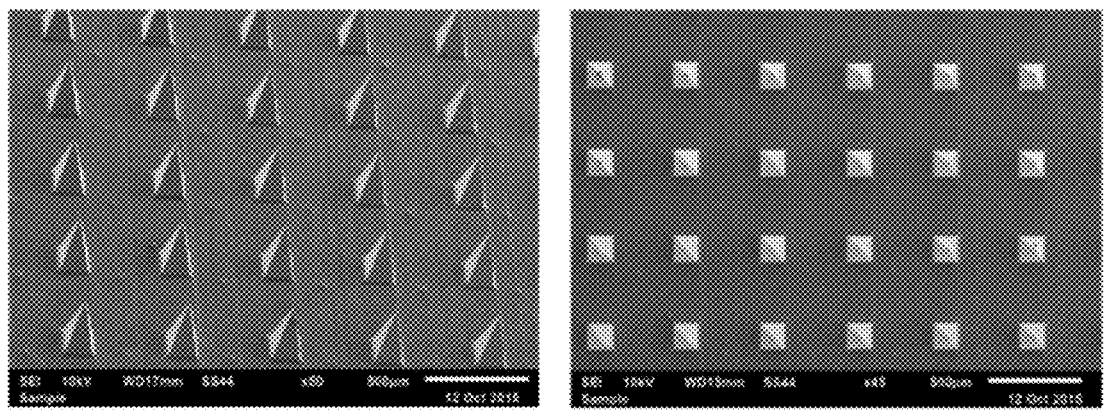
FIGS. 9(A-B) illustrate (A) SEM micrographs of PLGA microneedle arrays prepared via melt molding. The images were collected at 50× (left) and 45× (right) magnification using a 10 kV accelerating voltage. (B) Force versus displacement curves for the microneedle samples normalized as the force per single needle. The maximum strength was defined as the first plateau.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

The term "about" when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

The term "agent" is used herein to denote a chemical compound, a mixture of chemical compounds, a biological macromolecule, or an extract made from biological materials.

The term "bioactive agent" can refer to any agent capable of promoting a biological effect, e.g., alters or modulates a biological function of a physiological target substance. By "alters" or "modulates a biological function" herein is meant that the physiological target undergoes a change in either the quality or quantity of its biological activity; this includes increases or decreases in activity. Thus, bioactive agents include a wide variety of drugs, including antagonists, for example enzyme inhibitors, and agonists, for example a transcription factor which results in an increase in the expression of a desirable gene product (although as will be appreciated by those in the art, antagonistic transcription factors may also be used), are all included.

In addition, a "bioactive agent" includes those agents capable of direct toxicity and/or capable of inducing toxicity towards healthy and/or unhealthy cells in the body. Also, the bioactive agent may be capable of inducing and/or priming the immune system against potential pathogens. A number of mechanisms are possible including without limitation, (i) a radioisotope linked to a protein as is the case with a radiolabled protein, (ii) an antibody linked to an enzyme that metabolizes a substance, such as a prodrug, thus rendering it active in vivo, (iii) an antibody linked to a small molecule therapeutic agent, (iv) a radioisotope, (v) a carbohydrate, (vi) a lipid, (vii) a thermal ablation agent, (viii) a photosensitizing agent, and (ix) a vaccine agent.

The terms "biocompatible" and "biologically compatible" refer to materials that are, along with any metabolites or degradation products thereof, generally non-toxic to the recipient, and do not cause any significant adverse effects to the recipient, at concentrations resulting from the degradation of the administered materials. Generally speaking, biocompatible materials are materials that do not elicit a significant inflammatory or immune response when administered to a patient.

The term "biodegradable polymer" generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment.

The term "cargo molecule," refers to a small organic or inorganic bioactive agent, such as a drug or imaging agent that can be associated with a virus nanoparticle in order to confer an additional function on the virus nanoparticle.

The term "controlled release" refers to control of the rate and/or quantity of a virus nanoparticles, cargo molecules, and/or bioactive agents delivered using the nanoconstructs described herein. The controlled release can be continuous or discontinuous, and/or linear or non-linear. This can be accomplished using one or more types of polymer materials or compositions, drug loadings, inclusion of excipients or degradation enhancers, or other modifiers, administered alone, in combination or sequentially to produce the desired effect.

The term "effective amount" refers to an amount of virus nanoparticles, cargo molecules, and/or bioactive agents that is sufficient to provide a desired effect. An effective amount in any individual case may be determined by one of ordinary skill in the art using routine experimentation.

The term "imaging agent" can refer to a biological or chemical moiety capable being linked and/or conjugated directly or indirectly to nanoparticle constructs described herein and that may be used to detect, image, and/or monitor the presence and/or progression of a cell cycle, cell function/physiology, condition, pathological disorder and/or disease.

The term "linker" or "linker molecule," as used herein, refers to a molecule including linker region made up of a long hydrophilic carbon chain or hydrophilic polymer, and two or more attachment sites provided at the ends of the linker molecule that allow the linker to be reacted with virus particles and/or attachment sites on a support surface.

The terms "matrix" and "polymer matrix" refer to a three-dimensional network of polymer materials or compounds. The polymer materials or compounds are arranged in such a way as to permit the inclusion of other materials compounds inside the three dimensional network.

The term "subject" can be a human or non-human animal. Non-human animals include, for example, livestock and pets, such as ovine, bovine, porcine, canine, feline and murine mammals, as well as reptiles, birds and fish. Preferably, the subject is human.

Embodiments described herein relate to a melt processed viral nanoparticle construct that includes a degradable polymer matrix and a plurality of virus or virus-like particles encapsulated within the degradable polymer matrix. The nanoparticle construct can upon delivery and/or administration to a site of interest provide a sustained and/or controlled release of the virus or virus-like particles to the site. The nanoparticle construct can also serve as a substrate for the incorporation and/or attachment of at least one cargo agent and/or bioactive agent.

Advantageously, the melt processed nanoparticle construct can be formed without solvent (i.e., solvent-free or solventless), and the virus or virus-like particles upon release from the degradable polymer matrix can have the same or substantially similar structural (e.g., size, shape, and morphology) and biochemical (e.g., immune response) characteristics of as the virus or virus-like particles prior to melt processing.

In some embodiments, where the nanoparticle construct is used for therapeutic applications, the site of interest can be a cell or tissue of a subject. In other embodiments, where the nanoparticle construct is used for agricultural applications, the site of interest can be a plant propagation material, a plant, part of a plant and/or plant organ.

In some embodiments, the nanoparticle construct can be provided in shape (e.g., a plurality of microparticles or microneedles) that can be readily delivered to a subject to provide controlled and/or sustained release of the virus or virus-like particles as well as cargo molecules and/or bioactive agents coupled to and/or loaded on the construct to cells and/or tissue of a subject. The nanoparticle construct can be administered, injected, or implanted in a minimally invasive fashion in a subject in need thereof to treat diseases (e.g., cancer) and/or disorder in the subject.

The degradable polymer matrix can include or be made of a melt processable degradable polymer material. The melt processable degradable polymer material can be, for example, hydrolytically degradable, biodegradable, thermally degradable, and/or photolytically degradable.

The degradable polymer material can also have a melt temperature that allows the degradable polymer to be readily processed by, for example, melt extrusion, and below the degradation temperature of the virus or virus-like particles. For example, the degradable polymer material can have a melt temperature below about 120° C., about 110° C., about 100° C., about 90° C., about 80° C., or about 70° C. and be readily extruded without the aid of solvents with the virus or virus-like particles to form the melt processed nanoparticle construct.

Degradable polymers can include, for example, certain polyesters, polyanhydrides, polyorthoesters, polyphosphazenes, polyphosphoesters, certain polyhydroxyacids, polypropylfumerates, polycaprolactones, polyamides, poly (amino acids), polyacetals, polyethers, biodegradable polycyanoacrylates, biodegradable polyurethanes and polysaccharides. For example, biocompatible, biodegradable, or bioerodible polymers include poly(lactic acid) (PLA), poly (glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic or Poloxamer) and copolymers and blends of these polymers.

In certain embodiments, poly(lactic-co-glycolic acid) (PLGA) can be used as the melt processable biodegradable polymer. Biodegradable polymers fabricated from PLGA have emerged as powerful potential carriers for small and large molecules of therapeutic importance as well as scaffolds for tissue engineering applications. This importance derives from: 1) Physiologic compatibility of PLGA and its hompolymers PGA and PLA, all of which have been established as safe in humans after 30 years in various biomedical applications including drug delivery systems 2) Commercial availability of a variety of PLGA formulations for control over the rate and duration of molecules released for optimal physiological response(Visscher et al. J Biomed Mater Res 1985; 19(3):349-65; Langer R, Folkman J. Nature 1976; 263(5580):797-800; Yamaguchi. J. Controlled Rel. 1993; 24(1-3):81-93.). 3) Biodegradability of PLGA materials, which provides for sustained release of the encapsulated molecules under physiologic conditions while degrading to nontoxic, low-molecular-weight products that are readily eliminated (Shive et al. Adv Drug Deliv Rev 1997; 28(1): 5-24; Johansen et al. Eur J Pharm Biopharm 2000; 50(1): 129-46). 4) Control over its manufacturing into nanoscale particles (<500 nm) for potential evasion of the immune phagocytic system or fabrication into microparticles on the length scale of cells for targeted delivery of drugs or as antigen-presenting systems(Eniola et al. J Control Release 2003; 87(1-3):15-22; Jain R A. Biomaterials 2000; 21(23): 2475-90).

The degradable polymers described herein can have a variety of molecular weights. The polymers may, for example, have molecular weights of at least about 5 kD, at least about 10 kD, at least about 20 kD, at least about 22 kD, at least about 30 kD, or at least about 50 kD.

The degradable polymers and derivatives thereof can be selected and adapted to have a desired degradation rate. Alternatively or additionally, a degradation rate may be fine-tuned by associating or mixing other materials (e.g., non-degradable materials) with one or more of degradable polymer material.

In general, a degradation rate as used herein can be dictated by the time in which a material degrades a certain percentage (e.g., 50%) in a certain condition (e.g., in physiological conditions). In some embodiments, the degradation time of the nanoparticle construct or a portion of the nanoparticle construct as described herein can have a wide range. In some embodiments, the degradation time may be greater than 1 minute, 5 minutes, 30 minutes, 1 hour, 2 hours, 5 hours, 12 hours, 24 hours, 1.5 days, 2 days, 5 days, 7 days, 15 days, 30 days, 2 months, 6 months, 1 year, 2 years, or even 5 years. In embodiments, the degradation time may be about or less than 10 years, 5 years, 2 years, 1 year, 6 months, 2 months, 30 days, 15 days, 7 days, 5 days, 2 days, 1.5 days, 24 hours, 12 hours, 5 hours, 2 hours, 1 hour, 30 minutes or even 5 minutes. The degradation time may be in a range of 12-24 hours, 1-6 months, or 1-5 years. In some embodiments, the degradation time may be in a range of any two values above.

In other embodiments, the nanoparticle construct is designed to release virus or virus-like particles to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly(lactic acid) (PLA), more hydrophilic poly (glycolic acid) PGA and their copolymers, poly(lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Optionally, the degradable polymer matrix can include one or more porogens to enhance or accelerate the release of the virus or virus like particles from the melt processed nanoparticle construct. The porogen can be added during melt processing of the degradable polymer material and virus or virus-like particles. The porogen can include any compound that will reserve a space within the degradable polymer matrix of the nanoparticle construct while the nanoparticle construct is being formed.

Porogens may be of any shape or size. A porogen may be spheroidal, cuboidal, rectangular, elonganted, tubular, fibrous, disc-shaped, platelet-shaped, polygonal, etc. In certain embodiments, the porogen is granular with a diameter ranging from about 10 μm to about 800 μm (e.g., about 25 μm to about 100 μm). In certain embodiments, a porogen is elongated, tubular, or fibrous.

The amount of porogens may vary in the formation of the nanoparticle construct and range from 1% to 80% by weight. Pores can provide for easier degradation of the degradable polymer matrix and facilitate release of the virus or virus-like particles from the degradable polymer matrix. In some embodiments, a porogen is biocompatible.

In some embodiments, a porogen may be a gas, liquid, or solid. Examples of possible solid porogens include water soluble compounds. Exemplary porogens include peptides and proteins (e.g., gelatin), carbohydrates, salts, sugar alcohols, natural polymers, synthetic polymers, and small molecules. In one example, the porogen can be polyethylene glycol, which is a known porogen of PLGA materials.

The nanoparticle construct can be formed using a variety of different types of viral nanoparticles. The term viral nanoparticle can refer to virus or virus particles, which include a nucleic acid encoding the virus, and virus-like particles, which do not include a nucleic acid encoding the virus. Viral nanoparticles are readily modifiable through both genetic engineering and chemical modification, with a well-ordered, multivalent display of functional groups on exterior as well as interior surfaces of viral nanoparticles. They are also highly economical as production can be scaled up using molecular farming or fermentation.

Viral nanoparticles encapsulated by the melt processable degradable polymer matrix described herein can be categorized based on their source and structure. For example, viral nanoparticles from mammalian, avian, bacterial, or plant sources can be used. One advantage of using viral nanoparticles from plant sources is that they can be readily cultivated, and are unlikely to cause infection when used in vivo in a subject. In addition, viral nanoparticles can have a helical, icosahedral, or prolate structure can be used. Examples of helical viruses include tobaviruses such as tobacco mosaic virus and filamentous bacteriophages, e.g., M13 and fd. A variety of helical viruses are described by Stubbs et al., Adv. Exp. Med. Bio., 726, p. 631-658 (2012), the disclosure of which is incorporated herein by reference. Examples of icosahedral viruses include Qβ, P22 and other bacteriophages, HIV, herpesvirus, adenovirus, poliovirus, human papillomavirus, and picomaviruses, as well as various plant viruses such as cowpea mosaic virus, brome mosaic virus, cowpea chlorotic mottle virus, etc.

In some embodiments, the bacteriophage virus or virus-like particle can be Qβ-phage, AP 205-phage, GA-phage, fr-phage, or M2 phage.

In other embodiments, the plant virus or virus like particles can be an icosahedral plant virus or virus like particle. Examples of icosahedral plant viruses include the virus families Geminiviridae, Luteoviridae, Bromoviridae, Phycodnaviridae, and Picomaviridae. In some embodiments, the icosahedral plan virus is from the family Picomaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus comovirus. An example of a comovirus is the cowpea mosaic virus particles.

In other embodiments, the plant virus or virus like particle is a filamentous plant virus. Filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm.

In some embodiments, the filamentous plant virus belongs to a specific virus family, genus, or species. For example, in some embodiments, the filamentous plant virus belongs to the Alphaflexiviridae family. The Alphaflexiviridae family includes the genus Allexivirus, Botrexvirus, Lolavirus, Mandarivirus, Potexvirus, and Sclerodamavirus. In some embodiments, the filamentous plant virus belongs to the genus Potexvirus. In further embodiments, the filamentous plant virus belongs to the Potato Virus X species.

In other embodiments, the plant virus or virus-like particle can be based on a rod-shaped plant virus or virus like particle. A rod-shaped plant virus is a virus that primarily infects plants, is non-enveloped, and is shaped as a rigid helical rod with a helical symmetry. Rod shaped viruses also include a central hollow canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus Furovirus, Hordevirus, Pecluvirus, Pomovirus, Tobamovirus, and Tobravirus. In some embodiments, the rod-shaped plant virus belongs to the genus Tobamovirus. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are about 300 nm in length and about 18 nm in diameter. Negatively stained electron microphotographs show a distinct inner channel of about 4 nm.

The virus or virus-like particles can be obtained according to various methods known to those skilled in the art. In embodiments where plant virus particles are used, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

The viral nanoparticles can be encapsulated within the degradable polymer matrix by melt processing, such as melt encapsulation. In melt encapsulation, dry powders of degradable polymer material, virus or virus-like particles and other additives are mixed and then heated above the melt or glass transition of the polymer material but below the degradation temperature of the virus or virus-line particles. The mixture can then be molded (e.g., compression molded and/or extrusion/injection molded) and cooled to a desired shape or configuration. The melt processing (e.g., melt encapsulation) and/or post processing (e.g., extrusion) conditions of the mixture can be controlled such that the concentrations of the materials in the mixture are relatively consistent throughout and a melt processed nanoparticle construct is provided in which the viral nanoparticles can be substantially uniformly dispersed within the degradable polymer matrix and the virus or virus-like particles upon release from the degradable polymer matrix can have the same or substantially similar size, shape, and biochemical characteristics (e.g., immune response) as the virus or virus-like particles prior to melt processing.

The conditions during melt processing can be defined or measured in terms of a Peclet number. Advantageously, a Peclet number of about 5 to about 25 is maintained during melt processing of degradable polymer material and the virus or virus-like particles. Maintaining the Peclet number between about 5 to about 25 during melt processing of the degradable polymer material and the virus or virus-like particles allows the virus or virus-like particles uniformly dispersed within the degradable polymer matrix without aggregation and maintain the virus or virus-like particles' structural and biochemical integrity (e.g., immune response).

The viral nanoparticles can be mixed or loaded with the degradable polymer material at loading levels of about 1%, 5%, 20%, 25% or more to provide a nanoparticle construct with viral nanoparticle loading levels of about 1%, 5%, 20%, 25% or more. The loading level can influence the release profile form the degradable polymer matrix of the nanoparticle construct. In some embodiments, increasing the loading level can increase the amount of viral nanoparticles initially released from the nanoparticle construct.

In some embodiments, the melt processed nanoparticle constructs can be loaded with one or more cargo molecules and/or bioactive agents. For example, the cargo molecule and/or bioactive agent can be loaded by covalently attaching the cargo molecule and/or bioactive agent to a reactive molecule on a surface (interior or exterior) of one or more virus or virus like particles prior to melt processing. In other embodiments, the nanoparticle construct can be loaded with cargo molecules and/or bioactive agents by mixing the cargo molecules and/or bioactive agents with the viral nanoparticles and degradable polymer material during melt processing.

A variety of different types of cargo molecules and/or bioactive agents can be loaded into or onto the nanoparticle constructs. Cargo molecules and/or bioactive agents are generally relatively small organic or inorganic molecules. In some embodiments, the cargo molecules have a molecular weight ranging from about 50 to about 5000 daltons, with some embodiments being directed to cargo molecules having a weight ranging from about 50 to about 1000 daltons, or from about 100 to about 500 daltons. Examples of cargo molecules are imaging agents and therapeutic agents such as antitumor agents.

In some embodiments, the nanoparticle construct is modified to carry an imaging agent. Examples of imaging agents include fluorescent compounds, radioactive isotopes, and MRI contrast agents. For example, in some embodiments, the imaging agent is a fluorescent molecule for fluorescent imaging. The imaging agent can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Means of detecting imaging agents are well known to those of skill in the art. Thus, for example, where the imaging agent is a radioactive compound, means for detection include a scintillation counter or photographic film as in autoradiography. Where the imaging agent includes a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label.

Examples of imaging agents that can be used include magnetic beads (e.g., Dynabeads), fluorescent dyes (e.g., fluorescein isothiocyanate, AlexaFluor555, Texas red, rhodamine, and the like), radiolabels (e.g., $^{3}H$, $^{14}C$, $^{35}S$, $^{125}I$, $^{121}I$, $^{112}In$, $^{99m}Tc$), other imaging agents such as microbubbles (for ultrasound imaging), $^{18}F$, $^{11}C$, $^{15}O$, (for Positron emission tomography), $^{99m}TC$, $^{111}In$ (for single photon emission tomography), and chelated lanthanides such as terbium, gadolinium (e.g., chelated gadolinium), and europium or iron (for magnetic resonance imaging). The choice of imaging agent depending on sensitivity required, ease of conjugation with the compound, stability requirements, available instrumentation, and disposal provisions.

In some embodiments, the imaging agent is a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as a contrast agent is gadolinium, or more specifically gadolinium (III). Gadolinium contrast agents are generally chelated to facilitate attachment to the virus particle. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA).

In other embodiments, the cargo molecule and/or bioactive agent can be a therapeutic agent. Examples of therapeutic agents include cardiovascular drugs (e.g., antihypertensive drugs, antiarrhythmic agents, and diuretics), neuropharmaceuticals (e.g., analgesics, anesthetics, and antipsychotics), gastrointestinal drugs (e.g., anti-ulcer drugs, antiemetics, and gastroprokinetic agents), respiratory tract agents (e.g., anthasthamtic or antiallergic drugs), antiinfective agents (antibiotics, antimycotics, and antiviral agents), endocrine-affecting drugs (e.g., steroids, hormones, and contraceptives), anti-inflammatory drugs, immunosuppressant drugs, and antitumor agents.

In some embodiments, the therapeutic agents used as cargo molecules are small molecule antitumor agents. One advantage of using antitumor agents as cargo molecules is the ability of viral nanoparticles to preferentially associate with tumor cells. Examples of small molecule antitumor agents include angiogenesis inhibitors such as angiostatin K1-3, DL-α-difluoromethyl-ornithine, endostatin, fumagillin, genistein, minocycline, staurosporine, and thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine .beta.-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, deguelin, 5,6-dichlorobenz-imidazole 1-beta-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-.alpha., rapamycin, thapsigargin, and bikunin, and derivatives thereof.

The cargo molecules and/or bioactive agents can be conjugated to the virus or virus-like particles and/or other materials (e.g., degradable polymer material) of the melt processed nanoparticle constructs by any suitable technique, with appropriate consideration of the need for pharmacokinetic stability and reduced overall toxicity to the patient. The term "conjugating" when made in reference to an agent and a nanoparticle construct as used herein means covalently linking the agent to virus or virus like particles and/or other material of the nanoparticle construct subject to the limitation that the nature and size of the agent and the site at which it is covalently linked to the virus or virus like particles and/or other material of the nanoparticle construct do not interfere with the distribution of the virus or virus like particles of the nanoparticle construct. The cargo molecule can be linked to the interior or the exterior of virus or virus like particles and/or other material of the nanoparticle construct, while in some embodiments the cargo molecule is linked to both the interior and the exterior of the virus or virus like particles and/or nanoparticle construct. In some embodiments, where the cargo molecule is linked to a virus or virus like particle, the location of the cargo molecule on the interior or exterior is governed by the amino acids of viral coat proteins that are selected as reactive sites.

Cargo molecules and/or bioactive agents can be coupled to the virus or virus-like particles and/or other materials of the nanoparticle construct either directly or indirectly (e.g., via a binder group). In some embodiments, the molecule and/or agent is directly attached to a functional group capable of reacting with the agent and/or molecule. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g., alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

In other embodiments, a chemical binder group can be used. A binder group can serve to increase the chemical reactivity of a substituent on either the agent or the virus or virus like particles and/or other materials of the nanoparticle construct, and thus increase the coupling efficiency. Binder chemistries can include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146).

Further methods for conjugating polysaccharides, proteins, and lipids to plant virus peptides are described by U.S. Pat. No. 7,666,624.

In some embodiments, the surface of the virus or virus-like particles can be modified by attachment of something other than a cargo molecule. For example, the virus particle can be modified to include PEGylation, cell penetrating peptides, or targeting molecules. The nanoparticle construct can be modified either before loading the virus or virus-like particles with cargo molecules, after loading with cargo molecules, prior to melt processing, and/or after melt processing. Targeting molecules can be attached to the outside of the virus or virus-like particles in order to guide the virus or virus like particles upon release from the nanoparticle construct to a particular target tissue, such as tumor tissues. Examples of targeting molecules include peptide ligands (e.g., RGD, bombesin, or GE11), vitamins such as folic acid, and other tumor-homing proteins such as transferrin, as well as and antibodies such as Herceptin or any other antibody or antibody fragment with tumor-specific properties, and DNA-, RNA-, or PNA-based aptamers that specifically bind to an antigen present on the target tissue, such as a tumor antigen. Cell penetrating peptides can also be attached to the outside of the virus or virus-like particles to encourage internalization of the virus or virus like particles constructs. Cell penetrating peptides are generally relatively short, amphipathic peptides. Examples of cell penetrating peptides include TAT sequence or polyArginine peptides.

In some embodiments, rather than covalent attachment, cargo molecules and/or bioactive agents can also be loaded into or onto the nanoparticle constructs in a non-covalent manner by associating them with nucleic acid present within the virus particles of the nanoparticle construct. While not intending to be bound by theory, it appears that the cargo molecule associates with the nucleic acid as a result of the affinity of the cargo molecule and/or bioactive agent for the nucleic acid. Affinity is the tendency of a compound to naturally associate with another object (e.g., a nucleic acid). Affinity is influenced by non-covalent intermolecular interactions between the compound and the object, such as hydrogen bonding, electrostatic interactions, hydrophobic interactions, and Van der Waals forces.

An example of cargo molecules having an affinity for the nucleic acid are cargo molecules having a positive charge. One skilled in the art can readily determine whether a cargo molecule has affinity for the nucleic acid within a plant virus particle. For example gel mobility shift assays, oligonucleotide crosslinking assays, optical absorbance and fluorescence assays, calorimetric assays, and/or surface Plasmon resonance assays to determine the association and dissociation kinetics and affinities of cargo molecules for nucleic acids.

Furthermore, any drug or imaging agent exhibiting low affinity can be readily modified with a small, positively charged tag or complementary oligonucleotide to bind to nucleic acid within a virus particle. For some embodiments, the cargo molecules interact with nucleic acids in a reversible manner, in order to facilitate release of the cargo molecules in or to the target tissue.

In some embodiments, a targeting molecule can also be attached to the virus or virus-like particles of the nanoparticle constructs. By "targeting molecule" herein is meant a molecule which serves to target or direct the virus or virus-like particles released from the nanoparticle construct to a particular location, cell type, diseased tissue, or association. In general, the targeting molecule is directed against an antigenic site. Thus, for example, antibodies, cell surface receptor ligands and hormones, lipids, sugars and dextrans, alcohols, bile acids, fatty acids, amino acids, peptides and nucleic acids may all be attached to localize or target the virus or virus-like particles to a particular site. In some embodiments, the targeting molecule allows targeting of the virus or virus-like particles to a particular tissue or the surface of a cell.

In some embodiments, the targeting molecule is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting molecule is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin.

In some embodiments, the antibody is directed against a cell-surface marker on a cancer cell; that is, the antigenic site is a cell surface molecule. As is known in the art, there are a wide variety of antibodies and antibody fragments known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting molecule is all or a portion (e.g., a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-alpha. and TGF-beta), EPO receptor (EPO), TPO receptor (TPO), ciliary neurotrophic factor receptor, prolactin receptor, and T-cell receptors. Receptor ligands include ligands that bind to receptors such as cell surface receptors, which include hormones, lipids, proteins, glycoproteins, signal transducers, growth factors, cytokines, and others.

The nanoparticle construct can be injectable and/or implantable, and can be in the form of, for example, a membrane, sponge, gel, solid scaffold, spun fiber, woven or unwoven mesh, nanoparticles, microparticles, microneedle array or any other desirable configuration. The nanoparticle construct can be used in a variety of biomedical applications, including tissue engineering, drug discovery applications, and regenerative medicine and cancer therapy.

In one embodiment, as illustrated in FIG. 9, the nanoparticle construct can be in the form of a microneedle array that includes a plurality of microprotrusion or microprojections that can be used to penetrate the skin or other biological membranes. In general, the microprojections can have a height of at least about 50 μm, at least about 100 μm, at least about 150 μm, at least about 200 μm, at least about 250 μm, or at least about 300 μm m. In general it is also preferred that the microprojections have a height of no more than about 1 mm, no more than about 500 μm, no more than about 300 μm, or in some cases no more than about 200 μm or 150 μm. The microprojections may have an aspect ratio of at least 3:1 (height to diameter at base), at least about 2:1, or at least about 1:1. A particularly preferred shape for the microprojections is a cone with a polygonal bottom, for example hexagonal or rhombus-shaped. Other possible microprojection shapes are shown, for example, in U.S. Published Patent App. 2004/0087992. Microprojections may in some cases have a shape which becomes thicker towards the base, for example microprojections which have roughly the appearance of a funnel, or more generally where the diameter of the microprojection grows faster than linearly with distance to the microprojection's distal end.

The number of microprotrusions in the array can be at least about 50, at least about 100, at least about 500, at least about 1000, at least about 1400, at least about 1600, or at least about 2000. The area density of microprotrusions, given their small size, may not be particularly high, but for example the number of microprotrusions per cm$^2$ may be at least about 50, at least about 250, at least about 500, at least about 750, at least about 1000, or at least about 1500.

The array of microprotrusions can formed by providing a mold with cavities corresponding to the negative of the microprotrusions, compression molding the mixture of the melted degradable polymer material and viral nanoparticles, demolding the resulting array from the mold.

In some embodiments, it may be desired that the microprojections of the array detach from the array following insertion of the array into skin. Detachable microprojections may be accomplished by a number of approaches. A layered approach, for example, may be used in which the array is composed of multiple layers, and a layer comprising the attachment areas of the microprojections to the array is more readily degradable than other layers. For example, the layer comprising the attachment areas of microprojections to array may be one which is more rapidly hydrated than the other layers.

Alternatively, an array made of a homogeneous material may be employed, in which the material is more readily degradable at lower pH's. Arrays made of such a material will tend to degrade more readily near the attachment points because these, being closer to the surface of the skin, are at a lower pH than the distal ends of the microprojections. (The pH of the skin's surface is generally lower than that of the skin further inwards, pH being for example approximately 4.5 on the surface and approximately 6.5 to 7.5 inward.)

Materials whose solubility is dependent on pH can be, for example, insoluble in pure water but dissolve in acidic or basic pH environment. Using such materials or combination of materials the arrays can be made to differentially biodegrade at skin surface (pH approximately 4.5) or inside skin. In the former, the whole array can biodegrade while in latter the microneedle portion of the array will biodegrade while substrate can be removed away.

Microneedle arrays made of materials with pH dependent solubility may have additional advantages besides facilitating detachment and differential absorption. For example, they may simplify packaging and handling because of their moisture resistance and rapid hydration and bioadhesion in the buffered acidic or basic environment of the skin.

Microprojection arrays may also be made in which the microprojections have a biodegradability which varies with temperature over the range of expected use conditions, for example in the range of about 25° C. to about 40° C. This may be achieved, for example, by the use of thermosensitive or thermoresponsive polymers. For example, PLGA biodegrades more slowly at higher temperatures. Certain Pluronic polymers are able to solidify with rising temperature. A use for the variation of degradability with temperature is, for example, due to the fact that the microprojections when inserted in skin will tend to have their distal ends at a higher temperature than the portions closer to the base, including the portions (if any) which are not inserted into skin and are thus at a temperature closer to the ambient temperature. The use of a temperature-dependent biodegradability thus offers a further way to tailor the biodegradability along the length of the microprojections.

In another embodiment, as described in the examples, the nanoparticle construct can be in the form of a plurality of microparticles that can be formed, for example, from crymilled extruded substrate that includes the virus or virus like particles encapsulated in the degradable polymer matrix. The size of the microparticles can be, for example, about 1 μm, about 10 μm, about 25 μm, about 50 μm, about 100 μm or more. In some embodiments, the size of the particles can be about 1 μm to about 100 μm, or about 10 μm to about 25 μm.

In some embodiments, the nanoparticle construct can used to provide sustained and/or controlled delivery of virus or virus-like particles to a target tissue in a subject. The nanoparticle construct can be in situ delivered and/or administered to the tissue of the subject. Upon delivery and/or administration of the nanoparticle construct to tissue, the nanoparticle construct can degrade and/or erode by, for example, hydrolysis to release the virus or virus-like particles to the tissue. In particular, virus or virus like particles have been shown to preferentially accumulate in diseased tissue, such as cancer tissue or inflamed tissue (e.g., atherosclerotic blood vessels). While not intending to be bound by theory, it appears that viral nanoparticles can be taken up by blood components such as macrophage cells of the immune system, which subsequently accumulate in diseased tissue (e.g., a tumor or atherosclerotic blood vessel), thereby delivering the virus particle to cells at the disease site.

In some embodiments, administering the nanoparticle construct to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Other embodiments described herein relate to methods of treating cancer in a subject in need thereof by administering in situ to cancer of the subject a therapeutically effective amount of the nanoparticle construct, which includes a plurality of virus or virus-like particles encapsulated within a melt processable biodegradable polymer matrix. While not intending to be bound by theory, it appears that the virus particles or virus like particles, such as plant virus or virus-like particles, have an anticancer effect as a result of eliciting an immune response to the cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the nanoparticle constructs are used to treat cancer selected from the group consisting of but not limited to melanoma, breast cancer, colon cancer, lung cancer, and ovarian cancer. In some embodiments, the virus particles are used to treat lung cancer.

In some embodiments, the in situ administration of the nanoparticle construct can be proximal to a tumor in the subject or directly to the tumor site to provide a high local concentration and sustained and/or controlled release of the virus or virus like particles in the tumor microenvironment. The method represents a type of in situ vaccination, in which application of an immunostimulatory reagent directly to the tumor modifies the tumor microenvironment so that the immune system is able to respond to the tumor.

In some embodiments, the method can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step ablating the cancer includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879; Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, the step ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

When used in vivo, the nanoparticle constructs can be administered as a pharmaceutical composition, and a pharmaceutically acceptable carrier. The nanoparticle constructs, or pharmaceutical compositions comprising these constructs, may be administered by any method designed to provide the desired effect. Administration may occur enterally or parenterally; for example orally, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device.

One skilled in the art can readily determine an effective amount of the nanoparticle constructs to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the virus particles to be administered can be estimated from the volume of cancer cells to be killed or volume of tumor to which the virus particles are being administered.

Useful dosages of the nanoparticle constructs can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the nanoparticle constructs can vary depending upon many different factors, including means of administration, target site, physiological state of the patient, whether the patient is human or an animal, other medications administered, and whether treatment is prophylactic or therapeutic.

Advantageously, the nanoparticle construct can provide a slow-release and/sustained formulation of the virus or virus like particles as an in situ vaccine that maintains sustained immune stimulation without the need for repeat injections. The release of the plant virus or virus like particles can be constant and sustained for about 1 day, 2 days, 3 days, 4 days, 5 days, 6 days, 1 week, 2 weeks or more. The constant release can be sustained between subsequent nanoparticle administrations. Maintaining a constant immunostimulatory effect can reduce the number of administrations, enhancing their effectiveness. The release of the virus or virus-like particles having from the degradable polymer matrix can be at least partially defined by the swelling and degradation rate of the degradable polymer material under physiological conditions.

In some embodiments, a dose of the virus or virus-like particles can be coadministered with the nanoparticle construct in situ to cancer of the subject to provide an initial immune response prior to sustained release of the virus or virus-like particles from the nanoparticle construct. These combined strategies can maintain the single administration vaccine nature of the administration of the nanoparticle construct and will likely improve treatment of the cancer.

In still other embodiments, the nanoparticle construct can include degradable polymer matrix and a plurality rod-shaped viral nanoparticles that are encapsulated in the matrix. The rod-shaped viral nanoparticles can be used as carriers to deliver at least one agrochemical agent or ingredient in a controlled and targeted manner for agricultural applications. Rod-shaped plant viral nanoparticles can provide an economically and environmentally viable alternative to conventional synthetic nanoparticles. Plant viral nanoparticles can be produced in large quantities in a short time for a relatively low price. In addition, plant viral nanoparticles are exceptionally robust to the harsh environment of crop fields, biodegradable, as well as biocompatible and noninfectious, making them safe to use on industrial crops.

In some embodiments, a melt processed nanoparticle construct can include a plurality of rod-shaped viral nanoparticles encapsulated in a degradable polymer matrix and at least one agrochemical agent that is conjugated to and/or loaded on and/or within the viral nanoparticles. The rod shaped viral nanoparticle can have an exterior surface and an interior surface that extend from a first end to a second of the rod-shaped viral nanoparticle. The interior surface can define a channel that extends through rod-shaped viral nanoparticle from the first end to the second end. The channel can include the viral genome or lack the viral genome. The agrochemical agent can be conjugated to an interior and/or exterior surface of the viral nanoparticle.

In some embodiments, the viral nanoparticles include Virgaviridae virus particles. In other embodiments, the viral nanoparticles include one at least one viral nanoparticle of the Tobamovirus species. Particular examples include, but are not limited to, tobacco mild green mosaic virus nanoparticles and tobacco mosaic virus nanoparticles.

In other embodiments, the agrochemical agent can be covalently or noncovalently coupled and/or conjugated to the viral nanoparticles or loaded on or within the degradable polymer matrix of the nanoparticle construct. In one example, positively charged agrochemical agents can be non-covalently loaded onto negatively charged interior or exterior surfaces of the rod-shaped viral nanoparticles by electrostatic interactions between the positively charged agrochemical and carboxylate groups of exposed aspartic acid and glutamic acid residues on the interior and exterior surface of the rod-shaped viral nanoparticles prior to melt processing the rod-shaped viral nanoparticles and degradable polymer material. In another example, agrochemical agents can be covalently bound to chemically modified carboxylate groups of exposed glutamic acid, aspartic acid, and tyrosine residues on the interior or exterior surface of the rod-shaped viral nanoparticles.

The agrochemical agent conjugated to the interior and/or exterior surface of the rod-shaped viral nanoparticle can be selected from the group consisting of nematicides, fungicides, herbicides, pesticides, acaricides, rodenticides, plant growth regulators, nutrients, pest repellents, and combinations thereof.

In some embodiments, the nanoparticle constructs can be formulated as a plurality of particles to facilitate delivery of the nanoparticle construct to a pest, plant, plant organ, plant propagation material, or a surrounding area thereof.

Other embodiments described herein relate to a method of treating a plant. The method can include applying a nanoparticle construct as described herein to the plant in a treatment effective amount. Such plants are generally angiosperms or gymnosperms, and in some embodiments are monocots or dicots. In some embodiments, the plant is wheat, corn (maize), soybean, cotton, cassava, potato, sweet potato, bananas, citrus, strawberries, tomato, coffee, carrots, peppers, turf grass, or greenhouse ornamentals, taro, oats, barley, cereal rye, breadfruit, pea, rice, yams, garbanzo (chickpea), Jerusalem artichoke, or lentil.

In some embodiments, the plant may be in the form of a plant part, such as leaves, flowers, stems, roots, tubers, fruits, and seeds.

In other embodiments, the composition is applied in an amount effective to combat nematode parasitism on said plant.

In some embodiments, the nanoparticle constructs including the rod-shaped viral nanoparticles loaded with the agrochemical agent can have greater soil mobility than the agrochemical agent alone. This can provide agrochemical agent loaded rod-shaped VNPs with enhanced penetration through soil to reach pests, such as nematodes, that feed on the roots of plants.

Examples have been included to more clearly describe particular embodiments of the invention. However, there are a wide variety of other embodiments within the scope of the present invention, which should not be limited to the particular examples provided herein.

Example 1

In this Example, we used melt encapsulation to create solid-state poly(lactic-co-glycolic acid) (PLGA) implants laden with Qβ for applications in slow-release vaccine development. Processing parameters relevant to extrusion or injection molding could be tuned to maintain particle integrity post-processing, providing a window for scale up to commercial polymer processing equipment. Of utmost importance, single dose implants perform equivalently to traditional vaccine administration schedules.

Material and Methods
Preparation of PLGA/Protein Implants

Poly(lactic-co-glycolic acid) (PLGA), 8 kDa polyethylene glycol (8 KPEG), and 20 kDa PEG (20 KPEG) were individually ground manually with a mortar and pestle twice, 10 minutes each time, into a fine powder. The PLGA powder consisted of particles with an average length of 185.8±89.1 µm as determined via SEM image analysis. PLGA was mixed with the appropriate weight percent of lyophilized Qβ and PEG (if added) via repeated vortexing in a 2 mL Eppendorf tube. Formulations were as follows with all percentages expressed as a weight percent: PLGA/1% Qβ; PLGA/1% Qβ/10%8 KPEG; PLGA/1% Qβ/10%20 KPEG, PLGA/5% Qβ, PLGA/10% Qβ. Two different custom built aluminum syringe-die were used for melt processing of the blends to minimize material input. Both syringe-die systems consisted of a cylinder with a circular 1 mm exit diameter that was wrapped with heating tape, combined with a digital control element to provide constant heating. The die used for melt encapsulation of samples for in vitro testing utilized polypropylene BD™ LUER LOK™ syringes which were filled with 500-200 mg of the PLGA/Qβ blends and heated at 95° C. as determined by a glass thermometer (99.9° C. average along the temperature profile as determined via an infrared thermometer) for 10 minutes. The melted PLGA/Qβ blend was flowed through the die using a syringe pump with a velocity of 3 mm s$^{-1}$ (~2.35 mm$^3$ s$^{-1}$ volumetric flow rate). The resulting cylindrical implants had diameters ranging from 1.0-1.3 mm. Melt encapsulation of ClearColi® produced Qβ for in vivo testing was performed with a cylinder manufactured to fit polypropylene 1 mL volume Norm-Ject syringes. The die still consisted of a circular 1 mm hole. This barrel was used to minimize materials due to the lower yield of ClearColi® produced particles. The syringe was filled with 50-100 mg of the appropriate PLGA/Qβ blend and extruded in the same method as previously described. There was no difference observed in implant diameter or particle integrity between samples fabricated with different barrels.

Shear Application

Shear application was performed by loading 150-300 mg of PLGA/1% Qβ onto a 25 mm wide parallel plate rheometer at 95° C. Samples were allowed to equilibrate for 5 minutes, then the top plate was lowered to a gap of 0.45 mm and shear rates from 0.1-50 s$^{-1}$ were applied for 3 minutes. The sample was recovered from the rheometer post-shear and the Qβ was recovered and analyzed via the extraction method previously described. The viscosity of the samples was also measured during this process and found to be in the range of 120-130 Pa·s, with an average of 128 Pa·s.

Radius Shear Dependency and Peclet Number Calculations

Qβ samples recovered post-shear application were analyzed via DLS and FPLC. Weight average hydrodynamic radii were calculated from the DLS data for samples subjected to 0.1, 0.25, 0.5, 1, 2.5, 5, 10, 25, and 50 s$^{-1}$. Samples subjected to 25 and 50$^{-1}$ exhibited extensive particle breakup when analyzed via FPLC. The breakup product was assumed to be coat protein dimers, which exhibit a radius of 3.21 nm estimated from the crystal structure (PDB: 1QBE). This estimate is similar to the hydrodynamic radius of green fluorescent protein (2.8 nm), which is of similar molecular weight to the coat protein dimer (27 and 28 kDa respectively). The ratio of intact particles to coat protein dimers was calculated via curve fitting of the two major curves observed in the FPLC. The ratio of intact particles was multiplied by the weight average radius determined via DLS and added to the ratio of coat protein dimer multiplied by 3.21 nm to give an average radius of species in the 25 and 50 s$^{-1}$ samples, as shown by the equation below.

$$R_{Ave}=(R_{Ave,DLS})-(\%_{Particle})+(3.21 \text{ nm})-(\%_{Dimer})$$

Where: $R_{ave}$=average radius for samples subjected to 25 and 50 $s^{-1}$ shear rates $R_{Ave,DLS}$=mass average radius calculated from the DLS result $\%_{Particle}$=percentage of particle calculated from curve fitting of the FPLC $\%_{Dimer}$=percentage of dimer calculated from curve fitting of the FPLC The weight average radius was divided by the weight average radius of Qβ that had been extracted from PLGA/1% Qβ samples that had not been subjected to shear. This result was plotted as the radius of shear applied samples to the initial radius versus shear rate.

This result was non-dimensionalized by calculating the Peclet number for each shear rate. The Peclet number (Pe) is a dimensionless number of the ratio of convective forces vs the diffusive forces in a fluid system. The Peclet number was calculated as the ratio of shear stress applied on the particles over the diffusive forces estimated by the Stokes-Einstein equation, as shown by the equation below.

$$Pe = \frac{6\pi\eta\dot{\gamma}R^3}{k_bT}$$

Where: η=viscosity of the polymer melt (Pa·s)

$\dot{\gamma}$=shear rate applied to the system ($s^{-1}$)

R=weight average radius of the particles before shear application (m)

$k_b$=Boltzmann's constant (J·$K^{-1}$)

T=temperature of the system (K)

The resulting plot of particle radius of shear applied samples to the initial radius versus Peclet number is useful in relating the aggregation behavior of Qβ during melt encapsulation to other polymer systems with different viscosities and processing temperatures.

Shear Application Thermal Analysis Calculations

Mathematical analysis was performed to estimate the total applied energy to the system during shear application and correlate it to the observed particle breakup. Qβ particle breakup into free dimers involves the breakage of disulfide bonds between adjoining dimers on the particle, with each dimer containing 4 disulfide linkages and one particle containing 90 coat protein dimers. The bond dissociation energy of a disulfide bond is typically 251 kJ/mol. Thus, the theoretical energy of all disulfides per particle was calculated to be 45,180 kJ/mole of particle. Integration of the first endothermic peak on the DSC thermogram (from 84 to 172° C.) as shown by the equation below, which is speculated to be disulfide breakup, yielded a value of 43,860 kJ/mol particle in good agreement with the theoretical value.

$$E_{disulfide} = (MW_{Q\beta})\left(\frac{\Delta T}{s}\right)^{-1}\int_{T_1}^{T_2}\left(\frac{W}{g}\right)dT$$

Where: $E_{disulfide}$=total enthalpy of disulfides per mole of particle (J/mol Qβ)

$MW_{Q\beta}$=molecular weight of Qβ=2,556,000 g/mol

ΔT/s=heating rate of the DSC study, 0.333 K/s mW/g=heat flux of the DSC sample per gram (W/g)

The value determined via DSC integration was used to calculate the total disulfide bond energy present based on the mass of Qβ present in each shear application sample. The moles of PLGA in the system was calculated based on the mass of PLGA in the system and an average molecular weight of 12.5 kDa.

The total applied energy to the system during shear application was calculated as the sum of the energy applied by shear stress and thermal energy with the effects of shear heating taken into account utilizing the equations shown below. The energy values were normalized by the total disulfide bond energy present in each sample.

$$E_{shear} = \eta \dot{\gamma} V_{system}$$

$$E_{thermal} = k_b N_A (T_{applied} + \Delta T_{shear})(mol_{Q\beta} + mol_{PLGA})$$

Where: $\eta$=viscosity of the polymer melt (Pa·s)
$\dot{\gamma}$=shear rate applied to the system (s$^{-1}$)
$V_{system}$=total volume of Qβ and PLGA (m$^3$)
$k_b$=Boltzmann's constant (J·K$^{-1}$)
$N_A$=Avagadro's number
$T_{applied}$=temperature during shear application (K)
$\Delta T_{shear}$=temperature increase due to shear heating (K)
$mol_{Q\beta}$=moles of Qβ in the system
$mol_{PLGA}$=moles of PLGA in the system Immunization and ELISA Analysis Prior to immunization studies, 3 male Balb/c mice aged 7 weeks were implanted subcutaneously with ~0.5 cm of neat PLGA cylinder via puncture with a 16 gauge needle and insertion with forceps. The mice were monitored for 4 weeks and exhibited swelling at the site of insertion for 2 weeks after insertion, which subsequently subsided. The mice did not exhibit any adverse health or behavioral response to the implantation of the neat PLGA cylinders. For standard immunization, male Balb/c mice (Charles River) aged 7 weeks (n=5) were immunized 3 times on days 0, 14, and 28 with 50 μg Qβ in 100 μL sterile PBS through subcutaneous injections behind the neck using a 29G insulin syringe. The Qβ was produced in ClearColi E. coli cells that contain a modified lipopolysaccharide (LPS) outer membrane that does not elicit an immune response in mice. Blood (~100 μL) was drawn prior to the first immunization and on a weekly to biweekly basis via the retro-orbital plexus using heparinized capillary tubes and collected in Greiner Bio-One VACUETTE™ MiniCollect™ tubes. Serum was separated by centrifuging blood samples at 14,800 rpm, 4° C., for 10 min and stored at 4° C. until analyzed via enzyme-linked immunosorbent-assay (ELISA). For implant immunization, male Balb/c mice (Charles River) aged 7 weeks (n=5) had 0.5 cm (~8 mg) of PLGA/10% Qβ inserted into the subcutaneous space on the neck via puncture with the tip of a 16 gauge needle and insertion with forceps. The amount of implanted material was chosen to deliver roughly the same amount of Qβ over the first 28 days as the mice immunized via subcutaneous injection based on the in vitro release profile, with ~0.8 mg of implant correlating to ~150 μg of released Qβ over 30 days. Orbital bleeds were conducted as previously described on the same days as the standard immunization schedule mice. All mice were boosted at day 65 with 50 μg of Qβ. After day 75, all mice were euthanized and the subcutaneous space was examined. No implant material was present in any of the implanted mice and no extensive scar tissue was present compared to non-implanted mice.

The anti-Qβ IgG response was measured by first coating Nunc Maxisorp 96-well plates with 2 μg of Qβ in 200 μL of sterile PBS, pH 7.4 at 4° C. overnight. The wells were then blocked with 200 μL of blocking buffer (2.5% w/v dry milk, 25% neonatal calf serum in PBS, pH 7.4) at 37° C. for 1 hour. The wells were then incubated with mouse sera at dilutions from 1:100 to 1:1000000 in 100 μL blocking buffer for 2 hours at 37° C. The wells were then incubated with 100 μL of a 1:1000 dilution in blocking buffer of alkaline-phosphatase labeled goat anti-mouse IgG for 1 hour at 37° C. The wells were washed between each incubation step using 3×250 μL of 0.1% w/v Tween-20 in PBS, pH 7.4. The wells were developed using 100 μL of 1-step PNPP substrate at 4° C. for 10 minutes. The reaction was stopped with 100 μL of 2 M NaOH and the absorbance was read at 405 nm in triplicate for each sample. The end-point titer value was determined by comparison to a statistically defined cutoff value based on the pre-bleed measurements of 10 mice and a confidence level of 99%. Values are expressed as the average and standard deviation of 5 mice.

Murine anti-Qβ IgG subtypes were determined via the ELISA method described above with alkaline-phosphatase labeled goat anti-mouse IgG1, IgG2a, and IgG2b used for detection. Percentages are expressed as the average and standard deviation of 5 mice.

Poly(lactic-co-glycolic acid) (EXPANSORB® 10P019, 50:50 PLGA, inherent viscosity 0.15-0.25 dlg$^{-1}$, 5-20 kDa) was purchased from PCAS. Potassium phosphate monobasic anyhdrous, potassium phosphate dibasic anydrous, sodium phosphate dibasic hetptahydrate, Gibco 1×PBS pH 7.4, butanol, Miller LB Broth, D-sucrose, guanidine hydrochloride, sodium dodecyl sulfate, and isopropyl β-D-1-thiogalactopyranoside, kanamycin, spectinomycin, sodium azide, ethyl acetate, neonatal calf serum, 1-step PNPP substrate, Tween-20, albumin standard, and sodium hydroxide were purchased from Fisher Scientific. Poly(ethylene glycol) ($M_n$=20000) was purchased from Alfa Aesar. Poly(ethylene glycol) ($M_n$=8000) was purchased from Amresco. Bradford reagent was purchased from VWR. Goat anti-mouse IgG-alkaline phosphatase antibody was purchased from Life Technologies. Goat anti-mouse IgG2a, IgG2b and IgG1-alkaline phosphatase antibodies were purchased from Novus Biologics. All reagents were used directly, without further purification.

Results

Qβ VLPs were expressed recombinantly in E. coli and purified with typical yields of ~50-100 mg per liter of culture. Chromatographic analysis verified the purity as a single peak in the size-exclusion chromatogram with no aggregates, free protein, or free RNA present (FIG. 2A). The purified VLPs exhibited a hydrodynamic radius of ~15 nm determined by dynamic light scattering (DLS) and verified by transmission electron microscopy (TEM). TEM analysis yielded an average radius of 13.2 nm determined via image analysis (FIG. 2B, 2C). The smaller radius observed in the TEM micrographs is a result of dehydration during TEM preparation versus the hydrodynamic radius measured by DLS. The VLPs were dialyzed into deionized water and lyophilized to yield a fluffy white powder. Resuspension of the powder into PBS and analysis by DLS and fast protein liquid chromatography (FPLC) indicated that lyophilization yielded no negative effect on Qβ and did not result in the formation of aggregates or disassembly of the particles.

Dynamic scanning calorimetry (DSC) of Qβ was conducted to determine thermal transitions that may occur in the processing window for PLGA. The DSC thermogram of the freeze-dried Qβ yielded two endothermic peaks, at 130 and 236° C. respectively. The peak at 130° C. was attributed to the break-up of the disulfide bonds that stabilize coat protein dimers in the icosahedral Qβ structure. Disulfide bond dissociation has been observed in the range of 80-160° C. in solid-state rubber vulcanization and self-healing materials. The endothermic peak at 236° C. can be attributed to the dissociation of coat protein dimers and denaturation of the coat proteins. Previous DSC studies of lysozyme, glycinin, and human growth hormone in the solid-state have indicated protein denaturation over temperature ranges of 180-200° C. The higher denaturation temperature observed with lyophilized Qβ was likely due to strong intermolecular attractions associated with dimer stability. The DSC study of Qβ provided insight into the denaturation process during heating in the solid state and ensured that no major denaturation processes occurred in the processing window of 80-100° C. typically used for melt-encapsulation of proteins with PLGA.

Qβ laden implantable polymeric materials were manufactured via melt-encapsulation with PLGA utilizing a lab-built syringe-die extrusion device (FIG. 1). The syringe-die extruder allows for melt-processing of material amounts as low as 100 mg. This provides access to laboratory-scale experiments since commercial small scale extruders require a minimum of 5 grams for effective processing. The low amount of material required makes this a valuable tool for pilot-scale experiments using high-value materials for initial testing. PLGA and Qβ powders were combined and vortexed repeatedly to homogenize the mixture. The mixture was then loaded into a syringe, placed in the extrusion device at 95° C. for 10 minutes, and then pushed through a 1 mm cylindrical die to yield cylindrical opaque materials. The DSC thermogram of PLGA indicated a glass transition temperature of 37° C. with a small melting endotherm at 41° C. The processing temperature was the lowest that gave the most homogenous cylindrical shape, with no observable aggregated portions of Qβ powders along the length of the extruded material. PLGA materials loaded with 1, 5, and 10 w/w % Qβ were prepared via this method.

Following implant fabrication, Qβ was extracted to determine particle integrity, aggregation state, and capsid disassembly. Extraction of Qβ processed at 1 wt % was performed utilizing ethyl acetate to dissolve the polymer and the remaining Qβ was resuspended in PBS. Treatment of lyophilized Qβ with ethyl acetate and resuspension yielded no aggregated or disassociated species. Qβ extracted after melt-encapsulation was recovered at ~90% and analyzed via DLS and FPLC (FIGS. 2D and 2E). DLS and FPLC both indicated the formation of small amounts of aggregated species after melt-encapsulation. The aggregated species apparent in the DLS histogram span from ~30 to 70 nm in radius, indicating small-scale aggregated clusters of 2 to 5 VLPs. The DLS data was plotted as a mass percentage to better represent the proportion of aggregated species as percent intensity skews toward larger species. The aggregates made up ~16% of the recovered VLPs calculated from the mass percentage distribution. The peak at 10 mL retention volume in the FPLC chromatogram appeared at the void volume of the column with all aggregated species eluting at this volume. Curve fitting and integration of the FPLC curves yielded a relative percentage of 12% aggregated VLPs. Minor peak broadening was observed in the portion of the curve corresponding to dispersed Q. Both DLS and FPLC analysis yielded similar values of aggregated species and indicate roughly 85% of VLPs remain dispersed and intact after melt-encapsulation with PLGA at 95° C. TEM further verified that the particles retained their characteristic icosahedral shape after melt-encapsulation and the radius determined via image analysis was 13.3 nm, in good agreement with the size determined via TEM prior to melt-encapsulation (FIG. 1F).

The dispersion of Qβ within the PLGA matrix in the solid state was explored through elemental mapping using energy dispersive X-ray spectroscopy coupled with scanning electron microscopy (EDS-SEM). Aggregation and segregation of proteins within the polymer matrix can occur during melt-processing, resulting in regions of protein rich and protein poor areas through the cross-section of the material. This poor dispersion of protein can result in irreversible aggregation and denaturation, as well as an inconsistent release profile due to burst release when the aggregated regions are exposed to solvent during matrix degradation. All of these factors would negatively affect the desired properties of the Qβ/PLGA materials, thus the effect of loading level on the dispersion of Qβ within PLGA in the solid state was studied to ensure the particles were properly dispersed throughout the matrix. EDS-SEM was a valuable tool for studying dispersion, as it allowed for the visualization of distinct elemental signals through a cross-section of material. SEM images of the freeze-fractured cylindrical materials were obtained and the distribution of the EDS sulfur K-series signal throughout a 12.5×12.5 μm cross-section was obtained (FIG. 3). The sulfur K-series signal was chosen for EDS analysis since it is unique to the protein component in the implant. Qualitative assessment of mapping from neat PLGA indicated very little background signal. The mapping of PLGA loaded with 1, 5, and 10% Qβ resulted in good qualitative dispersion and no segregation of sulfur poor and rich regions. The number of spots corresponding to sulfur signal does not increase proportionately to the loading level, however the color intensity of the spot is dependent on the amount of sulfur in the system. Signal thresholding of the images to 50% of maximum signal yielded images that more clearly show the increase in sulfur signal in response to increased loading levels. Furthermore, the quantitative sulfur signal from the EDS spectrum was 0.08, 0.33, and 0.82 wt % for loading levels of 1, 5, and 10 wt %, respectively, indicating that sulfur content caries proportionally with loading level. Quantitative dispersion analysis was performed utilizing ImageJ to determine the cumulative distribution function (CDF) of particles based on the nearest neighbor and point-to-point distance analysis. The CDF gives the probability that a particle-particle distance is equal to or less than the distance on the plot. The nearest neighbor and point-to-point distance cumulative distributions followed similar profiles for all loading levels. The nearest neighbor analysis gave relatively small values for nearest neighbor distance, with 75% of the particles having a nearest-neighbor less than 0.5 μm away. The linearity of the point-to-point distance plot is also indicative of the particles being well dispersed, as the distance of the points away from each other would increase sporadically if they were aggregated into clusters. Overall, loading levels of 1, 5, and 10 wt % Qβ did not form aggregated regions within the PLGA during melt-encapsulation based on the qualitative and quantitative results. This result indicated that Qβ can be melt-encapsulated at 1, 5, and 10 wt % with PLGA without aggregation within the matrix, ensuring that the release of Qβ from the matrix will not be adversely effected and will be replicable.

Qβ VLP laden cylindrical polymeric devices were successfully manufactured via melt-encapsulation and the VLPs maintained particle integrity following extraction. However, most commercial manufacturing processes for polymer nanocomposites typically follow a two-step process; a masterbatch of the composite is compounded followed by geometric molding. The syringe extrusion process described above is representative of the initial compounding step in the manufacturing of polymeric nanocomposites. Next, we sought to evaluate how VLP integrity in the masterbatch could be maintained in downstream processes such as extrusion, injection molding, or compression molding. All of these processes introduce the composite to similar stress forces, namely pressure and shear forces. Thus, the cylindrical Qβ/PLGA material was subjected to a melt-press, to simulate pressure, or to shear application using a rheometer. The 1 wt % loaded samples were utilized for post-processing studies as they could be produced in the highest amount due to the lower amount of Qβ needed for material processing.

Typical compression molding is performed by pumping material into a cavity at high pressures for a set amount of time to mold the material into the desired shape. The pressures and times range depending on the polymer, mold, and desired device properties, but generally a pressure range of 500-2000 psi and cycle times of 2-5 minutes are utilized. A melt-press was used to apply a pressure of 1200 psi for 5 minutes at 95° C., an intermediate range for compression molding. The melt-pressed and extracted VLPs were analyzed via DLS and FPLC to determine the integrity and aggregation state of extracted and recovered Q (FIG. 4). The resulting DLS histogram indicated an increase in both the amount and size of aggregated particles. Aggregates in the range of 40 to 100 nm radius were observed in the DLS data, corresponding to systems of 3 to 7 particle aggregates. The percentage of recovered VLPs that were aggregated was 25.5%, an increase of ~10% from the initial melt-encapsulation step. The FPLC chromatogram of the recovered Qβ indicated the presence of aggregates and intact particles with peak maxima at 10 mL and 18 mL respectively. The peak centered at 18 mL had considerable broadening towards lower retention volume. A minor tail was observed at higher elution volumes indicating some particle breakup, however this was negligible compared to the remainder of the population. Relative integration of curves fit at 10 mL and 18 mL resulted in 13% of the recovered particles being aggregated. The discrepancy between the percentage of aggregated species between the DLS and FPLC is a result of the curve in the FPLC not being a true Gaussian curve, thus skewing the curve fitting result. The simulated compression molding conditions resulted in a modest increase in aggregated species from initial melt-encapsulation (~10%) and the majority of Qβ remained as single dispersed particles, demonstrating this system can be suitable for processing via compression molding.

A rheometer was used to apply different shear rates to 1 wt % Qβ loaded PLGA to emulate the shear effects applied during post-processing steps. The range of shear rates chosen were from 0.1-50 s$^{-1}$, which correlated to processes with relatively low applied shear. This range is most commonly used in compression molding, blow molding, and 3D printing processes and relevant in conditions the Qβ/PLGA material would be under during production of more complex architectures for implantation. Shear was applied utilizing a rheometer with a parallel plate configuration for 3 minutes at 95° C. and Qβ was recovered via ethyl acetate extraction. The DLS and FPLC results of Qβ after application of shear rates from 0.1-50 s$^{-1}$ indicated a three-phase response to increasing shear rates. (FIG. 5). The lowest shear rates from 0.1-1 s$^{-1}$ resulted in an increase in both the size and amount of aggregates in the recovered VLPs in response to increasing shear rate. Further increase in applied shear rate to 2.5-10 s$^{-1}$ diminished the size and amount of aggregates observed. Increasing the applied shear rate to 25 and 50 s$^{-1}$ yielded no observable aggregates in the DLS histogram. Analysis of the recovered Qβ via FPLC indicated the same trend observed with DLS and the intensity of the aggregate peak at 10 mL increased relative to the Qβ peak at 18 mL after application of shear rates from 0.1 to 1 s$^{-1}$.

FPLC chromatograms of samples subjected to shear rates from 2.5 to 10 s$^{-1}$ were also in good agreement with the DLS results, with the aggregate peak diminishing in intensity as the shear rate increased. All samples subjected from 0.1 to 10 s$^{-1}$ exhibited some degree of disassociated species eluting at higher retention volumes. These species likely consist of partially disassociated VLPs, free coat protein dimers, and free RNA. Thus, any application of shear to the samples appears to result in a degree of disassociation of Qβ, however these are all relatively minor when compared to the aggregates and single particles based on the peak area observed in the FPLC. As shear rates approached 10 s$^{-1}$, a significant reduction in particle aggregates is observed and the chromatograms show predominately intact particles. Finally, as the shear rate continues to increase to 25 and 50 s$^{-1}$ extensive capsid dissociation is seen, as evidenced by the predominant peak at 23.2 mL in the FPLC. Curve-fitting and relative integration of the FPLC curves yielded values of 35% and 22% of particles maintaining integrity after application 25 and 50 s$^{-1}$ shear rates respectively. The disassociated species were not observed in the DLS data as the estimated radius of ~3 nm, based on the crystal structure, falls below the limit of detection for the instrument. The particle break-up observed at 25 and 50 s$^{-1}$ indicate that care must be taken in applying higher shear rates to the Qβ/PLGA material. Processes such as twin-screw extrusion and injection molding often have shear rates above 100 s$^{-1}$, which would not be suitable for this system. However, these limitations could be overcome with slower screw speeds during extrusion to maintain shear rates in the acceptable range to retain particle integrity.

It was evident from the DLS and FPLC analysis that the aggregation state and integrity of Qβ within PLGA is dependent on the shear rate applied during melt-processing. As such, we sought to derive a physical model to determine particle stability versus aggregation state in varying shear environments. The mass average radius of all species in the recovered VLPs was estimated from the DLS distribution for samples at shear rates from 0.1 to 10 s$^{-1}$. Shear rates of 25 and 50 s$^{-1}$ cause extensive particle breakup, with the disassociated particles unable to be measured via DLS due to the lower limits of detection. Thus, the radius average for the 25 and 50 s$^{-1}$ samples was estimated using the DLS radius for intact particles and the radius of 3.2 nm for coat protein dimer using a globular estimation of the coat protein dimer from the crystal structure. These two values were averaged using the percentage of intact particle and coat protein dimer estimated from the relative integration of the FPLC curves. The averaged radii were normalized by the average radius of Qβ recovered before the application of shear ($<R>/<R_o>$) and plotted versus the applied shear (FIG. 6A, top axis). The resulting plot demonstrated a clear dependence of particle aggregation and disassociation on applied shear rate. The average particle size increases to 3 times the initial radius with increasing shear rate, with a maximum reached at 1 s$^{-1}$. Processing particles at shear rates greater than 1 s$^{-1}$ causes a return to the initial radius, until a critical shear rate of 25 s$^{-1}$ was reached where particle dissociation occurred. This information is useful for designing post-processing conditions for Qβ laden PLGA materials, however the trend in aggregation state observed is only applicable to this polymer system.

The shear rate relationship was transformed into a Peclet number relationship to expand the utility of the data to processing Qβ with other polymer systems and at differing temperatures (FIG. 6A, bottom axis). The Peclet number is a dimensionless number that represents the ratio of convective forces to diffusive forces. The convective forces are dependent on the shear rates applied and the diffusive forces are dependent on the Brownian motion in the system. This allowed for the estimation of shear forces based on the viscosity of the melted system, the shear rate, and the volume of the system. The Brownian forces were estimated by the Stokes-Einstein equation, which is directly dependent on temperature. Conversion of the aggregation state relative to the Peclet number generalizes the relationship and allows for the estimation of aggregation state in other shear dependent processes. Understanding the aggregation state in response to the applied shear, polymer viscosity, and temperature allows for the calculation of relevant processing conditions without extensive scouting experiments. Thus, the relationship derived from the shear rate application, aggregation states, and Peclet number will allow for the determination of processing conditions to create materials with minimal aggregation and particle break-up for other polymer systems and temperatures. In this case, Peclet values between ~5 and 25 resulted in well dispersed single nanoparticles without dissociation, providing a baseline value for translation to alternative systems.

The stability of Qβ during melt-processing is theorized to be due to the highly interconnected network of disulfide bonds that link coat protein dimers together, forming a thermally and chemically stable covalently attached assembly. The extensive particle break-up observed in samples subjected to 25 and 50 $s^{-1}$ shear rates was hypothesized to be a result of the disassociation of disulfide linkages stabilizing adjacent coat protein dimers. The total energy applied to the system from thermal and shear stress sources was estimated and compared to the total energy of disulfide bonds present to validate this theory. The peak at 130° C. from the DSC thermogram was integrated to yield a total disulfide bond energy of 43,860 kJ per mol of particle, assuming the peak centered at 130° C. corresponded to disulfide bond breakage. Theoretical calculation of the total disulfide bond energy per particle using the bond enthalpy of a disulfide bond yielded a value of 45,180 kJ/mole, in good agreement with the DSC result; further validating the peak assignment of 130° C. as disulfide bond breakage. Therefore, the amount of disulfide bond energy in each sample was calculated using the value derived from the DSC peak integration and the amount of Qβ present in each sample. The energy derived from the shear and thermal effects during shear application was calculated and normalized by the disulfide bond energy per sample for comparison. The resulting plot clearly shows that the energy contribution of the shear stress does not greatly affect the system until shear rates of 25 and 50 $s^{-1}$ (FIG. 6B). The thermal energy present in the system is always 20% below the disulfide bond energy by these calculations, and remains constant for all samples. The shear energy increase observed only with 25 and 50 $s^{-1}$ and subsequent increase in total applied energy relative to the total disulfide bond energy in the system support the conclusion that the higher shear rates result in disulfide bond disassociation between dimers.

After the validation and analysis of the effect of processing conditions on VLP integrity, the effects of loading level and additives on cylindrical materials containing Qβ was studied to determine how Qβ would release from the implant in vitro. Understanding the release properties in vitro was important in designing an optimal system for in vivo implantation that would release appropriate amounts of VNP to elicit an immune response without excessive burst release phases or extremely slow release. All of the samples studied were manufactured via melt-encapsulation with the syringe-die extrusion device and used without any further post-processing. First, PEG additives were utilized to determine the effect on release of Qβ from 1 wt % loaded samples prepared via syringe-die melt-encapsulation. Samples loaded with 1 wt % Qβ did not demonstrate any burst release and had a significant lag period over the first 15 days (FIG. 7A). The first 15 days of release from PLGA materials corresponds to the initial swelling and induction phase, where the polymer matrix swells and minimal hydrolysis of the polymer occurs. The lowest loading level of Qβ exhibited a significant delay in release, likely due to the VLPs remaining within unswelled regions of PLGA until the matrix begin to degrade. Release begins after 15 days as the polymer degrades and erodes, allowing for the Qβ to diffuse out of the matrix into the surrounding. This process continued until day 80 when the material had degraded into small pieces in solution. The total amount of protein released was ~62% of the total amount present. PEG additives were added during the melt-encapsulation process to accelerate the release, as PEG is a known porogen for PLGA materials. Upon hydration of the material, PEG will diffuse into the aqueous media rapidly leaving behind voids through which Qβ can diffuse. Two PEG molecular weights were used (8 and 20 kDa) to avoid negative immune responses in vivo and to keep the molecular weight of the porogen in the same range as PLGA. Both PEG molecular weights were manufactured at 10 wt % loading levels and resulted in a burst release of Qβ during the initial swelling. The Qβ release was increased over the induction phase from day 10 to 30 as the VLPs were able to diffuse more readily through the matrix as porosity was increased by PEG. Matrix erosion started after day 30 and the remaining Qβ was released rapidly as a result of oligomeric PLGA species diffusing more rapidly from the matrix. No significant difference was observed between 8 and 20 kDa PEG additive (FIG. 7A). PEG sizes from 10 to 20 kDa exhibit hydrodynamic radii of 3 to 3.5 nm, thus the small difference in hydrodynamic size between 8 and 20 kDa PEG results in the minimal differences seen in release profiles. Nonetheless, either PEG additive greatly accelerated the release rate of Qβ and had no negative effect during processing.

Loading level is known to influence the release profile from protein-laden PLGA materials, thus the effect of loading for PLGA samples containing 1, 5, and 10 wt % Qβ was studied. Increasing the loading level to 5 and 10 wt % Qβ increased the amount released over the swelling and induction phase by 10% compared to 1 wt % Qβ samples (FIG. 7B). Furthermore, the release after the initial burst was relatively linear for both loading levels. After matrix erosion started, the release increased dramatically and all samples followed a similar release profile regardless of loading level. The increased loading levels of 5 and 10 wt % had little effect on the matrix erosion phase, which is hypothesized to be due to the small size of the VLPs not greatly increasing the void size after diffusion out of the matrix. The void size allowing for oligomeric PLGA diffusion would control the speed at which the matrix erodes, and the loading levels explored did not appear to affect this greatly enough to influence the overall release profile. All samples broke down into small pieces in solution at 80 days and had similar final cumulative release levels. FPLC analysis of samples collected at the 2 and 50-day time points released from implants loaded with 10% Qβ indicated good stability throughout the release process with minimal increase in particle aggregation or break-up.

The in vitro release of 10 wt % Qβ loaded PLGA was studied in release medium with varying ionic strengths to determine how interparticle and particle-polymer interactions effect release behavior. Increasing the ionic strength by increasing the molarity of NaCl has previously been shown to increase the release of lysozyme from PLGA microspheres through disruption of ionic interactions between carboxylic acid moieties in PLGA and the cationically charged lysozyme. The release of Qβ from the PLGA implants exhibited a clear dependence on ionic strength, with decreasing amounts released in response to higher concentrations of NaCl. Qβ exhibits a negative zeta potential at pH 7.4, indicating that under the release conditions the particles would exhibit an overall negative charge. Therefore, increasing salt concentration would shield the negative charges on both Qβ and PLGA and decrease repulsion between both adjacent Qβ particles and Qβ with PLGA. The decrease in ionic repulsion due to charge shielding would result in closer association and aggregation between particles; a similar result has been previously observed in surface adsorption studies of Qβ. The increase in ionic strength has also been thought to slow release by decreasing PLGA swelling via charge shielding. We speculate this would result in a "jamming" effect of particles as they diffuse out of the polymer matrix through water filled pores and channels, slowing the release and resulting in the observed decrease in release rate with increasing ionic strength.

The release samples at all ionic strengths were then incubated sequentially with buffered solutions of 1 M NaCl, 5 M guanidine hydrochloride (GnHCl), and 5 mM sodium dodecyl sulfate (SDS) to determine the factors resulting in the observed incomplete release of Qβ. The addition of 1 M NaCl did not result in any further significant release of Qβ, indicating that ionic interactions do not play a major role in unreleased Qβ, which is consistent with the decreasing release of Qβ in response to increasing ionic strength. Further incubation with 5 M GnHCl, which would disrupt non-covalent aggregates of Qβ, resulted in an increase in released Qβ for all samples with higher ionic strength samples exhibiting higher amounts of released protein. This result indicated that non-covalent aggregation of Qβ is a factor in particles remaining entrapped within the polymer matrix and that high ionic strength release medium results in more aggregation between particles. The final incubation with SDS would break-up any aggregates not disrupted via GnHCl incubation and Q adsorbed on PLGA. The results of SDS incubation released an additional 42-53% of Qβ, indicating a significant amount of Qβ remained within the polymer matrix due to adsorption onto the polymer. This amount was nearly the amount of Qβ remaining from the previous release study and all samples reached approximately full cumulative release after incubation with SDS. Based on this release study, the incomplete release of Qβ was predominately due to adsorption of Qβ onto the polymer. Non-covalent aggregates of Qβ were formed more readily with increasing ionic strength, based on the release observed with GnHCl, owing to charge shielding. These factors in the incomplete release of Qβ are common issues observed in the release of proteins from PLGA systems. While in vitro release studies are important to understand how the release of Qβ is influenced by different factors after melt-encapsulation, the behavior of PLGA materials in vivo is much more complex due to multitude of enzymes, chemicals, and fluid dynamics present.

PLGA materials laden with Qβ were then utilized to assess their performance to stimulate a humoral immune response in a murine model; we tested whether a robust IgG response was generated against Qβ after melt-encapsulation and release. The subcutaneously implanted Qβ laden devices were evaluated alongside a subcutaneous immunization schedule of 50 μg Qβ injected 3 times biweekly (FIG. 8A). Control implantation of neat PLGA cylinders indicated mild swelling over the first 2 weeks, with mice exhibiting no other adverse health or behavioral conditions. The amounts injected and schedule were based on previous studies utilizing VLPs displaying antigen epitopes without adjuvants to successfully generate humoral immunity in mice. PLGA loaded with 10 wt % Qβ was utilized for the immunization studies and mice were implanted with 0.5 cm (~8 mg) of 1 mm cylindrical material. The amount of implanted material correlated to ~150 μg of released Qβ over 30 days based on the in vitro release profile, delivering roughly the same amount of Qβ over the first 28 days as the mice immunized via subcutaneous injection. Consistent levels of anti Qβ-IgG titers were observed over 65 days and the booster administration lead to a successful increase in IgG levels, as expected. Overall, the Qβ vaccine implant matched the IgG titer profile compared to a contemporary repeat-administration schedule using soluble Qβ. The resulting titers seen were also consistent with previous studies using VLPs to immunize with the same vaccination schedule. This demonstrates that the VLP delivery systems manufactured via melt-encapsulation can potentially eliminate the need for multiple injections for immunization and that the VLPs maintain the integrity of the surface epitopes after melt-encapsulation.

Different subtypes of IgG are indicative of different mechanisms of immune system activation, hence the subtypes of anti-Qβ IgG were determined at day 49, for both the implanted and injected animals (FIG. 8B). In the future, the Qβ/PLGA platform is envisioned as a single administration cancer immunotherapy. Both immunization methods generated predominately IgG2a, which has a high binding ability of FCγ receptors and mediates the antibody dependent cell cytotoxicity (ADCC) of cancer cells by neutrophils. This is important when exploring Qβ as a cancer vaccine candidate, as this pathway is necessary to utilize the immune response to prevent cancer. IgG1 was the second most predominate species for both immunization methods and is involved in complement fixation and the ADCC by natural killer cells. IgG2b was a minor fraction of both IgG pools and serves a similar function as IgG2a. The ability of melt-encapsulated Qβ to generate a statistically identical IgG subtype profile when compared to injected Qβ further validated the implanted material as an alternative delivery vehicle for VLPs.

Melt-encapsulation was a viable method to create polymeric materials laden with Qβ particles. Qβ maintained integrity with minimal aggregation after processing at 95° C. and withstood emulated post-processing conditions of compression molding and extrusion/injection molding. The relationship of Qβ aggregation to shear rate was non-dimensionalized to be applicable to other polymer systems and processing conditions. The addition of PEG and increasing loading level increased the amount of Qβ released over time and the materials prepared were able to sustain Qβ delivery over an 80 day period in vitro. PLGA materials loaded with 10 wt % Qβ were able to generate the same levels of anti-Q IgG relative to a 3 injection immunization schedule in vivo. Furthermore, the IgG subclass types generated were present in the same percentages between mice immunized via implantation or injection. The IgG subclasses generated are identical to injections with boosts, providing confidence that the Qβ delivery system can be expanded to include a variety of vaccination targets. These results demonstrate that VLPs can be successfully melt-encapsulated with PLGA and maintain structural integrity and biochemical signature to affect the immune system in vivo.

Example 2

Polymeric Microneedle Arrays

In Example 1, the viral nanoparticle Qβ was successfully incorporated into PLGA materials via melt processing and was effective as a single administration vaccine device. Anti-Qβ antibodies were generated after implantation of the Qβ/PLGA material and the subtypes of IgG indicated the immune response was the same as that of mice immunized with repeat administrations of Qβ solutions. While Qβ/PLGA material was effective for vaccination, the implantation of solid polymeric materials can be invasive and difficult in a clinical setting. One solution to this administration limitation with materials containing vaccines is microneedle arrays that administer vaccines through the skin. The administration of vaccines into the skin is highly effective due to the dermis containing dendritic cells, keratinocytes, T-lymphocytes, leukocytes, and a multitude of other cells necessary for mediation of an adaptive immune response. Transdermal administration of vaccines has been attempted, however it is limited to hydrophobic low molecular weight antigens that can cross the epithelial layer.

To overcome this, micron-sized needles that penetrate through the outer layer of skin into the dermis were developed. These microneedles ranged in the size of 50 to 1000 μm in length and can be conical or pyramidal in shape with diameters as small as 1 μm. We developed biodegradable PLGA based dissolving microneedle arrays due to PLGA being used in FDA devices and serving as the basis for several developed microneedle systems. Many vaccines are unable to withstand the temperature and time required for melt molding; however, we have previously shown that the viral nanoparticle Qβ can withstand temperatures necessary for melt molding with PLGA and effectively serve as a vaccination agent upon release. Therefore, PLGA/Qβ composites that were prepared via melt processing were further melt molded using silicone microneedle molds into microneedle arrays. The aggregation state, biochemical signature, and ability of Qβ to be administered in a porcine skin puncture model after molding into a microneedle array were determined as well as the morphology and strength of the microneedle array.

Materials and Methods

Materials

Poly(lactic-co-glycolic acid) (EXPANSORB® 10P019, 50:50 PLGA, inherent viscosity 0.15-0.25 dlg$^{-1}$, 5-20 kDa) was purchased from PCAS. Potassium phosphate monobasic anhydrous, potassium phosphate dibasic anhydrous, sodium phosphate dibasic hetptahydrate, Gibco 1×PBS pH 7.4, butanol, Miller LB Broth, D-sucrose, sodium azide, sodium chloride, ethyl acetate, PNPP tablets, Tween-20, albumin standard, chloroform, n-butanol and sodium hydroxide were purchased from Fisher Scientific. α-cyanohydroxycinnaminic acid was purchased from Sigma-Aldrich. Poly (ethylene glycol) ($M_n$=8000) was purchased from Amresco. Bradford reagent was purchased from VWR. Dry milk was purchased from LabScientific Inc. Uranyl acetate 2% solution was purchased from Electron Microscopy Sciences. PLGA-FPI749 was purchased from Akina Inc. Goat anti-mouse IgG-alkaline phosphatase and were purchased from Life Technologies. Cy5-NHS dye was purchased from R&D systems. All reagents were used directly, without further purification.

Instrumentation

Fast protein liquid chromatography (FPLC) was performed using a GE Healthcare AKTA-FPLC 900 chromatography system equipped with a Sephacryl 1000 SF 10/300 size exclusion column. For all FPLC experiments, the mobile phase was 50 mM phosphate buffer, with 150 mM NaCl (pH 7.4) at a flow rate of 0.4 mL/min. Samples were injected at a concentration of 0.1-0.75 mg/mL and the resulting chromatograms were normalized by the maximum absorbance at 260 nm. Dynamic light scattering (DLS) experiments were performed on a Wyatt DynaPro NanoStar DLS instrument. Samples were analyzed at 25° C. in plastic disposable cuvettes with a path length of 10 mm. Transmission electron microscopy (TEM) was performed on a FEI Technai TF30 ST microscope. Negative stained TEM samples were mounted on 400 mesh hexagonal copper grids bearing Formvar support film, stained with 2% uranyl acetate solution, and allowed to dry for 12 h. Microplate measurements were taken with a Biotek Synergy HT microplate reader. Centrifugation was performed with an Eppendorf 5424 centrifuge. Ultracentrifugation was performed with a Beckman Coulter Optima L-100 XP ultracentrifuge. Scanning electron microscopy was performed using a JEOL-6510LV scanning electron microscope at 1 kV. Compression testing was performed using a MTS Insight Electromechanical Testing system with compression attachments and a 5 kN load cell. Mass spectra were collected using a Bruker Autoflex III MALDI-TOF-TOF mass spectrometer with a 200 Hz Smartbeam II laser system and an α-cyanohydroxycinnaminic acid matrix. Fluorescent images of the porcine skin puncture site were collected with a CRi Maestro fluorescent imaging system with a yellow filter set (576-621 nm excitation, 635 low pass emission filter). Confocal images were collected using a Leica TCS SPE microscope with a 635 nm solid state laser.

Qβ Expression and Purification

Qβ was prepared based on the protocol described in the previous Example. A frozen glycerol stock of chemically competent BL21(DE3) E. coli cells transformed with pET28CP (containing the Qβ coat protein sequence) in lysogeny broth (LB) media containing kanamycin (50 μg/mL) was thawed and 1 μL was added to 100 mL of autoclaved selective LB media and grown to saturation for 12 h at 37° C. A total of 10 mL of culture was then diluted into 1000 mL of freshly prepared selective LB media. Culture growth was monitored by optical density at 600 nm (OD600). When the OD600 of the cultures reached approximately 0.8 (mid log phase), protein expression was induced with the addition of 10 mL of 100 mM IPTG, giving a final IPTG concentration of 1 mM. Shaking was continued at 37° C. for an additional 6 h, at which point cells were collected by centrifugation in an Eppendorf A-4-81 rotor at 4000 rpm (4° C.) for 30 min. The supernatant was decanted, and the cell pellet was frozen at −80° C. until purification. Cells were then resuspended in ~100 mL of PBS, pH 7.4. The buffer used for the original resuspension continued to be used for subsequent steps of particle preparation. Samples were chilled on ice and then sonicated with a probe sonicator (10 min total sonication time, 5 s on and 5 s off, 60-70 W power output) in an ice bath to lyse cells. The cell debris was pelleted in an Eppendorf FA-45-6-30 rotor at 10000 rpm for 10 min, and the supernatant was decanted and collected. The Qβ particles were precipitated from the resulting supernatant by the addition of 10% w/v PEG8000 at 4° C. for 12 h on a rotisserie. The precipitated fraction was isolated from the supernatant by centrifugation in an Eppendorf FA-45-6-30 rotor for 10 min (4° C.) at 10,000 rpm. The pellet was redissolved in ~20 mL of PBS and extracted with a 1:1 v/v solution of n-BuOH/CHCl$_3$ to remove excess lipid. The aqueous fraction was collected following centrifugation using a FA-45-6-30 rotor for 10 min, 4° C. at 10000 rpm. Qβ particles were purified on 10-40% sucrose gradients in an SW28 rotor at 28000 rpm for 4 hours. Approximately 4 mL of light scattering Qβ solution was pulled from each gradient tube and subsequently pelleted in an ultracentrifuge (50.2 Ti rotor, 42K, 3 h). The purified Qβ particles were dissolved in PBS (pH 7.4) and purity was verified via FPLC and DLS. A liter culture typically yielded ~100 mg of pure Qβ. Qβ particles were spin-filtered into deionized water using 100 kDa MWCO spin filters and frozen. The samples were then lyophilized for 3 days to yields a solid white powder.

Melt Processing of Qβ

Poly(lactic-co-glycolic acid) (PLGA) was individually ground manually with a mortar and pestle twice, 10 minutes each time, into a fine powder. PLGA was mixed with the 10 weight percent of lyophilized Qβ via repeated vortexing in a 2 mL Eppendorf tube. A custom built aluminum syringe-die were used for melt processing of the blends to minimize material input. The syringe-die systems consisted of a cylinder with a circular 1 mm exit diameter that was wrapped with heating tape, combined with a digital control element to provide constant heating. The cylinder was designed to fit a polypropylene 1 mL volume Norm-Ject syringe which were filled with 300-350 mg of the PLGA/Qβ blend. The blend was heated at 95° C. as determined by a glass thermometer for 10 minutes. The melted PLGA/Qβ blend was flowed through the die using a syringe pump with a velocity of 3 mm s$^{-1}$ (~2.35 mm$^3$ s$^{-1}$ volumetric flow rate). The resulting cylindrical implants had diameters ranging from 1.0-1.3 mm.

Qβ Dye Conjugation

Qβ was conjugated with fluorescent N-hydroxysuccinimide functionalized Cy5 dye through reaction with amines from lysine residues on the surface of Qβ. 15 mg of Qβ in 2.5 mL of phosphate buffer (100 mM, pH 8) was added to two amber 1.5 mL Eppendorf tubes, with 1.25 mL of Qβ solution in each tube. 400 molar equivalents of NHS-Cy5 in DMSO (1.46 mg in 324 µL total volume, 162 µL per tube) were added to the Qβ solutions, vortexed, and incubated at room temperature for 4 hours with rotary agitation at 100 rpm. The excess dye was removed via repeated centrifugal filtration using 100K MWCO spin filters until no absorbance at 650 nm, indicative of Cy5 dye, was detected via UV-vis spectroscopy. The Qβ-Cy5 particles were analyzed via DLS and FPLC with wavelengths monitored at 280, 260, and 650 nm. The particles were then spin filtered into deionized water and lyophilized. PLGA material laden with 10 wt % Qβ-Cy5 was prepared via the previously described method.

Microneedle Fabrication

Microneedle arrays were fabricated via melt molding utilizing silicone molds (Micropoint Technologies) that were designed to yield an array of 100 pyramidal needles with a base size of 100×100 µm and a length of 250 µm. The microneedle molds were filled with ~2 cm lengths of neat PLGA, 10% Qβ/PLGA, or 10% Qβ-Cy5/PLGA material (~120 mg) and incubated in a vacuum oven at 95° C. The material was incubated in the oven under vacuum for 10 minutes, then vented to atmospheric pressure for 10 minutes. This cycle was repeated a total of 3 times and the samples were then removed and kept at −20° C. for 30 minutes.

The resulting microneedle arrays of were sputter coated with a 10 nm layer of gold and imaged via SEM. The mechanical properties of the needles were measured via compression testing with a rate of 10 µm/s and the maximum strength of the needle was determined from the force value at saturation. The values were reported as the average and standard deviation of 3 samples. Particles were recovered via ethyl acetate extraction performed by dissolving ~100 mg of material in 1 mL of ethyl acetate for 15 minutes. This was followed by centrifugation for 5 minutes at 5,000 rpm using an Eppendorf 5810 R centrifuge with a fixed angle rotor, based on a previously established protocol for organic extraction of active lysozyme. The supernatant was decanted and the process was repeated two more times. The remaining solids were dried under vacuum at room temperature for 24 hours. The solid protein recovered was resuspended in PBS for 24 hours at 4° C. and analyzed via FPLC, DLS, and TEM.

Porcine Skin Puncture and Imaging

Porcine skin was a generous gift from the Dr. Minh Lam and the Department of Dermatology. Skin samples were collected from freshly sacrificed pigs and immediately stored at −80° C. The porcine skin was removed from −80° C. and allowed to thaw at room temperature. The hair was shaved from the skin and a 10 wt % Qβ-Cy5 loaded PLGA microneedle array was applied to the skin and affixed with a layer of parafilm in contact with the skin and tape to ensure the array stayed in place. The skin was placed in an incubator at 37° C. with 95% relative humidity and a solid plastic block weighing 0.713 g was used to apply 7 N of application force to the array for 1 hour. The weight was then removed and the skin with the affixed microneedle array was incubated for 48 more hours. After incubation, the microneedle array was removed and both the array and the application site on the skin were imaging via Maestro fluorescence imaging.

ELISA Analysis of Processed Qβ

ELISA was utilized in order to determine the retention of the biochemical surface characteristic of Qβ after melt processing and microneedle molding. The melt processed and microneedle molded samples were recovered via ethyl acetate extraction and the concentration was determined via Bradford assay. Nunc Maxisorp 96-well plates with 1 µg of Qβ sample in 200 µL of PBS, pH 7.4 at 4° C. overnight. The wells were then blocked with 200 µL of blocking buffer (2.5% w/v dry milk in PBS, pH 7.4) at 37° C. for 1 hour. The wells were then incubated with a 1:2500 dilution of mouse sera collected on day 28 from mice that had been immunized with 3 injections of 50 µg of Qβ on a biweekly basis. The wells were then incubated with 100 µL of a 1:1000 dilution in blocking buffer of alkaline-phosphatase labeled goat anti-mouse IgG for 1 hour at 37° C. The wells were washed between each incubation step using 3×200 µL of 0.1% w/v Tween-20 in PBS, pH 7.4. The wells were developed using 100 µL of PNPP substrate tablets (1 mg/mL), dissolved in 0.1 M glycine buffer at pH 10.4, at 4° C. for 30 minutes. The reaction was stopped with 100 µL of 2 M NaOH and the absorbance was read at 405 nm in triplicate for each sample. Values are expressed as the average and standard deviation of measurements using sera from 2 mice.

Qβ Chimeric Particle Design and Production

The P4 and CH401(Rat) amino acid sequences were inserted at the C-terminal of the Qβ coat protein. A flexible serine and glycine linker was added between the coat protein and peptide to allow the peptide to be displayed effectively. The amino acid sequences are shown below with the linker highlighted in blue.

P4:
(SEQ ID NO: 1)
GGSGSGGPESFDGDPASNTAPLQPEQLQ

CH401(Rat):
(SEQ ID NO: 2)
GGSGSGGYQDMVLWKDVFRKNNQLAP

The DNA coding for the amino acid sequences was optimized for E. coli codon usage using JCat software. The DNA sequence for Qβ coat protein-P4 was synthesized using primer overlap PCR with NcoI and XhoI cutsites at the 5' and 3' ends respectively. The DNA sequence for Q coat protein-CH401 was synthesized by GenScript with NcoI and XhoI cutsites at the 5' and 3' ends respectively. The DNA sequences are shown below with the NcoI/XhoI cutsites highlighted in red and the peptide sequences highlighted in green.

P4:
(SEQ ID NO: 3)
GATATACCATGGCAAAATTAGAGACTGTTACTTTAGGTAACATCGGGAAA

GATGGAAAACAAACTCTGGTCCTCAATCCGCGTGGGGTAAATCCCACTAA

CGGCGTTGCCTCGCTTTCACAAGCGGGTGCAGTTCCTGCGCTGGAGAAGC

GTGTTACCGTTTCGGTATCTCAGCCTTCTCGCAATCGTAAGAACTACAAG

GTCCAGGTTAAGATCCAGAACCCGACCGCTTGCACTGCAAACGGTTCTTG

TGACCCATCCGTTACTCGCCAGGCATATGCTGACGTGACCTTTTCGTTCA

CGCAGTATAGTACCGATGAGGAACGAGCTTTTGTTCGTACAGAGCTTGCT

GCTCTGCTCGCTAGTCCTCTGCTGATCGATGCTATTGATCAGCTGAACCC

AGCGTATCTGGTGGTCCGGAATCTTTCGACGGTGACCCGGCTTCTAACAC

CGCTCCGCTGCAGCCGGAACAGCT (SEQ ID NO: 4)
GCAGTAATAAGGATGACTCGAGTCTGGCTGCA

CH401(Rat):
(SEQ ID NO: 5)
GATATACCATGGCAAAATTAGAGACTGTTACTTTAGGTAACATCGGGAAA

GATGGAAAACAAACTCTGGTCCTCAATCCGCGTGGGGTAAATCCCACTAA

CGGCGTTGCCTCGCTTTCACAAGCGGGTGCAGTTCCTGCGCTGGAGAAGC

GTGTTACCGTTTCGGTATCTCAGCCTTCTCGCAATCGTAAGAACTACAAG

GTCCAGGTTAAGATCCAGAACCCGACCGCTTGCACTGCAAACGGTTCTTG

TGACCCATCCGTTACTCGCCAGGCATATGCTGACGTGACCTTTTCGTTCA

CGCAGTATAGTACCGATGAGGAACGAGCTTTTGTTCGTACAGAGCTTGCT

GCTCTGCTCGCTAGTCCTCTGCTGATCGATGCTATTGATCAGCTGAACCC

AGCGTATGGTGGTTCTGGTTCTGGTGGTTACCAGGACATGGTTCTGTGGA

AAGACGTTTTCCGTAAAAACAACCAGCTGGCTCCGTAATAAGGATGACTC

GAGTCTGGCTGCA

Both DNA sequences and pCDF expression vector were double digested with NcoI and XhoI and agarose gel band purified. The digested DNA sequences were then individually ligated with the digested pCDF vector, ligated, transformed into NEB5α chemically competent cells, and plated onto spectinomycin containing selective LB medium agar plates. The plasmid was purified from an individual colony and successful ligation was verified via sequencing. The pCDF-QPP4 or pCDF-QDCH401(Rat) plasmid was co-transformed with pET28 expression vector containing the wild type Qβ (pET28-Qβ) coat protein into ClearColi® BL21(DE3) E. coli (Lucigen) via electroporation. The transformed E. coli were plated onto spectinomycin and kanamycin containing selective LB medium agar plates.

The chimeric particles were prepared based on a modified protocol described previously. A single colony from plated ClearColi® BL21 E. coli containing either pCDF-QβP4/pET28-Qβ or pCDF-QDCH401(Rat)/pET28-Qβ was added to 100 mL of autoclaved selective containing spectinomycin and kanamycin (50 μg/mL for both antibiotics) LB media and grown to saturation for 12 h at 37° C. A total of 10 mL of culture was then diluted into 1000 mL of freshly prepared selective LB media. Culture growth was monitored by optical density at 600 nm (OD600). When the OD600 of the cultures reached approximately 0.8 (mid log phase), protein expression was induced with the addition of 10 mL of 100 mM IPTG, giving a final IPTG concentration of 1 mM. The temperature was then lowered to 30° C. and incubated at 37° C. for an additional 15 h, at which point cells were collected by centrifugation in an Eppendorf A-4-81 rotor at 4000 rpm (4° C.) for 30 min. The supernatant was decanted, and the cell pellet was frozen at −80° C. until purification. Cells were then resuspended in ~100 mL of PBS, pH 7.4. The buffer used for the original resuspension continued to be used for subsequent steps of particle preparation. Samples were chilled on ice and then sonicated with a probe sonicator (10 min total sonication time, 5 s on and 5 s off, 60-70 W power output) in an ice bath to lyse cells. The cell debris was pelleted in an Eppendorf FA-45-6-30 rotor at 10000 rpm for 10 min, and the supernatant was decanted and collected. The Qβ particles were precipitated from the resulting supernatant by the addition of 10% w/v PEG8000 at 4° C. for 12 h on a rotisserie. The precipitated fraction was isolated from the supernatant by centrifugation in an Eppendorf FA-45-6-30 rotor for 10 min (4° C.) at 10,000 rpm. The pellet was redissolved in ~20 mL of PBS and extracted with a 1:1 v/v solution of n-BuOH/CHCl₃ to remove excess lipid. The aqueous fraction was collected following centrifugation using a FA-45-6-30 rotor for 10 min, 4° C. at 10000 rpm. The particles were purified on 10-40% sucrose gradients in an SW28 rotor at 28000 rpm for 4 hours. Approximately 4 mL of light scattering particle solution was pulled from each gradient tube and subsequently pelleted in an ultracentrifuge (50.2 Ti rotor, 42K, 3 h). The purified particles were dissolved in PBS (pH 7.4) and purity was verified via FPLC, DLS, and TEM. The amount of peptide bearing coat protein was determined via SDS-PAGE and MALDI-TOF spectroscopy. The SDS-PAGE result was analyzed via pixel density analysis using ImageJ software and the MALDI-TOF result was analyzed via peak integration. A liter culture typically yielded ~50 mg of pure particle. For melt processing, the particles were spin-filtered into deionized water using 100 kDa MWCO spin filters and frozen. The samples were then lyophilized for 3 days to yields a solid white powder.

Qβ Chimeric Particle In Vivo Studies

All experiments were carried out in accordance with Case Western Reserve University's Institutional Animal Care and Use Committee. Male Balb/c mice (Charles River) aged 7 weeks (n=5 for each treatment group) were injected 3 times on days 0, 14, and 28. The mice were injected with either 50 μg of Qβ, Qβ-P4, or Qβ-CH401 or 2 μg of P4 or CH401 free peptide in 100 μL sterile PBS through subcutaneous injections behind the neck using a 29G insulin syringe. The amount of free peptide injected was the amount of peptide displayed on the chimeric particle calculated using the SDS-PAGE and MALDI result. All Qβ samples were produced in ClearColi E. coli cells that contain a modified lipopolysaccharide (LPS) outer membrane. Blood (~100 μL) was drawn prior to the first immunization and on a biweekly basis via the retro-orbital plexus using heparinized capillary tubes and collected in Greiner Bio-One VACUETTE™ MiniCollect™ tubes. Serum was separated by centrifuging blood samples at 14,800 rpm, 4° C., for 10 min and stored at 4° C. until analyzed via enzyme-linked immunosorbent-assay (ELISA).

The anti-Qβ IgG response was measured by first coating Nunc Maxisorp 96-well plates with 1 μg of Qβ in 200 μL of sterile PBS, pH 7.4 at 4° C. overnight. The wells were then blocked with 200 μL of blocking buffer (2.5% w/v dry milk in PBS, pH 7.4) at 37° C. for 1 hour. The wells were then incubated with mouse sera at 1:500, 1:2500, and 1:12500 dilutions in 100 μL blocking buffer for 2 hours at 37° C. The wells were then incubated with 100 μL of a 1:1000 dilution in blocking buffer of alkaline-phosphatase labeled goat anti-mouse IgG for 1 hour at 37° C. The wells were washed three times between each incubation step using 200 μL of 0.1% w/v Tween-20 in PBS, pH 7.4. The wells were developed using 100 μL of PNPP substrate tablets (1 mg/mL), dissolved in 0.1 M glycine buffer at pH 10.4, at 4° C. for 30 minutes. The reaction was stopped with 100 μL of 2 M NaOH and the absorbance was read at 405 nm in triplicate for each sample. Values are expressed as the average and standard deviation of 5 mice.

The anti-P4 or anti-CH401 IgG response was measured by coating Pierce Maleimide Activated 96-well plates with 0.2 μg of peptide in 200 μL of sterile PBS, pH 7.4 with 10 mM EDTA overnight at 4° C. The wells were then blocked with 100 μL of 10 μg/mL L-cysteine solution in PBS with 10 mM EDTA for 1 hour at 37° C. The wells were then incubated with mouse sera at 1:500, 1:2500, and 1:12500 dilutions in 100 μL of PBS with 10 mM EDTA for 2 hours at 37° C. The wells were then incubated with 100 μL of a 1:1000 dilution in PBS with 10 mM EDTA of alkaline-phosphatase labeled goat anti-mouse IgG for 1 hour at 37° C. The wells were washed three times between each incubation step using 200 μL of 0.1% w/v Tween-20 in PBS, pH 7.4. The wells were developed using 100 μL of PNPP substrate tablets (1 mg/mL), dissolved in 0.1 M glycine buffer at pH 10.4, at 4° C. for 30 minutes. The reaction was stopped with 100 μL of 2 M NaOH and the absorbance was read at 405 nm in triplicate for each sample. Values are expressed as the average and standard deviation of 5 mice.

Qβ Chimeric Particle Melt Processing

Poly(lactic-co-glycolic acid) (PLGA) was individually ground manually with a mortar and pestle twice, 10 minutes each time, into a fine powder. PLGA was mixed with the 10 weight percent of lyophilized Qβ, Qβ-P4, or Qβ-CH401 (Rat) via repeated vortexing in a 2 mL Eppendorf tube. A custom built aluminum syringe-die were used for melt processing of the blends to minimize material input. The syringe-die systems consisted of a cylinder with a circular 1 mm exit diameter that was wrapped with heating tape, combined with a digital control element to provide constant heating. The cylinder was designed to fit a polypropylene 1 mL volume Norm-Ject syringe which were filled with 150-200 mg of the PLGA/Qβ blend. The blend was heated at 95° C., as determined by a glass thermometer, for 10 minutes. The melted PLGA/Qβ blend was flowed through the die using a syringe pump with a velocity of 3 mm s$^{-1}$ (~2.35 mm$^3$ s$^{-1}$ volumetric flow rate). The resulting cylindrical implants had diameters ranging from 1.0-1.3 mm. Particles were recovered via ethyl acetate extraction performed by dissolving ~100 mg of material in 1 mL of ethyl acetate for 15 minutes. This was followed by centrifugation for 5 minutes at 5,000 rpm using an Eppendorf 5810 R centrifuge with a fixed angle rotor, based on a previously established protocol for organic extraction of active lysozyme. The supernatant was decanted and the process was repeated two more times. The remaining solids were dried under vacuum at room temperature for 24 hours. The solid protein recovered was resuspended in PBS for 24 hours at 4° C. and analyzed via FPLC, DLS, and TEM.

Qβ Chimera Release Study

Release studies were conducted on samples of the melt processed implants (~1 cm long, 10-15 mg, n=3). Samples were placed in 2 mL Eppendorf tubes with 250 μL of Gibco 1×PBS with 0.01 wt % sodium azide and incubated at 37° C. with 90% relative humidity. Aliquots of 225 μL were removed at each time point and replaced with fresh buffer. The protein concentration at each time point was determined via Bradford assay with comparison to a freshly prepared bovine serum albumin standard curve.

Results

PLGA Microneedle Production and Characterization

Figure 9B:
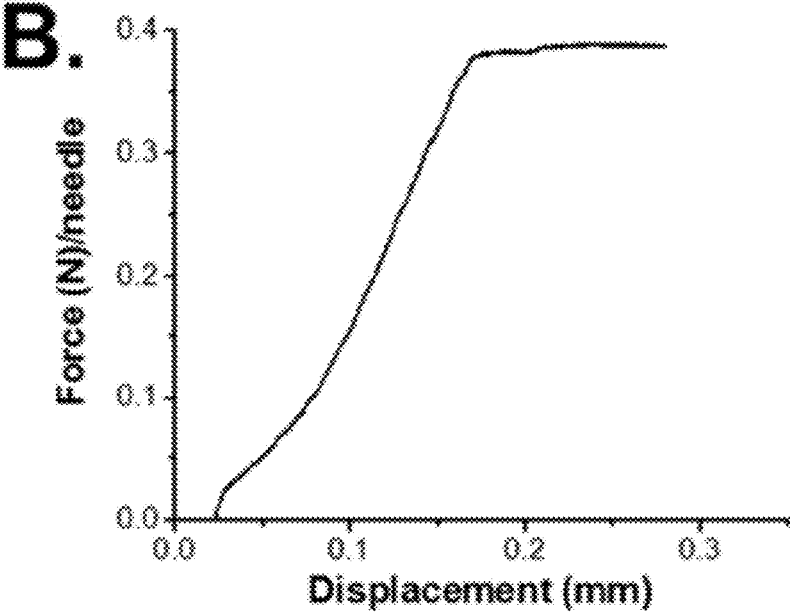

Microneedles were produced using PLGA via a melt molding process where the polymer was melted into a silicone mold designed to yield a 10×10 assembly of 250 μm long pyramidal needles. Melt molding was utilized as it does not require the long drying times or repeated application of solutions associated with coated and layer-by-layer assembly microneedle arrays. The PLGA was melted at 95° C. in a vacuum oven, with the temperature chosen to represent the processing temperature previously used to melt process Qβ with PLGA, and subjected to 3 cycles of degassing to remove air bubbles in the polymer melt. The resulting microneedle array was imaged using SEM and exhibited needles of the correct size and shape based on the silicone mold design (FIG. 9A). Mechanical analysis of the needle strength via compression testing indicated the needles had a maximum strength of 0.349±0.0572 N per needle and an overall maximum strength of 34.9±5.72 N for the total array (FIG. 9B). These ultimate strength values are in the range of puncture strength values for previous microneedle skin application, indicating the molded PLGA microneedle arrays were suitable for dermal administration.

Qβ/PLGA Microneedle Production

After verification that PLGA microneedle arrays could successfully be fabricated at the temperature used for Qβ melt processing, microneedle arrays were prepared with PLGA containing 10 wt % Qβ. The PLGA material containing 10 wt % Qβ was prepared using a syringe extrusion device at 95° C. with a 10 minute incubation time. After melt processing with PLGA, the Qβ/PLGA material was melt molded into microneedle arrays following the same procedure used to make PLGA arrays. The resulting array exhibited similar needle morphology and had a maximum strength of 0.333±0.0388 N per needle, indicating the incorporation of 10 wt % Qβ had negligible effect on the formation and strength of the microneedles formed during melt molding.

Figure 10A:
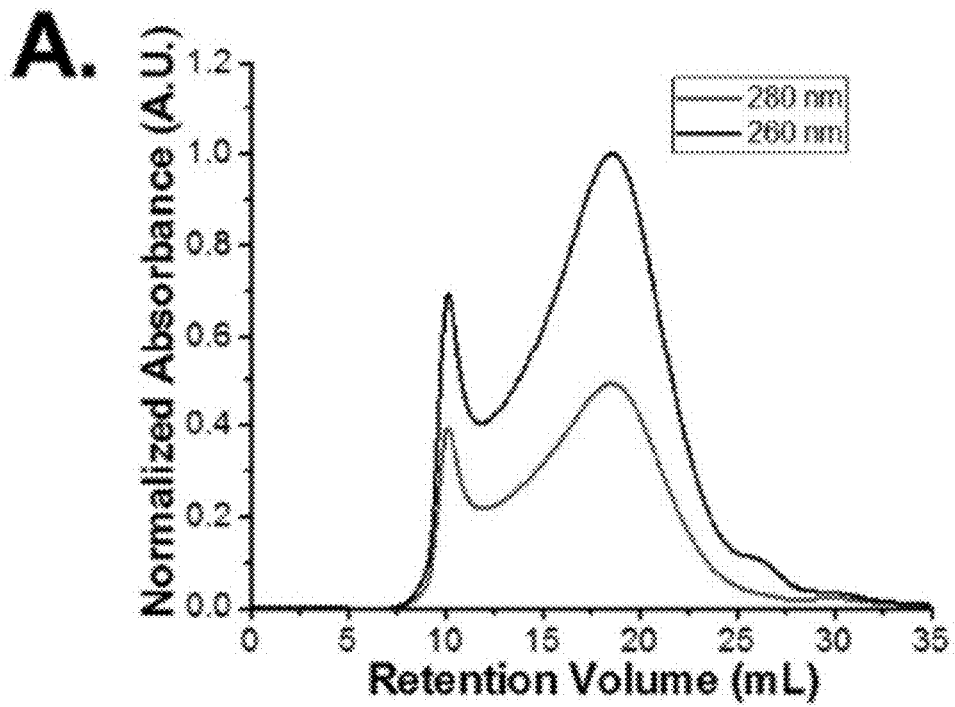
FIGS. 10(A-C) illustrate (A) FPLC chromatogram and (B) DLS histogram, and (C) TEM of Qβ recovered from the microneedle array.
Figure 10B:
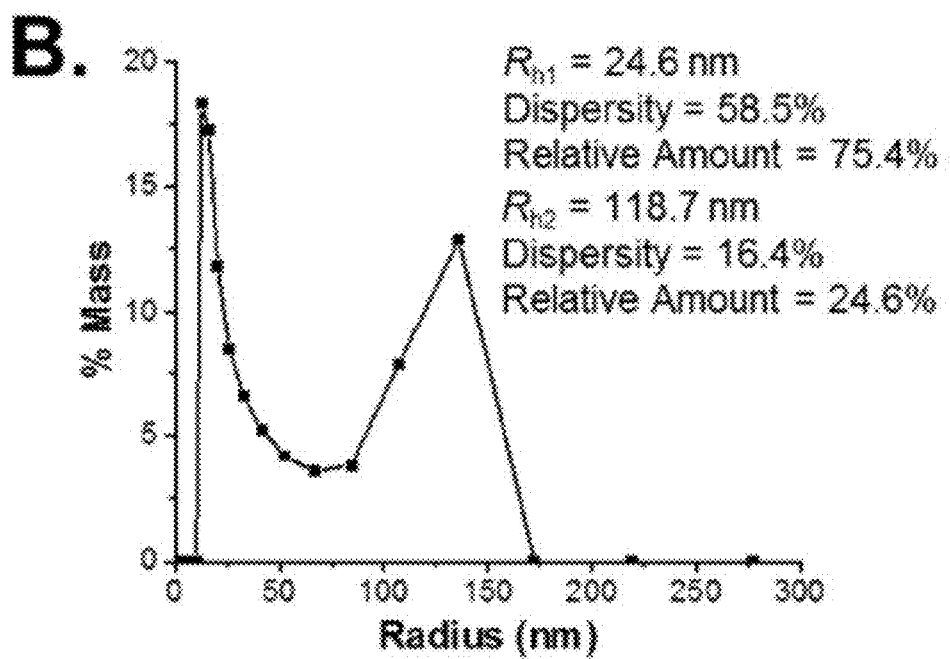
Figure 10C:
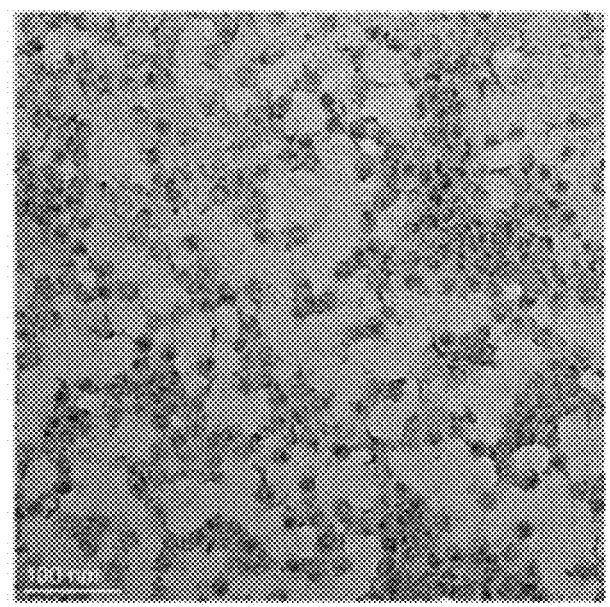

The melt molding process subjected the Qβ to further heat and mechanical stresses during the melting and degassing process. Qβ was recovered from the microneedle array via ethyl acetate extraction using the method described in the previous Example. Analysis of the recovered Qβ via FPLC indicated an increase in the aggregated species relative to initial melt processing studied previously (FIG. 10A). Curve fitting and integration of the two major peaks in the FPLC chromatogram yielded relative percentage of 14.1% for the aggregate peak at 10 mL and 85.9% for the major peak centered at 18.5 mL corresponding to intact particles. DLS analysis of the microneedle processed Qβ also indicated the presence of aggregated species, with two major peaks at 24.6 and 118.7 nm (FIG. 10B). These peaks had relative percentages of 75.4% and 24.6% respectively, with the aggregated species having a higher relative percentage than that calculated from the FPLC result. This discrepancy was due to the limitations of the curve fitting process not fully taking into account the peak broadening towards higher elution volumes of the peak centered at 18.5 mL. The broadening was due to smaller aggregated species in the sample that eluted between the main Qβ peak and the void volume. These aggregated species were included in both peaks of the DLS result, resulting in the increase in value of the average radius for the lower peak from 15.1 nm to 24.6 nm and the higher percentage of the larger peak relative to the FPLC result. TEM analysis of the recovered Qβ also verified the presence of intact viral nanoparticles, in agreement with the FPLC and DLS result (FIG. 10C). Overall, further melt processing with PLGA into microneedle arrays resulted in Qβ that had a majority of the population as single nanoparticles. The results seen were similar to Qβ/PLGA material that was melt pressed, where Qβ recovered from the melt pressed samples exhibited an increase in the aggregated population in response to post-processing with further heat and pressure. The melt molding process subjected Qβ to the same stresses with, further applied heat and mechanical stresses generated during the degassing process where bubbles were forced out of the polymer melt.

While Qβ was able to be successfully recovered from the microneedle array and maintain particle integrity, we sought to further explore the integrity of the surface epitopes of Q after initial melt processing and melt molding into microneedle arrays. We have shown that mice implanted with Qβ/PLGA devices were able to be immunized, therefore we expected that the surface epitopes would be maintained after melt processing and microneedle production. ELISA was utilized with anti-Qβ IgG from sera that was generated in mice immunized with 50 µg doses of Qβ in solution following a standard 3, biweekly injection schedule. Qβ, Qβ that was processed at 10 wt % with PLGA and recovered, and 10 wt % Qβ/PLGA that was further melt molded into microneedles and recovered were all coated onto adsorbing ELISA plates and analyzed using immunized sera from two mice. The results were normalized via the unprocessed Qβ ELISA response to yield percent antibody recognition values (FIG. 11). The results indicated a small loss in antibody recognition for melt processed and microneedle molded Qβ, with percent recognition values of 92.1 and 90.2% respectively. This loss in antibody recognition may be due to particle aggregates blocking antibody binding sites or degradation of surface residues through oxidation or chemical reaction with other residues or PLGA. Both processed Qβ samples exhibited higher error in antibody recognition relative to native Qβ. This was potentially due to inconsistent coating of the Qβ on the ELISA well surface by aggregated species between wells resulting in the obscuring of adjacent particles depending on the orientation of aggregates when they adsorb onto the surface. Overall, the ELISA result indicated that melt processing and microneedle processing did not result in a large loss of the surface biochemical character of Qβ and that the thermal and mechanical stresses applied during microneedle molding does not have further impact after initial melt processing.

Porcine Skin Puncture Model

A porcine skin puncture model was used to determine the in vitro ability of the microneedle arrays to effectively penetrate the skin and release Qβ. The porcine skin puncture model is a commonly used in vitro model for skin puncture, as it is representative of the inhomogeneity of skin and hair follicle spacing. Qβ was conjugated with NHS functionalized Cy5 fluorescent dye in order to visualize the location of Qβ after release into the skin. FPLC characterization of Qβ-Cy5 indicated successful attachment of Cy5 through co-localization of the Qβ peak with a peak at 650 nm, the maximum absorbance of Cy5 (FIG. 12A). There was also no 650 nm peak in the 30 to 35 mL elution volume range that would correspond to free Cy5 dye, indicating that all excess dye had been removed. The DLS histogram of Qβ-Cy5 indicated the conjugation did not result in any particle aggregates (FIG. 12B).

The Qβ-Cy5 particles were then lyophilized, melt processed at 10 wt % with PLGA at 95° C., and melt molded into microneedle arrays via the method previously described. The microneedle arrays containing Qβ-Cy5 were fluorescent after melt processing and molding, indicating exposure to high temperatures during the processing did not degrade the Cy5 dye. The microneedle array was applied to shaved porcine skin using 7 N of application force for 1 hour at 37° C., then the insertion force was removed and the microneedle patch was affixed with tape where it was inserted for 48 hours. The insertion force of 7 N was chosen to be on the lower end of insertion forces typically used in in vitro studies (10-20 N) to ensure the array did not fracture during administration. Clinical self-administration of microneedle patches usually involved the microneedle in a cloth or plastic enclosure inserted via force from the fingers, which was typically 9-11 N for the entire array.

Figure 13:
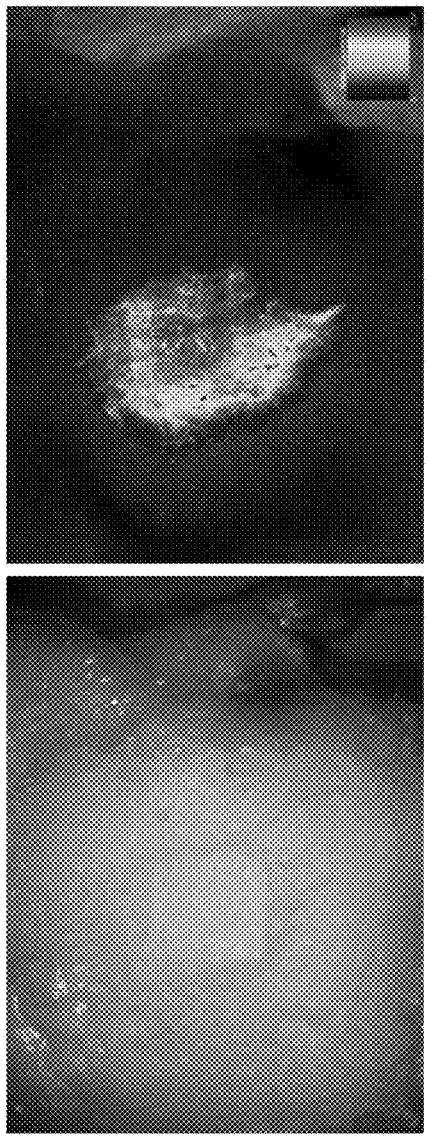
FIG. 13 illustrates optical (left) and fluorescent (right) images of porcine skin administered with PLGA microneedles laden with 10 wt % Qβ-Cy5. The administration site was visible in the optical image as the square indentation.

The patch was removed from the skin and puncture marks were clearly visible in the administration site. The microneedle array had no needles present on the surface, indicating they dissolved during the administration process. The administration site was imaged optically and fluorescently (FIG. 13) and clearly indicated that the fluorescently labeled viral nanoparticles were released into the skin and diffused out through the puncture site. The area of diffusion was limited due to lack of fluid flow through the skin. This limitation can be overcome through the use of a Franz cell to mimic physiological fluid flow and enhance diffusion through the skin. The fluorescent image indicated areas of high signal intensity around the left hand side of the administration site, corresponding to a higher density of hair follicles. Previous results administering nanoparticles using microneedle arrays have indicated they migrate to and accumulate in hair follicles, thus the Qβ-Cy5 nanoparticles had a tendency to accumulate in hair follicles upon microneedle administration.

Chimeric Q-Her2 Epitope Chimeric Particle Design and Production

Qβ was further expanded as a vaccine platform through the display of HER2+ breast cancer epitopes on the nanoparticle surface. Passive immunotherapy utilizing a monoclonal antibody against HER2, herceptin, has seen great success in clinical application. HER2 epitope vaccines are a promising platform for cancer immunotherapy to generate antibodies against HER2 presenting cancer cells using a patient's own immune system and eliminating the need for repeated injections of herceptin. There has been extensive research into peptide based HER2 vaccines, however as a self-antigen present in the body that is normally tolerated there is an inherent hurdle into inducing a memory immune response against the epitope. This limitation can be overcome by presentation on viral nanoparticle systems to induce a strong immune response against the presented antigen. Indeed, presentation of the peptide epitopes P4 and CH401 have been shown to induce a strong immune response against the peptides in murine models. We sought to incorporate the P4 and CH401(Rat), a derivative of the human CH401 peptide sequence using the rat amino sequence, onto the surface of Qβ through a genetic fusion strategy. Genetic fusions of Qβ with peptides and proteins have been successfully produced and utilized for vaccination and cell targeting. These have been accomplished through the addition of the peptide sequence to the C-terminal of the Qβ coat protein, which is exposed on the surface of the assembled Qβ particle.

Figure 14:
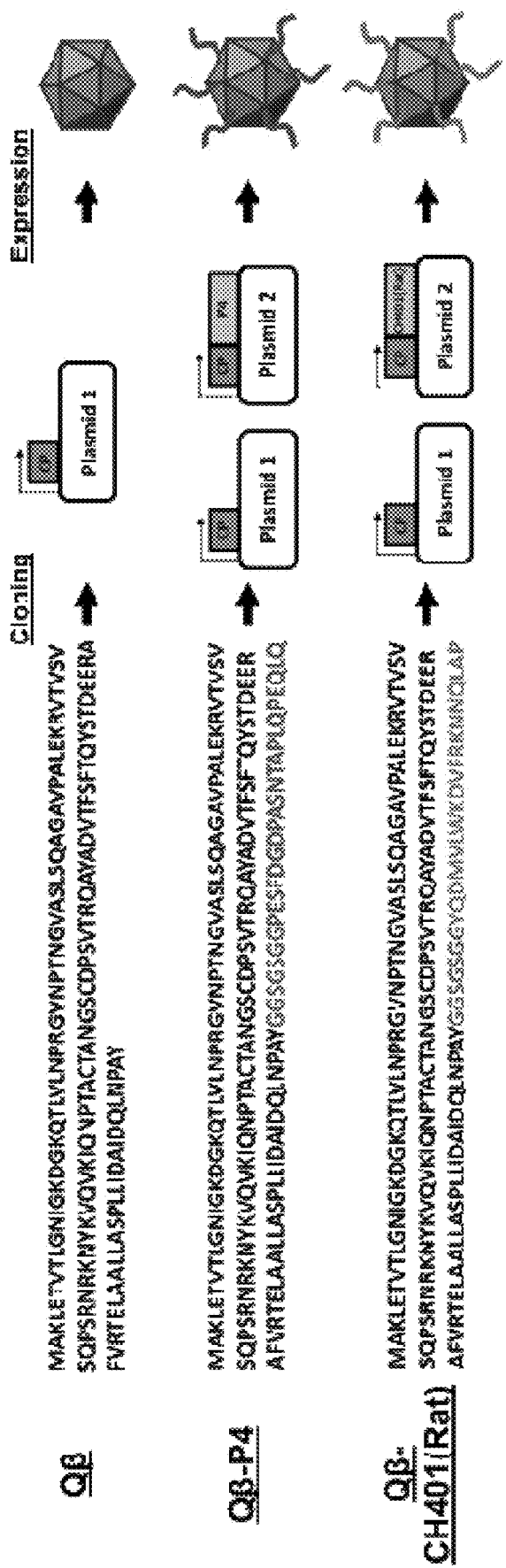
FIG. 14 illustrates amino acid sequences of wild type Qβ coat protein, Qβ coat protein fusion with P4, and Qβ coat protein fusion with CH401(Rat). The flexible linker was shown in blue, the P4 peptide sequence was shown in red, and the CH401(Rat) peptide sequence was shown in green. These amino acid sequences were cloned into an expression plasmid and co-expressed with the wild type Qβ coat protein sequence. The self-assembled particles displayed the P4 or CH401(Rat) peptide sequence on the particle surface.

The DNA sequence of the Qβ coat protein was altered to include DNA coding for a short, flexible linker consisting of glycine and serine followed by the P4 or CH401 sequence at the C-terminal of the Qβ coat protein. The altered Qβ coat protein DNA sequence was then cloned into the pCDF expression vector and transformed into E. coli simultaneously with a pET28 expression vector coding for unaltered Qβ coat protein. Expression of both the coat protein with the peptide extension and the unaltered coat protein allowed for the self-assembly of Qβ particles consistent of native coat protein and coat protein displaying the peptide on the surface (FIG. 14).

Figure 15A:
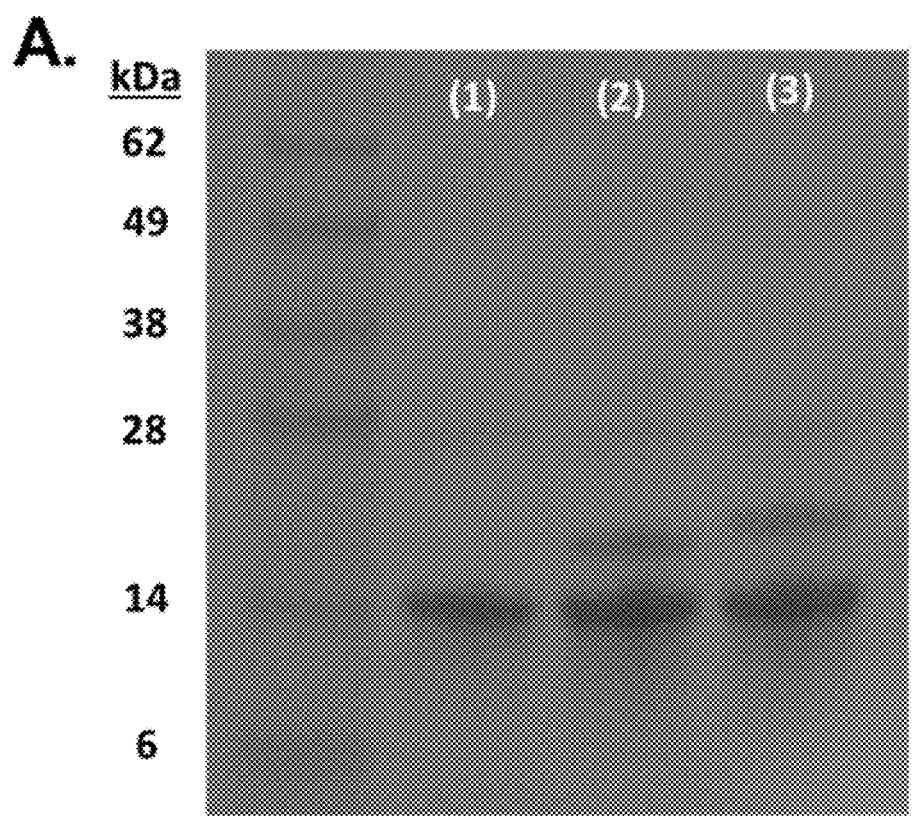
FIGS. 15(A-C) illustrate (A) SDS-PAGE gel of (1) wild type Qβ, (2) Qβ-P4, and (3) Qβ-CH401(Rat). Wild type Qβ exhibited a single band at ~14 kDa indicating native Qβ coat protein. The appearance of a second band for Qβ-P4 and Qβ-CH401(Rat) at ~17 kDa was indicative of coat protein fused to each peptide respectively (coat protein-P4=16.68 kDa, coat protein-CH401(Rat)=17.06 kDa). (B) MALDI-TOF spectrum of Qβ-P4 exhibiting wild type coat protein at 14.17 kDa and the coat protein-P4 fusion at 16.70 kDa (14.25 and 16.68 kDa calculated mass respectively). (C) MALDI-TOF spectrum of Qβ-CH401(Rat) exhibiting wild type coat protein at 14.16 kDa and the coat protein-CH401 (Rat) fusion at 16.96 kDa (14.25 and 17.06 kDa calculated mass respectively).
Figure 15B:
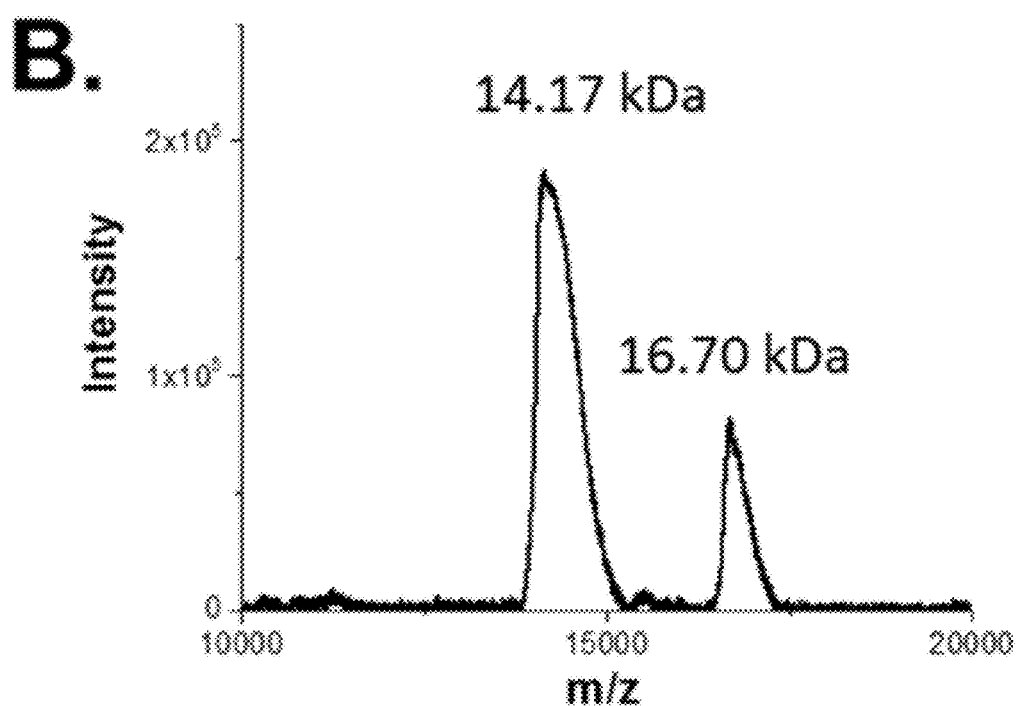
Figure 15C:
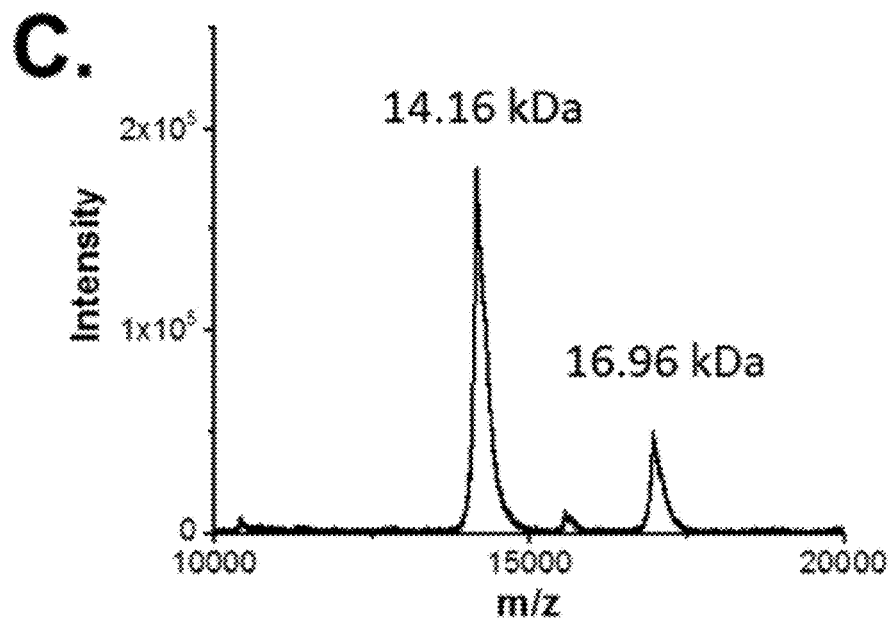
Figure 16A:
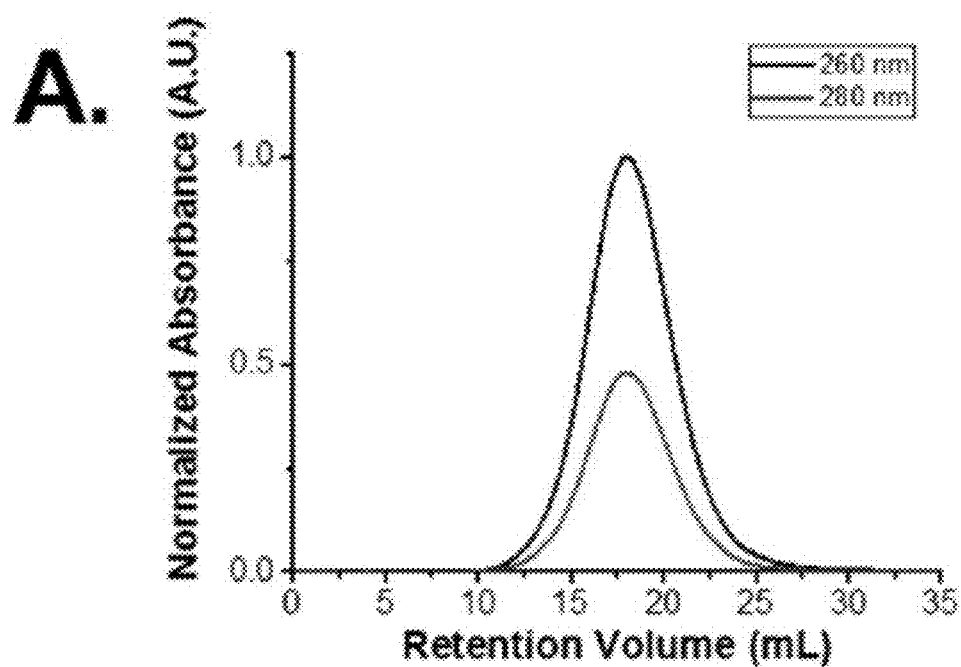
FIGS. 16(A-F) illustrate (A) FPLC chromatogram, (B) DLS histogram and (C) TEM micrograph of purified Qβ-P4 particles. (D) FPLC chromatogram, (E) DLS histogram, and (F) TEM micrograph of purified Qβ-CH401(Rat) particles.
Figure 16B:
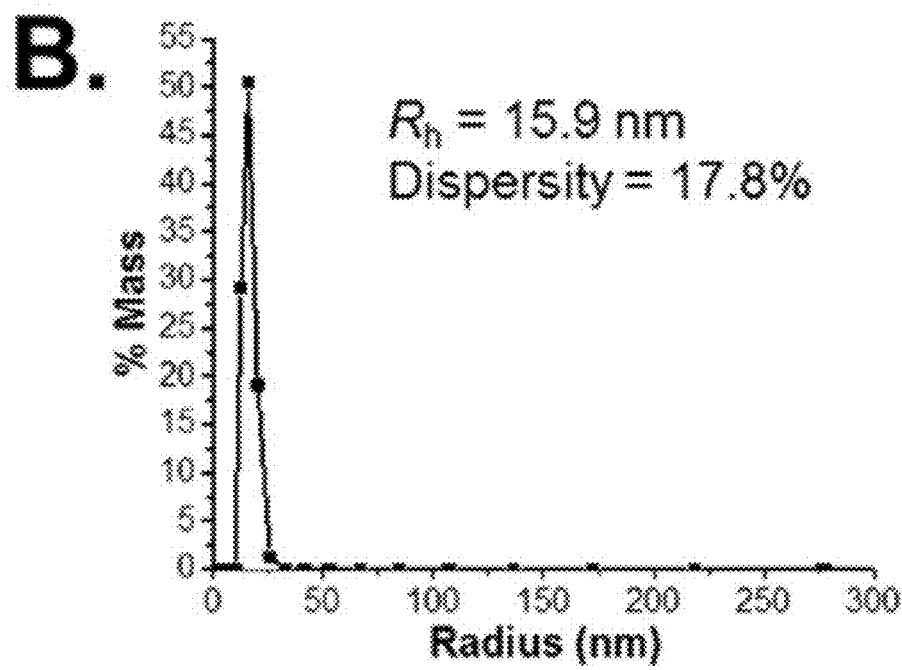
Figure 16C:
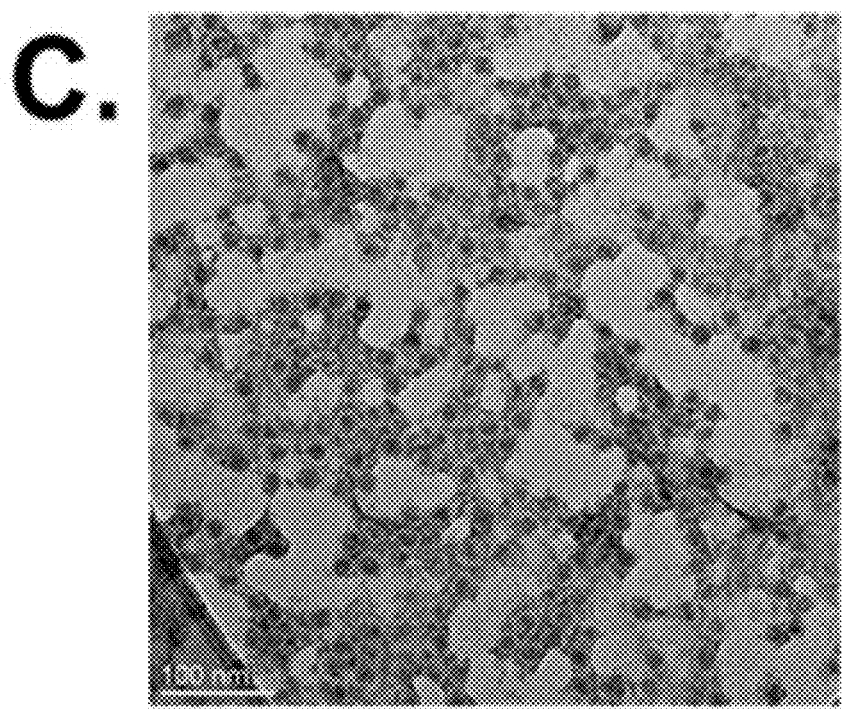
Figure 16D:
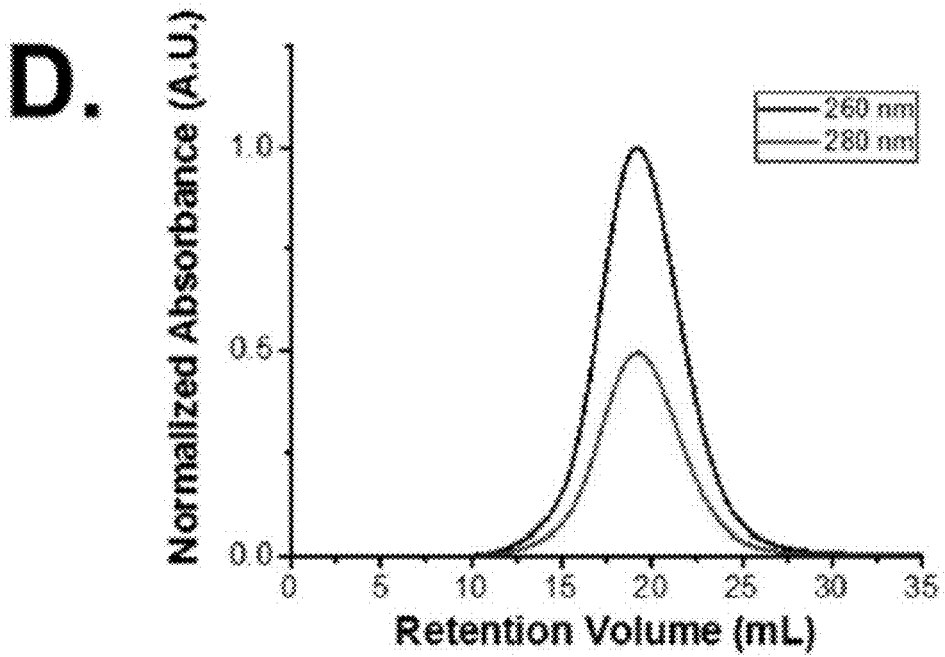
Figure 16E:
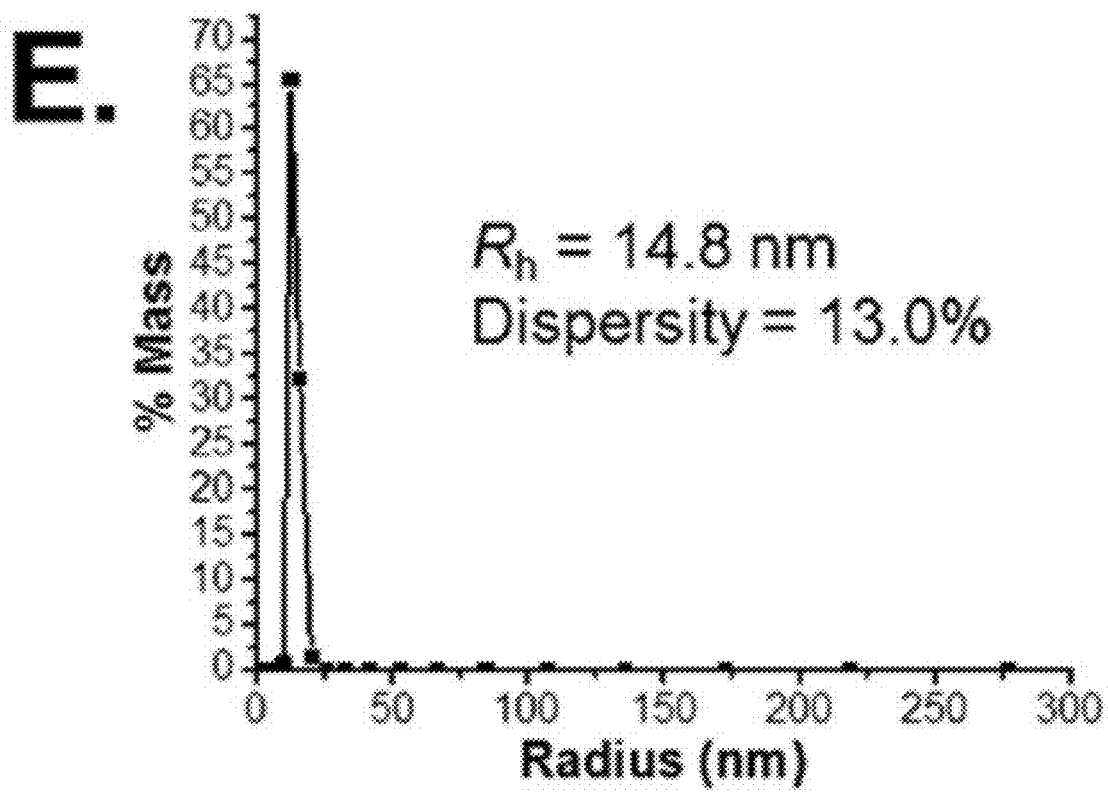
Figure 16F:
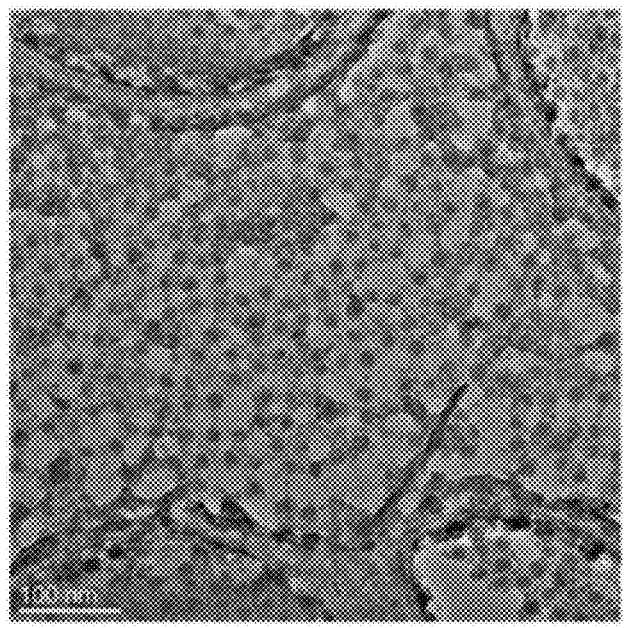

Particles bearing either P4 or CH401(Rat) were successfully created through the co-expression of both expression vectors and purified from E. coli. The amount of peptide bearing coat proteins incorporated into particles was determined from both SDS-PAGE and MALDI-TOF analysis (FIG. 15). The MALDI analysis had the appearance of peaks corresponding to the expected molecular weights of coat protein fused to either peptide that were not present in wild type Qβ, further indicating the successful incorporation of the peptide sequences into the chimeric particles. The results indicated that ~32 P4 and ~32 CH401(Rat) peptides were incorporated into the chimeric Qβ particles respectively.

This amount of peptide incorporation was similar to the results observed with chemical conjugation of the peptides to a viral nanoparticle of similar size to Q. FPLC, DLS, and TEM analysis of the chimeric particles indicated that neither peptide induced particle aggregation and that the assembled particles exhibited the same size and morphology as native Qβ particles (FIG. 16).

Chimeric Particle In Vivo Vaccination

Following the successful expression and purification of P4 or CH401(Rat) peptide bearing chimeric particles, the ability of the particles to elicit a P4 or CH401(Rat) specific immune response was assessed. Mice were immunized via 3 repeated injections on a biweekly of either 50 µg of wild type Qβ, Qβ-P4, or Qβ-CH401(Rat), based on a previous viral nanoparticle conjugate vaccination study (FIG. 17). Two control groups were injected with 2 µg of free P4 or CH401(Rat) peptide, corresponding to the amount of peptide displayed on 50 µg of Qβ-P4 or Qβ-CH401(Rat). Sera was collected from the mice to assess the immune response of the mice in response to the Qβ carrier and the peptides.

The immune response of the treatment groups to the HER2 peptide and the Qβ carrier was assessed via ELISA analysis of the collected sera from day 0, 14, 21, and 28. The sera was tested against plates coated with the P4 or CH401 (Rat) peptide or plates coated with wild type Qβ, allowing for the separation of the immune response to both components of the chimeric particles. Analysis of the immune response to sera collected on day 0, prior to immunization, had no apparent response to the peptides or Qβ as expected. Further ELISA analysis of the response on days 14, 28 and 42 had exhibited no strong response to either the P4 or CH401(Rat) peptide displayed on the surface or the chimeric particles (FIG. 18).

Mice treated with the free peptide also did not display an immune response, likely due to the rapid clearance of the small peptide once injected, consistent with previous results. Treatment groups injected with Qβ or the chimeric Qβ particles did exhibit a strong immune response to the Qβ carrier, demonstrating that the particles were processed and presented by APCs to generate anti-Qβ antibodies (FIG. 19).

The Qβ-P4 treatment group did exhibit some P4 peptide specific antibody response at day 28 and 42, however the response was an order of magnitude lower than mice immunized with viral nanoparticles bearing P4 via chemical conjugation. The lower response observed with the genetic fusion of the peptide to the coat protein versus chemical conjugation may be due to differences in how the coat protein is processed once it was taken up by antigen presenting cells (APCs). A short, flexible PEG linker was utilized to couple the peptide to the virus for the chemical conjugation prepared conjugates using a maleimide linkage between the PEG and the peptide. This maleimide linker is generally stable under physiological conditions, however during the endosomal trafficking and processing there are typically high concentrations of glutathione and other reducing agents than can reduce the thio-ether linkage between PEG and the peptide. Processing of antigens by antigen presenting cells involves extensive protease activity, thus the absence of the chemical linker between the peptide and coat protein in the chimeric particle hay may have led to proteolytic cleavage of the presented peptide sequence, resulting in the low peptide specific antibody generation observed. For future studies, altering the peptide linker sequence between the coat protein and the peptide on the chimeric particles to one that is more readily and selectively cleaved during endosomal processing may help enhance the immune response by diminishing non-specific proteolytic cleavage of the presented peptide.

Melt Processing of Chimeric Qβ Particles

Despite the low peptide specific immunogenicity of the chimeric particles, we sought to determine whether incorporation of the peptide genetic fusions into the particles had a negative impact on the stability of the particles during melt processing with PLGA to create single administration vaccine formulations. Qβ, Qβ-P4, and Qβ-CH401(Rat) particles were lyophilized and subjected to melt processing at 10 wt % with PLGA at 95° C. using the same method previously described. The particles were recovered via ethyl acetate extraction and analyzed via FPLC, DLS, and TEM to determine the extent of particle aggregation and denaturation in response to melt processing. Processed Qβ exhibited a small degree of aggregation, evidenced by the appearance of a peak at 10 mL in the FPLC chromatogram and at 132.3 nm in the DLS histogram (FIGS. 20A-B). The total amount of Qβ aggregates from the DLS was lower than the result previously seen, 4.4% versus 16.2% respectively. However, the average size of the lower radius peak had an average value of 23.2 nm versus 12.6 nm from the previous result. This discrepancy was due to binning effects of the lower order aggregates with the single particles, skewing the calculated amount of aggregates. The FPLC aggregate peak was also lower in intensity relative to the previous result and the overall difference may have been due to slight differences in the temperature profile of the syringe extruder applying different levels of thermal energy during melt processing. TEM of the processed Qβ exhibited particles of the correct size and morphology, verifying that the particles maintained integrity during melt processing, consistent with previous results (FIG. 20C).

Analysis of processed Qβ-P4 via FPLC and DLS indicated similar levels of aggregation as wild type Qβ, with the appearance of a peak at 10 mL in the chromatogram and a peak at 132.8 nm in the DLS histogram (FIGS. 21A-B). TEM analysis also yielded similar result with intact particles (FIG. 21C). Processed Qβ-CH401(Rat) exhibited a small increase in aggregated species relative to wild type Qβ and had a more pronounced aggregate peak at 10 mL on the FPLC chromatogram (FIG. 21D). The DLS histogram was in agreement with the FPLC result, and exhibited two aggregate peaks at 129.7 and 265.2 nm (FIG. 21E). The increase in aggregation for processed Qβ-CH401(Rat) relative to Qβ-P4 particles may be due to the CH401(Rat) peptide having more a less charged characteristic. Furthermore, studies done with the chemical conjugation of these peptides to a viral nanoparticle have shown CH401(Rat) conjugates have a higher tendency to aggregate in solution than P4 conjugates at higher concentrations. The factors behind the increase in aggregation for Qβ-CH401(Rat) during melt processing are unclear, however the increase is not drastic relative to wild type Qβ. Both Qβ-P4 and Qβ-CH401(Rat) yielded TEM micrographs that indicated intact particles of the correct size and shape (FIG. 21F). Overall, the incorporation of the peptide epitopes into the chimeric assemblies did not have a deleterious effect on the physical structural properties of the particles after melt processing at 95° C. with PLGA.

Figure 22:
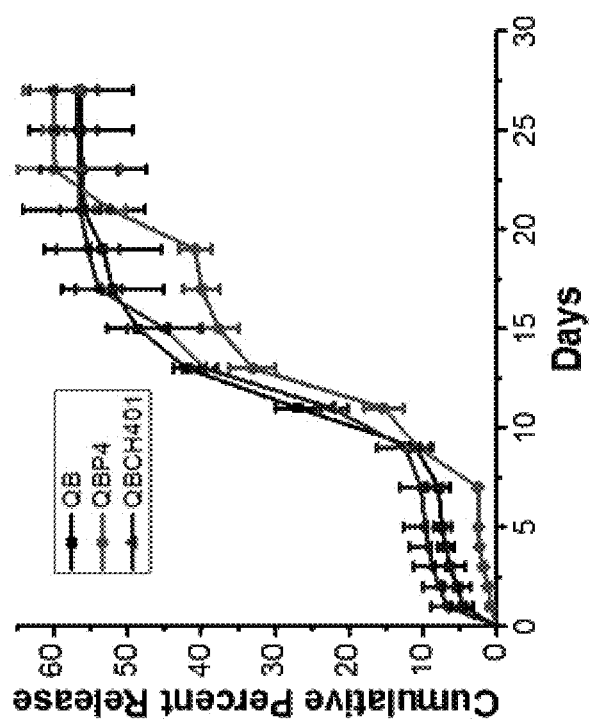
FIG. 22 illustrates in vitro release profile of viral nanoparticles from PLGA materials prepared via melt processing with 10 wt % of wild type Qβ, Qβ-P4, or Qβ-CH401 (Rat). All results were reported as the average and standard deviation of the release from 3 samples.
Figure 23A:
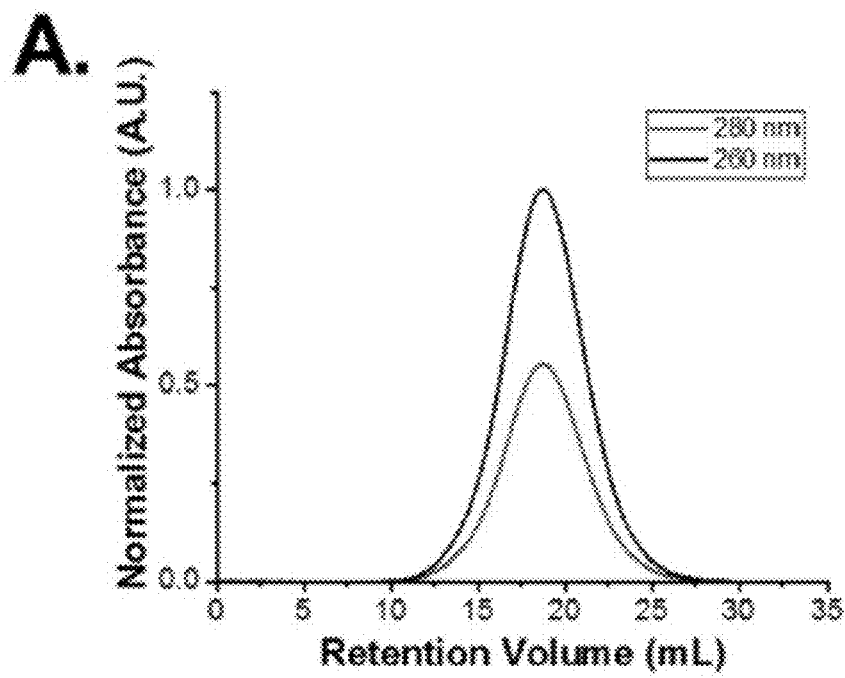
FIGS. 23(A-F) illustrate (A) FPLC chromatogram, (B) DLS histogram, and (C) TEM image of CPMV showing the typical Gaussian peak on the chromatogram and expected sizes in the DLS and TEM results. (D) FPLC chromatogram, (E) DLS histogram, and (F) TEM image of recovered CPMV after melt processing with PLGA/15% PEG8000. The change in relative intensities of the 280 and 260 nm absorbance in the melt processed FPLC chromatogram was due to loss of viral RNA after melt processing.
Figure 23B:
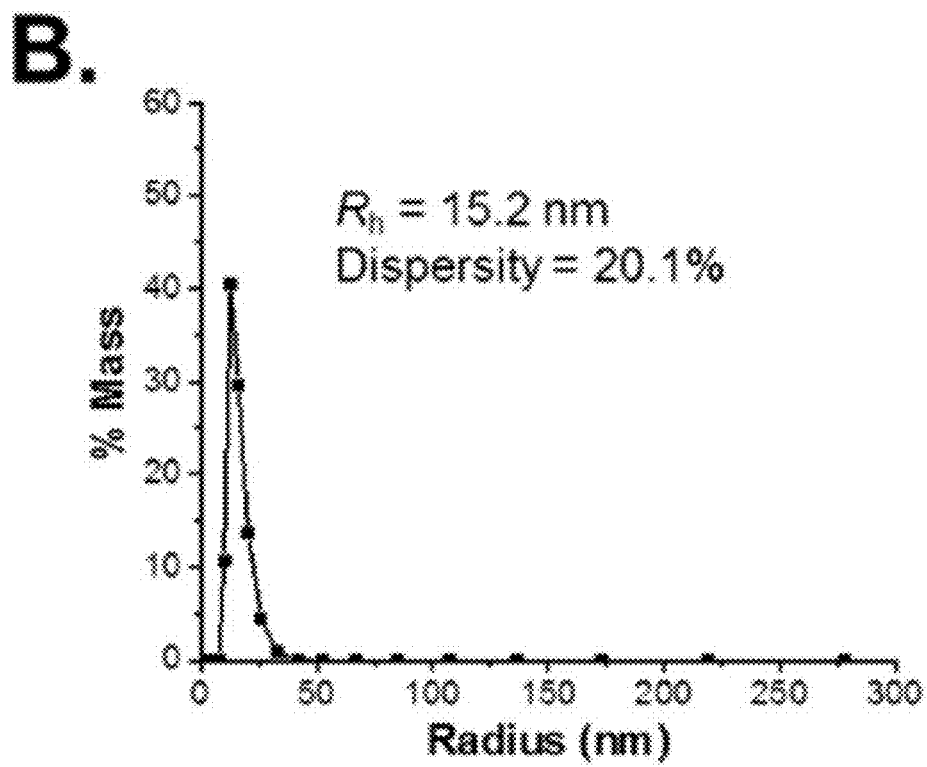
Figure 23C:
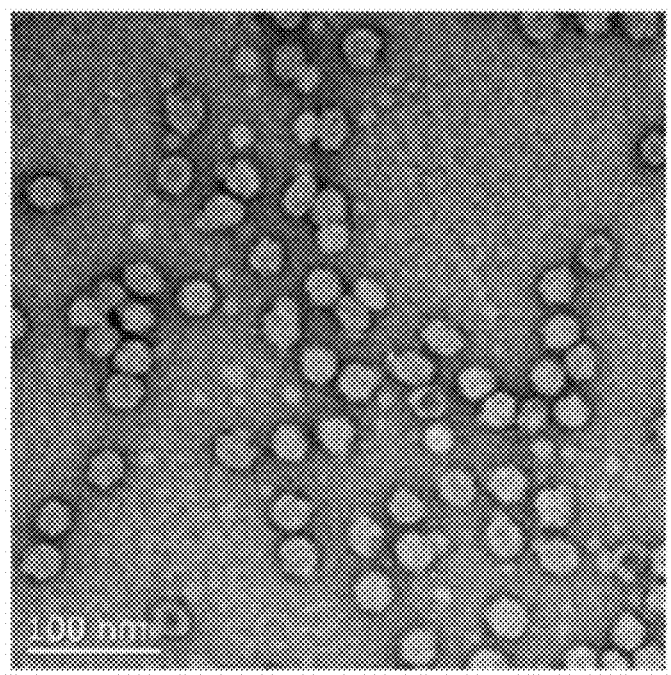
Figure 23D:
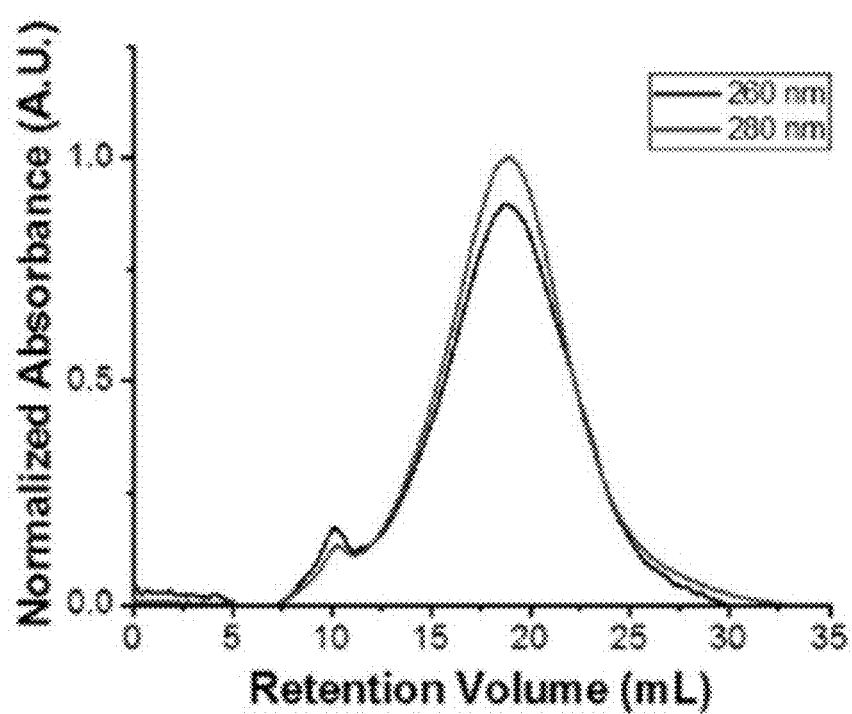
Figure 23E:
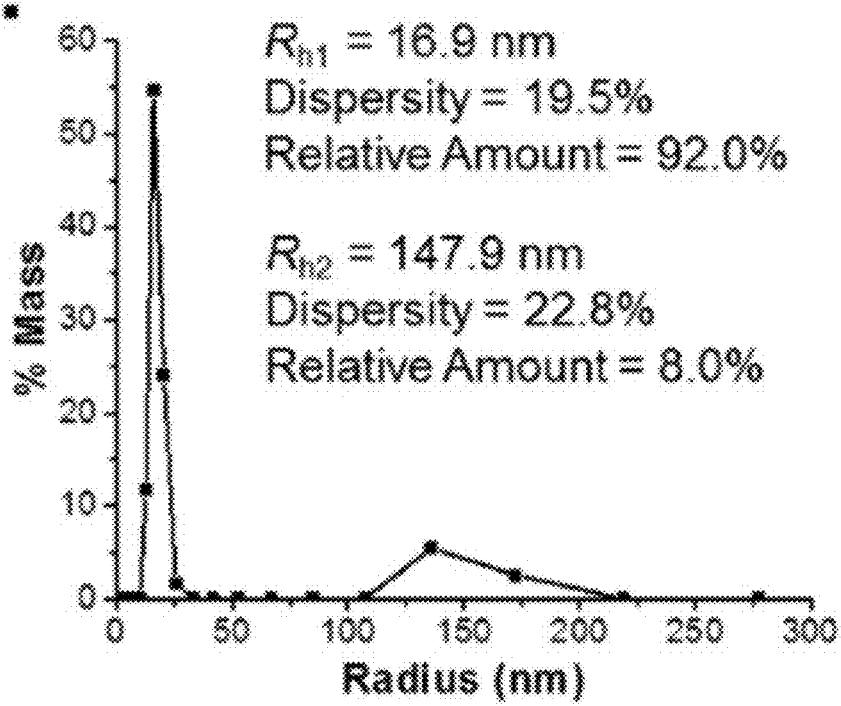
Figure 23F:
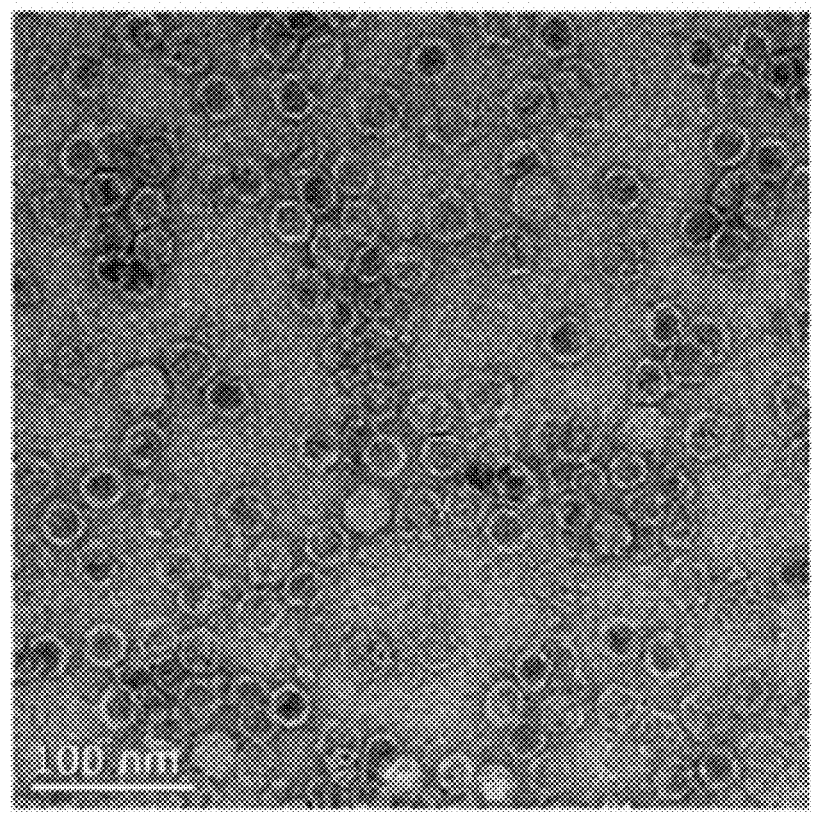

Our previous studies with proteins and viruses melt processed with PLGA have indicated that surface chemistry impacts the in vitro release profile from the PLGA material. Thus, the in vitro release of PLGA materials prepared via melt processing with 10 wt % of Qβ, Qβ-P4, and Qβ-CH401 (Rat) was assessed to determine the effect of the surface P4 or CH401(Rat) peptide epitopes (FIG. 22.). The release study was conducted using PBS at 37° C. to model physiological conditions for 27 days. All samples exhibited similar release profiles and reached a maximum of ~56% cumulative release. The release was more rapid than 10 wt % loaded Qβ material studied, and this was likely due to the release buffer volume being half that of the previous release study. As previously discussed, in vitro release from PLGA devices is dependent on the release conditions. PLGA laden with Qβ-P4 did exhibit a smaller initial release over the first 7 days, with ~2.5% released versus ~7.5% for Qβ and Qβ-CH401(Rat). P4 is has an overall acidic character and an isoelectric point of 3.3, which should increase the repulsive forces between Qβ-P4 particles and the carboxylic acids present in PLGA, thereby increasing release. P4 may form salt bridges with lysine residues on the surface of Qβ, diminishing the acidic characteristic and increasing the hydrophobic characteristic of the particle which can more strongly interact with the hydrophobic portions of PLGA and slow release. CH401(Rat) has an overall slightly basic characteristic, with a pI of 9.25, and may not form these interactions. Nonetheless, all samples exhibited similar release profiles during the bulk erosion phase after day 7. The in vitro release result indicated the incorporation of peptide epitopes via genetic fusion onto Qβ melt processed with PLGA may have an effect on the initial diffusion controlled phase of release, but it does not have a significant effect on the release profile during the bulk erosion phase.

Example 3

In this Example, we sought to apply the melt-processing methods developed Example 2 for Qβ to create PLGA based materials laden with CPMV for intratumoral administration and extended release. In the previous study, cylindrical implants were directly implanted into the subcutaneous space of the mice, and direct implantation of PLGA rods into cancer bearing sites has previously been shown to successfully deliver anti-cancer agents. This route of administration may not be viable for tumor sites that have limited space or accessibility; therefore, we transformed the melt processed material into a formulation that could be injected as a suspension. Oscillatory ball milling was used to create micron sized particles of melt processed cylindrical PLGA/CPMV material to maintain the solventless nature of the process. The PLGA/CPMV microparticles were able to be manufactured while maintaining CPMV particle integrity and effectively impede ovarian cancer progression with a single administration. We further applied the CPMV melt processing method to create microneedle arrays to allow for the dermal administration of CPMV as an in situ vaccine. Microneedles allow for the facile and pain free administration of immunostimulatory agents through application of micron sized needles on the skin. Incorporation of CPMV into PLGA microneedle arrays via melt processing would allow for the direct administration of CPMV as an in situ vaccination device to skin cancers such as melanoma. Overall, CPMV was able to be successfully formulated into several PLGA based devices via melt processing and maintain structural and biochemical integrity.

Materials and Methods

Poly(lactic-co-glycolic acid) (EXPANSORB® 10P019, 50:50 PLGA, inherent viscosity 0.15-0.25 dlg$^{-1}$, 5-20 kDa) was purchased from PCAS. Potassium phosphate monobasic anyhdrous, potassium phosphate dibasic anydrous, sodium phosphate dibasic hetptahydrate, Gibco 1×PBS pH 7.4, butanol, Miller LB Broth, D-sucrose, sodium azide, sodium chloride, ethyl acetate, 1-step PNPP substrate, PNPP tablets, Tween-20, albumin standard, chloroform, n-butanol, carborundum, and sodium hydroxide were purchased from Fisher Scientific. Poly(ethylene glycol) ($M_n$=8000) was purchased from Amresco. Bradford reagent was purchased from VWR. Dry milk was purchased from LabScientific Inc. Uranyl acetate 2% solution was purchased from Electron Microscopy Sciences. PLGA-FPI749 was purchased from Akina Inc. Goat anti-mouse IgG-alkaline phosphatase and goat anti-rabbit IgG-alkaline phosphatase were purchased from Life Technologies. Rabbit anti-CPMV IgG and D-luciferin were a generous gift from Dr. Steinmetz. All reagents were used directly, without further purification.

Instrumentation

Fast protein liquid chromatography (FPLC) was performed using a GE Healthcare AKTA-FPLC 900 chromatography system equipped with a Sephacryl 1000 SF 10/300 size exclusion column. For all FPLC experiments, the mobile phase was 50 mM phosphate buffer, with 150 mM NaCl (pH 7.4) at a flow rate of 0.4 mL/min. Samples were injected at a concentration of 0.1-0.75 mg/mL and the resulting chromatograms were normalized by the maximum absorbance at 260 nm. Dynamic light scattering (DLS) experiments were performed on a Wyatt DynaPro NanoStar DLS instrument. Samples were analyzed at 25° C. in plastic disposable cuvettes with a path length of 10 mm. Transmission electron microscopy (TEM) was performed on a FEI Technai TF30 ST microscope. Negative stained TEM samples were mounted on 400 mesh hexagonal copper grids bearing Formvar support film, stained with 2% uranyl acetate solution, and allowed to dry for 12 h. Microplate measurements were taken with a Biotek Synergy HT microplate reader. Centrifugation was performed with an Eppendorf 5424 centrifuge for spin filtration or a Beckman Coulter Avanti J-E centrifuge for CPMV purification. Ultracentrifugation was performed with a Beckman Coulter Optima L-100 XP ultracentrifuge. UV-vis spectra were collected using a Shimadzu BioSpecNano UV-vis spectrophotometer. Scanning electron microscopy was performed using a JEOL-6510LV scanning electron microscope at 1 kV. Ball milling was performed using a Fritsch Laboratory Mini Grinder PULVERISETTE 23 equipped with a PTFE grinding bowl. Luminescence imaging was performed using a PerkinElmer IVIS Spectrum BLI imaging system. Confocal images were collected using a Leica TCS SPE microscope with a 635 nm solid state laser.

CPMV Production and Purification

CPMV was produced and purified based on a previously published protocol. *Vigna ungiuculata* plants were grown for 10 days and were inoculated with 50 μg of CPMV in 50 μL of pH 7, 0.01 M phosphate buffer per leaf via mechanical inoculation with a dusting of carborundum. The infection was allowed to proceed for 10 days and the leaves exhibited extensive yellow mottling. The leaves were harvested and stored at −80° C. until further purification.

The leaves were pulverized inside of a plastic bag by hand and then 3 volumes of 4° C. phosphate buffer pH 7, 0.1 M, was added per 100 g (i.e., 300 mL per 100 g). The slurry was homogenized using a standard blender and then filtered through 3 layers of cheese cloth. The filtrate was centrifuged at 10,500 rpm for 20 minutes using with a JLA-10.500 rotor. The supernatant was decanted and had 0.7 volumes of 1:1 (v/v) chloroform:n-butanol added and stirred on ice for 30 minutes. The solution was centrifuged at 6,000 rpm for 10 minutes using a JLA-10.500 rotor. The upper aqueous phase was removed and had NaCl added to 0.2 M concentration and 8 kDa PEG added at 8 wt %. The mixture was stirred for 30 minutes on ice and then stored at 4° C. for 2 hours. The solution was then centrifuged at 14,000 rpm for 15 minutes using a JLA-16.250 rotor. The supernatant was decanted and the precipitate was resuspended in 0.01 M phosphate buffer, pH 7, overnight at 4° C. The solution was then centrifuged at 9,500 rpm using a JLA-16.250 rotor and the supernatant was collected. The supernatant was purified on 10-40% sucrose gradients in an SW28 rotor at 28,000 rpm for 3 hours. The light scattering region was collected from each gradient tube and subsequently pelleted in an ultracentrifuge using a 50.2 Ti rotor at 42,000 rpm for 3 hours. The purified CPMV particles were dissolved in 0.1 M phosphate buffer, pH 7, and purity was verified via agarose gel electrophoresis, FPLC, DLS, and TEM. For melt processing, the CPMV was dialyzed into deionized water via repeated centrifugation at 6,000 rpm using 100,000 kDa MWCO centrifugal spin filters (at least ten spins). The CPMV solution was then frozen at −20° C. and lyophilized for 72 hours. Lyophilized CPMV was resuspended in 0.1 M phosphate buffer, pH 7, and characterized for particle integrity via FPLC, DLS, and TEM.

CPMV Melt Processing

Poly(lactic-co-glycolic acid) (PLGA) and 8 kDa polyethylene glycol (PEG8000) were individually ground manually with a mortar and pestle twice, 10 minutes each time, into a fine powder. The PLGA powder consisted of particles with an average length of 185.8±89.1 μm as determined via SEM image analysis. PLGA was mixed with the 10 wt % of CPMV and 15 wt % PEG8000 via repeated vortexing in a 2 mL Eppendorf tube. The custom built aluminum syringe-die utilized for melt processing of PLGA/protein blends was utilized for the melt processing of CPMV/PLGA/PEG8000 blends. Approximately 200-350 mg of CPMV/PLGA/PEG8000 blend was added into a polypropylene 1 mL volume Norm-Ject syringes and loaded into the aluminum barrel heated at 80° C. as determined by a glass thermometer for 3 minutes. The melted blend was pushed through the 1 mm circular die manually and the resulting cylindrical implants had diameters ranging from 1.0-1.1 mm. For fluorescent material, 5 wt % of PLGA tagged with FPI749 fluorescent die was added to the blend mixture prior to vortexting and melt processed using the same method.

CPMV Recovery or Release and Characterization

Rapid CPMV recovery from implants was performed by dissolving ~50 mg of material in 2 mL of ethyl acetate for 15 minutes. The solution was centrifuged for 5 minutes at 5,000 rpm using an Eppendorf 5424 centrifuge with a fixed angle rotor. The supernatant was decanted and the process was repeated two more times. The remaining solids were dried under vacuum at room temperature for 24 hours. The solid protein recovered was resuspended in 0.01 M phosphate buffer, pH 7, for 24 hours at 4° C. In order to remove free RNA, the resuspended samples were filtered using 10 kDa MWCO centrifugal spin filters for at least 10 filtrations. For released samples, ~50 mg of material was incubated in 250 μL of 0.01 M phosphate buffer, pH 7, at 37° C. and the buffer was removed after 24 hours. The samples were filtered using 10 kDa MWCO centrifugal spin filters for at least 10 filtrations. All samples were analyzed for particle integrity and RNA packaging via agarose gel electrophoresis, FPLC, DLS, and TEM.

CPMV/PLGA/PEG8000 Microparticle Production

Prior to ball milling, 100-150 mg of cylindrical CPMV/PLGA/PEG8000 material was incubated at −80° C. for 1 hour. The cylinders, in ~2 cm lengths, were added to the PTFE grinding bowl with one 10 mm stainless steel grinding ball and the bowl was filled with liquid nitrogen. The material was then milled at 30 Hz for 15 minutes and recovered. The resulting microparticles were imaged via SEM and the diameters of the particles was measured via ImageJ. The diameter distribution was determined from 152 measurements of particles in two images and converted to a frequency plot with a bin size of 2 μm. Confocal images of micoparticles created with material containing 5 wt % PLGA-FPI749 were acquired using an excitation wavelength of 635 nm and the emission was measured from 700-800 nm.

Release Properties of Melt Processed CPMV/PLGA/PEG8000

Release studies were conducted on samples of the melt processed implants (~1 cm long, 9-13 mg, n=3) or microparticles (10-11 mg, n=3). Samples were placed in 2 mL Eppendorf tubes with 200 μL of Gibco 1×PBS with 0.01 wt % sodium azide and incubated at 37° C. with 90% relative humidity. Aliquots of 175 μL were removed at each time point and replaced with fresh buffer. The settled microparticles were not disturbed during the removal and replenishment of buffer. The CPMV concentration at each time point was determined via Bradford assay with comparison to a freshly prepared bovine serum albumin standard curve. The UV-vis extinction coefficient was not utilized for quantification due to the presence of empty CPMV and free RNA that would skew the UV-vis absorbance.

Microneedle Fabrication and Analysis

Microneedle arrays were fabricated utilizing either PLGA/PEG8000 or CPMV/PLGA/PEG8000 cylinders that were initially melt processed using the syringe die extrusion device at 80° C. for 3 minutes. ~2 cm lengths of material were loaded into silicone microneedle molds (Micropoint Technologies) and incubated in a vacuum oven at 80° C. The silicone molds were designed to yield an array of 10×10 needles with 100×100 μm length base and 250 μm height with a pyramidal shape. The samples were subjected to vacuum for 4 minutes to remove air bubbles from the melted material and then vented to atmospheric pressure for 4 minutes to allow for the material to fill the mold. This process was repeated 2 more times for a total process time of 24 minutes. The filled molds were then moved to −20° C. for 30 minutes and removed from the molds.

The resulting microneedle arrays of PLGA/PEG8000 were analyzed for needle morphology via SEM. The arrays were not sputter coated prior to SEM imaging, due to needle degradation during the sputter coating process. The mechanical properties of the needles were measured via compression testing with a rate of 10 μm/s. The maximum strength of the needle was determined from the force value at saturation. The integrity of CPMV after microneedle molding was determined from particles recovered via ethyl acetate extraction as previously described. The recovered CPMV was analyzed via agarose gel electrophoresis, DLS, and TEM.

ELISA Analysis of Processed CPMV

ELISA was utilized in order to determine the retention of the biochemical surface characteristic of CPMV after melt processing and microneedle molding. The melt processed and microneedle molded samples were spin filtered as previously described and the concentration was determined via Bradford assay. Nunc Maxisorp 96-well plates with 1 μg of CPMV sample in 200 μL of PBS, pH 7.4 at 4° C. overnight. The wells were then blocked with 200 μL of blocking buffer (2.5% w/v dry milk in PBS, pH 7.4) at 37° C. for 1 hour. The wells were then incubated with 2 μg/mL of polyclonal rabbit anti-CPMV IgG in 100 μL blocking buffer for 2 hours at 37° C. The wells were then incubated with 100 μL of a 0.6 μg/mL in blocking buffer of alkaline-phosphatase labeled goat anti-rabbit IgG for 1 hour at 37° C. The wells were washed between each incubation step using 3×200 μL of 0.1% w/v Tween-20 in PBS, pH 7.4. The wells were developed using 100 μL of 1-Step PNPP substrate at 4° C. for 10 minutes. The reaction was stopped with 100 μL of 2 M NaOH and the absorbance was read at 405 nm in triplicate for each sample. The averages and standard deviations were normalized to the wild type CPMV response to yield a percent response. Values are expressed as the average and standard deviation of 2 measurements relative to the wild type CPMV result.

OVCA In Vivo Study

All experiments were carried out in accordance with Case Western Reserve University's Institutional Animal Care and Use Committee. Hyperaggressive ovarian ID8-Defb29/Vegf cancer cells (a generous gift from Dr. Steven Fiering, Geisel School of Medicine, Dartmouth College) were transformed to express luciferase and grown following a previously established protocol. Female C57BL/6J mice (Charles River) aged 6 weeks (n=5 per treatment group) were injected with $10^6$ luciferin positive ID8-DebJ29/Vegf-A ovarian cancer cells in the intraperitoneal space using a 29G insulin syringe. On day 7, two groups of 5 mice each were injected with either 12 mg of PLGA/PEG8000 microparticles or 10 wt % CPMV loaded PLGA/PEG8000 microparticles. The microparticles were suspended in 1 mL of sterile PBS, pH 7.4, and immediately injected into the intraperitoneal space utilizing a 22.5 G syringe. The mass of injected material was chosen to deliver 300 μg of CPMV over 20 days based on the in vitro release profile, correlating to 3 injections of 100 μg CPMV on a weekly basis for standard treatment. The other treatment groups injected with 30, 100, and 500 μg doses of CPMV 4 times on a weekly basis starting on day 7. The mice were studied for tumor growth via tumor luminescence, abdominal circumference, and weight on a biweekly basis starting on day 11. The luminescence was determined by injection of 150 μL of luciferin into the intraperitoneal space and incubation for 5 minutes. The luminescence was then measured for 3 minutes and the total photons were calculated from the luminescence image. The results for total luminescence, circumference, and mass were reported as the average and standard deviation of 5 mice.

ELISA was utilized to determine the level of anti-CPMV IgG generation as a result of CPMV loaded microparticle administration, blank PLGA/PEG8000 microparticles, and weekly 100 μg CPMV injections. Retro-orbital bleeds were conducted on 2 mice from each group on day 46 utilizing heparinized capillary tubes and ~100 μL of blood was collected in VACUETTE™ MiniCollect™ tubes. Serum was separated by centrifuging blood samples at 14,800 rpm, 4° C., for 10 min and stored at 4° C. until analyzed via enzyme-linked immunosorbent-assay (ELISA). The anti-CPMV IgG response was measured by first coating Nunc Maxisorp 96-well plates with 1 μg of CPMV in 200 μL of sterile PBS, pH 7.4 at 4° C. overnight. The wells were then blocked with 200 μL of blocking buffer (2.5% w/v dry milk in PBS, pH 7.4) at 37° C. for 1 hour. The wells were then incubated with mouse sera at 1:500, 1:2500, and 1:12500 dilutions in 100 μL blocking buffer for 2 hours at 37° C. The wells were then incubated with 100 μL of a 1:1000 dilution in blocking buffer of alkaline-phosphatase labeled goat anti-mouse IgG for 1 hour at 37° C. The wells were washed between each incubation step using 3×200 μL of 0.1% w/v Tween-20 in PBS, pH 7.4. The wells were developed using 100 μL of PNPP substrate at 4° C. for 10 minutes. The reaction was stopped with 100 μL of 2 M NaOH and the absorbance was read at 405 nm in triplicate for each sample. Values were expressed as the average and standard deviation of 2 mice.

Results

CPMV Melt-Processing

*Vigna unguiculata* plants were infected with previously purified CPMV and the infection was allowed to progress until the leaves had extensive yellow mottling. CPMV was purified from the infected leaves and characterized via FPLC, DLS, and TEM in a similar manner to Qβ (FIGS. 23A-C). The FPLC chromatogram yielded a single peak with no aggregates and the DLS also had a single population with an average radius of 15.2 nm, in good agreement with the known size of CPMV. TEM images also indicated icosahedral particles of the correct size, indicating that CPMV was successfully isolated and purified. The purified CPMV was then spin-filtered into deionized water and lyophilized to yield a slightly yellow powder. Resuspension of the lyophilized CPMV with 0.01 M phosphate buffer and analysis via FPLC, DLS, and TEM did not indicate any particle disassociation or aggregation as a result of the lyophilization process.

Following the lyophilization, CPMV was subjected to melt processing with PLGA in a similar manner to Qβ. A blend of 10 wt % CPMV and PLGA was manually mixed via repeated vortexing and heated at 95° C. for 10 minutes using the syringe extrusion device to create CPMV laden PLGA cylinders. Intact CPMV could not be recovered from these samples and all FPLC, DLS, and TEM results indicated that the melt processing conditions used for Qβ previously resulted in complete denaturation of CPMV. This is likely due to the Qβ coat proteins being interconnected via covalent disulfide linkages, while CPMV coat proteins are stabilized through non-covalent interactions potentially making it more sensitive to applied thermal energy. To prevent particle denaturation, both the applied temperature and incubation time of the blend was lowered to 80° C. and 3 minutes respectively. 100% PLGA was unable to be extruded under these conditions, due to the polymer not fully reaching the melt state and being too viscous to push through the extrusion die. 8 kDa PEG (PEG8000) was added at 15 wt % to act as a plasticizer and bring the melt viscosity down to a level that can be extruded under these conditions. Furthermore, PEG additives in protein-PLGA systems has prevented some aggregation with Qβ in our studies and has been shown to enhance protein stability in microsphere formulations. Therefore, the addition of PEG may also enhance the stability of CPMV in the melt.

CPMV was melt processed at 10 wt % with the PLGA/15% PEG8000 blend and was able to be recovered successfully from the extruded polymer sample. FPLC analysis of extracted CPMV yielded two, overlapping Gaussian peaks forming a single skewed peak. These two peaks, with maxima at 18.1 mL and 21.1 mL, corresponded to CPMV particles and disassociated RNA respectively. Spin filtering the CPMV and free RNA sample to remove free RNA yielded an FPLC chromatogram, consisting of only the CPMV particle peak (FIG. 23A). The spin-filter used had a 10 kDa MWCO, smaller than free CPMV coat proteins (41.2 and 23.7 kDa for the L and S subunit proteins respectively), to ensure only free RNA was removed and not any potentially disassociated coat proteins. The spin filtration did remove the RNA, however the full length RNA1 and RNA2 associated with CPMV are 5.8 and 3.4 kilobase in length respectively. These lengths of RNA would exhibit hydrodynamic radii in the range of 9-12 nm when free in solution, suggesting the full length RNA would not be removed using the 10 kDa MWCO filter which has an approximate pore size of 10 Å in radius. The successful removal of the RNA using the spin filters suggests that the RNA is released and degraded as a result of melt processing. RNA is sensitive to high temperatures and shear, which are applied during the melt processing, thus the degradation of RNA under these conditions was likely. An aggregate peak was also observed at the void volume, however it was not the majority of the eluted particles. The peak did also broaden towards higher elution volumes after melt processing, possibly indicating some lower order aggregates small enough to not elute in the void volume. The ratio of 260 to 280 nm absorbance is 1.8 for wild type CPMV and exhibits a maximum absorbance at 260 nm due to the contribution of the packaged RNA. After removal of the RNA, the empty CPMV particles exhibit a maximum absorbance at 280 nm and a 260 to 280 nm ratio of 0.9. The FPLC result of the recovered melt processed CPMV particles and the shift in 260 and 280 nm observed was consistent with the known spectroscopic properties of CPMV devoid of RNA. The DLS result matched well with the FPLC result, and yielded two peaks at 16.9 and 147.9 nm (FIG. 23B). The peak at 147.9 nm likely correlated to the aggregates eluting in the void volume, while the increase in the lower value average radius from 15.1 to 16.9 nm would correlate to the broadening seen in the FPLC result. TEM imaging further confirmed that the particles remain intact and in the correct shape after melt processing with the PLGA/PEG8000 blend.

Agarose gel electrophoresis was used to probe whether the melt processing or the organic extraction of the CPMV from the polymer causes the RNA to disassociate from CPMV. Three samples of 10% CPMV/PLGA/PEG8000 were incubated in 10 mM phosphate buffer, pH 7.4 at 37° C. and the released CPMV after 24 hours was collected, pooled, and concentrated. The organic extracted CPMV, released CPMV, and wild type CPMV were run on an agarose gel with 1 wt % ethidium bromide and imaged via UV for RNA visualization, and Coomassie staining for protein visualization (FIG. 24). The wild type CPMV exhibited the expected two bands or RNA that co-localized with the protein bands. CPMV recovered via organic extraction was representative of all of the CPMV present in the polymer and had strong signal from the RNA below the protein bands, indicating the RNA was disassociated from the virus particles. There was also some protein and RNA content that remained in the well, corresponding to aggregated species and also indicating that the aggregates retain RNA when they form. The CPMV released over 24 hours did not have any RNA signal, but did have the expected protein bands from intact particles. The absence of RNA from the aqueous release was likely due to the removal of RNA during centrifugal filtration and concentration. The result did indicate that the organic extraction process did not cause the disassociation of RNA from CPMV, since CPMV recovered via aqueous release did not have RNA associated with the particles. Overall, the results clearly indicated that CPMV could be melt processed at 80° C. with a blend of PLGA/PEG8000 and remain as intact viral nanoparticles, but with the loss of the packaged RNA.

CPMV/PLGA Microparticles

The cylindrical polymeric implants containing 10 wt % Qβ were directly implanted into the subcutaneous space of the mice for vaccination against the Qβ surface epitopes. The utilization of CPMV as an in situ vaccine requires the CPMV to be released directly into the intratumoral space, which may not be amenable to the implantation of a cylindrical or other geometry solid polymeric piece. Microparticles have been extensively used as injectable polymeric depots for sustained delivery applications, however as discussed in the background they are almost exclusively produced through solvent based emulsion methods. In order to maintain a solvent-less, high throughput production method oscillatory ball milling was utilized to mill the extruded CPMV/polymer cylinder into micron sized particles. The CPMV/polymer cylinders were kept at −80° C. for 2 hours and then milled in a Teflon grinding bowl, with liquid nitrogen added, for 15 minutes at 30 Hz. The pre-freezing and addition of liquid nitrogen during milling were necessary to maintain the rigidity of the material so it would be effectively ground, and to prevent heating due to kinetic energy, which results in the melting of the polymeric material during milling.

Micron sized particles of PLGA/15% PEG8000 containing 10 wt % CPMV were successfully manufactured through the cryo-milling process and exhibited mostly elliptical morphology with rough surface characteristic when analyzed via SEM (FIG. 25A). Analysis of the particles with ImageJ indicated that the particles predominately ranged from 10 to 20 μm in diameter (FIG. 25B), a size that has previously been used as injectable depots for drug delivery. The microparticle size was also analyzed via DLS after suspension in phosphate buffered saline and the suspended particles exhibited a similar size range to the size range determined via SEM (FIG. 25C). The bimodal characteristic of the DLS histogram is not reflected in the image analysis of the SEM image, and may be a consequence of microparticle settling during DLS measurement skewing the result. Fluorescently tagged PLGA was also incorporated with the CPMV/polymeric material in order to allow for the study of PLGA degradation once injected in vivo. PLGA was purchased coupled with an FPI749 near-infrared dye, useful in biological tissues as the excitation and emission of NIR dyes allow for good penetration of tissues and low auto-fluorescence background signal. PLGA-FPI749 was incorporated at 5 wt % with the CPMV/PLGA/PEG8000 blend via melt processing as previously described. The extruded material was then cryo-milled into microparticles and imaged via confocal microscopy (FIG. 25D). The microparticles were fluorescent under confocal imaging, indicating that the dye-labeled PLGA maintained fluorescence during the melt processing at 80° C. and can potentially be used to monitor in vivo PLGA degradation.

In order to ensure that CPMV did not denature or further aggregate during cryo-milling to create the microparticles, CPMV was recovered from the microparticles via release into phosphate buffered saline over 24 hours. Analysis of the recovered CPMV on an agarose gel indicated similar results to CPMV only subjected to melt processing (FIG. 26A). The CPMV from microparticles did not retain the RNA and was maintained as a viral nanoparticle. This was further confirmed via DLS analysis, and the CPMV did not exhibit increased aggregation after cryo-milling into microparticles relative to initial melt processing (FIG. 26B).

In Vitro CPMV Release

The in vitro release properties were studied to determine how CPMV would release from the polymeric matrix and the effect of material geometry (FIG. 27). Rod shaped samples produced via initial melt processing with the syringe extrusion device were compared to polymeric microparticles. Both samples were incubated with phosphate buffered saline (pH 7.4) at 37° C. to simulate in vivo conditions. The burst release from the initial hydration and swelling of the polymeric materials resulted in 10 and 5% cumulative protein release for rod and microparticle samples respectively. After the initial hydration, both samples followed relatively linear release profiles over a 40 day period. PLGA devices typically follow a biphasic release profile, with a lag period after initial hydration until bulk erosion begins. The addition of the PEG additive has previously mitigated the lag effect in PLGA samples with Qβ. The PEG8000 additive with the CPMV/PLGA samples resulted in increased porosity of the PLGA matrix after the initial hydration, due to the hydrophilic PEG diffusing out of the matrix. These pores would allow for more rapid diffusion of CPMV out of the matrix and the more rapid onset of bulk erosion during release. After 40 days, the total cumulative release of CPMV was ~40 and ~25% for the rod and microparticle samples respectively.

The lower total amount released for the microparticle samples was unexpected, as the increased surface area of the microparticles relative to the rod shaped samples should result in a higher total amount released. This discrepancy is likely due to how the different geometries respond to swelling at 37° C., above the glass transition temperature of PLGA. The rod geometry of the initial melt processed material remains as a rod once the swelling and softening of the material takes place during release and does not collapse into itself to form a circular geometry. In contrast, the microparticles settle to the bottom of the vessel containing the material and release medium. Once the swelling and softening of the material takes place, the particles coalesce into a single piece of polymeric material, limiting the available surface area directly in contact with the release medium. This difference between the rod shaped and microparticle samples results in the rod geometry having a larger surface area relative to the coalesced microparticle samples, thus likely being the reason for the rod shaped initial melt processed geometry having a larger total amount of protein released over time. This effect for microparticle samples during in vitro release studies has been studied previously, and the effects can be mitigated through vortexing to break-up the coalesced particles, sonication and sieving, and other methods to prevent the consolidation of particles into a single polymeric material with limited release surface area. All of these methods would potentially alter the release profile towards higher amounts released, however each skews the release kinetics through application of mechanical and mixing forces that can break-up polymer entanglements and alter the diffusion of proteins out of the polymeric matrix. These is no consistent method for determining completely accurate in vitro release profiles and in vivo application would exhibit different release profiles than in vitro due to the microparticles being injected into viscous tissue, a constant flux of water through the environment, and enzymatic activity on the polymer. Overall, the release profile allowed for a rough estimation of the release profile for in vivo application and demonstrates that, in both initial melt processed and microparticle formulations, CPMV could be successfully released and maintain particle integrity.

The CPMV was not completely released from the polymer matrix over the course of the in vitro release study for both rod shaped and microparticle CPMV/polymer samples. The maximum cumulative amount released was 42% and 27.3% for rod and microparticle samples respectively. These values are both lower than the release values seen with Qβ processed with 10% PEG8000, which was 72% at day 45. This discrepancy between released amounts was surprising, as an increase in PEG additive was expected to increase the release rate due to increased porosity as the PEG diffuses out. However, PEG also functions as a viscosity modifier when present in high concentrations in solution. Studies with PEG8000 have found that 10 and 20 wt % solutions of PEG8000 exhibit viscosities 9 and 20 times higher than water respectively. Furthermore, PEG8000 acts as a precipitating agent for many proteins and it has previously been shown that PEG polymers above 6000 Da at concentrations above 15 wt % in solution are highly effective at precipitating high molecular weight proteins. Thus, in the in vitro release environment the PEG may remain entrapped in the PLGA with the CPMV and increase the local viscosity within the channels formed in the polymer matrix during swelling and pore formation. This would retard the diffusion of both PEG and CPMV through the matrix into the external environment, diminishing the effectiveness of PEG as a porogen when used as at higher concentrations. The increased local concentration of dissolved PEG within water channels can also potentially result in the local precipitation of CPMV within PLGA, further slowing the release from the matrix. Local CPMV precipitates will solubilize as intact when the PEG concentration in the solution decreases, and PEG precipitation is a step in the purification of the virus from infected leaves. However, the diffusion of PEG from the polymer matrix will be controlled by the volume of the in vitro release buffer and sampling times. The release in the in vitro system is not wholly representative of in vivo release for reasons previously described, and the proposed issues with PEG diffusion and CPMV precipitation will likely be mitigated by constant release medium flux in vivo. The difference between in vitro and in vivo release and degradation of the polymer has previously been observed, where implanted Qβ/PLGA systems were completely degraded after 75 days and in vitro release systems of the same material still had unreleased Qβ and polymeric material present after the same time period. The microparticle systems for CPMV would have the same limitations due to the PEG additive as the rod samples, but the effect of high local PEG concentration would be enhanced due to the coalescence of the particles as previously described. This would further diminish the diffusion of PEG out of the polymer matrix and result in the low amount of release exhibited during the in vitro release study.

Microneedle Production

The composite CPMV/PLGA/PEG8000 material application was further expanded to microneedle arrays produced via melt processing. As previously described in Example 2, microneedles are an attractive platform for the non-invasive and painless administration of vaccines and Qβ was shown to be successfully incorporated into microneedle arrays. The application for Qβ was to generate humoral immunity against Qβ carrying an antigenic epitope on the surface. For CPMV, the application is in situ vaccination where the viral nanoparticle is directly applied to the tumor site. This limits the application of CPMV microneedle arrays to melanoma treatments, however melanoma is a common and serious cancer that can spread to other parts of the body and metastasize. Administration of CPMV for immunotherapy against melanoma via microneedle application has the potential to treat melanoma, and also protect against metastasis. Studies with CPMV have shown that in situ vaccination generated a humoral immune response against the cancer cells and protected against tumor growth when the animal model was re-challenged at a different site.

Microneedle arrays were successfully manufactured utilizing the same silicone molds that were previously utilized to create microneedles with Qβ. PLGA with 15 wt % PEG8000 and no CPMV was first utilized to make several microneedle arrays to ensure the incorporation of PEG did not adversely affect the mechanical properties of the needles. The needles were uniform and of the correct size via SEM after melt molding at 80° C. with 3 degassing cycles for 25 minutes total processing time (FIG. 28A). The mechanical properties were determined via compression testing and yielded values of 0.376±0.00835 N maximum strength per needle and 37.55±0.835 N maximum strength for the entire array (FIG. 28B). The maximum strength values were determined from 3 individual arrays, indicating that the melt molding process results is reproducible and consistent in the strength of the needles produced. These values have previously been shown to be sufficient for both in vivo and clinical models for skin puncture by the microneedles. This result demonstrated that the PLGA/PEG8000 blend can be successfully molded into microneedles and exhibit the necessary mechanical properties for application.

After validation of microneedle arrays production using PLGA/PEG8000, the melt processed CPMV/polymeric material was melt molded into microneedle arrays using the same conditions for PLGA/PEG8000 microneedle production. The arrays formed exhibited the same needle shape and size and the CPMV within the array was extracted via ethyl acetate as previously described. The recovered CPMV was analyzed for aggregation and particle integrity. The DLS histogram of the recovered particles indicated 51.2% of the particles remained as intact, single particles (FIG. 29A). The remaining particles appeared as two aggregated populations centered at 126.7 and 235.2 nm roughly correlating to aggregates of 8 and 15 particles respectively. Analysis of the particles with agarose gel electrophoresis further confirmed that the particles remained intact, but lost the viral RNA packaged with CPMV (FIG. 29B). The extracted particles were also analyzed via TEM, and the images did have intact particles present (FIG. 29C). However, there was also strong signal from polymer still present in the sample obscuring some of the particles. This indicated that the extraction of the particles from the microneedle polymeric array was did not successfully remove all of the polymer. The mass of polymer composite used, volume of ethyl acetate used, and overall process were the same as previous extraction methods that successfully separated protein from the polymer matrix. This incomplete extraction may be due to the different geometry of the microneedle array, square as opposed to the typical rod geometry, hindering effective solubilization of all of the polymer in the sample. The presence of free PLGA in solution may have also skewed the DLS result, as free PLGA could potentially interact with multiple viruses through ionic or hydrogen bonding interactions, causing them to aggregate in solution. Nonetheless, the results indicated that further melt molding into microneedle arrays kept the majority of CPMV intact and have potential application for dermal administration of CPMV as an in situ vaccination agent for melanoma and other skin cancers.

Figure 30:
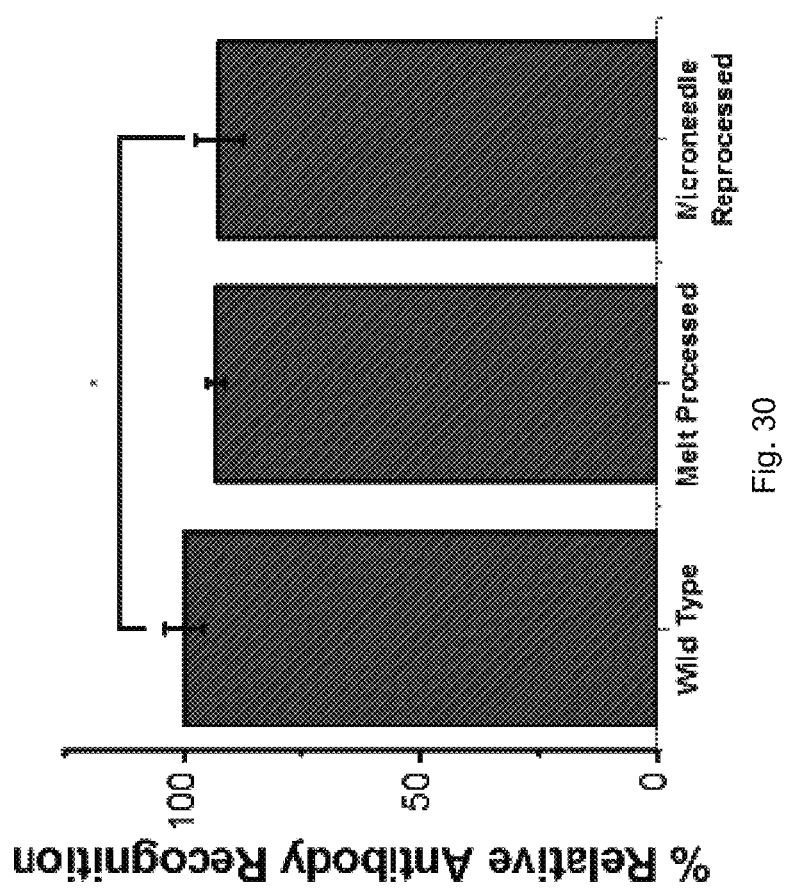
FIG. 30 illustrates ELISA response from wild type, melt processed, and microneedle reprocessed CPMV. The absorbance at 405 nm, indicative of the antibody binding to CPMV, was normalized to the wild type CPMV value to yield a percent antibody recognition. The results are reported as the average and standard deviation (n=3). * $p<0.05$ determined via a two tailed t-test with equal variance assumed.

The previous work described herein has demonstrated that CPMV can be melt processed and retain structural integrity with minimal to moderate aggregation depending on the time of the melt processing. However, all of the analytical techniques utilized were only able to evaluate the structural integrity, size, and association between the coat protein assembly and viral RNA of the CPMV. ELISA was utilized to determine how the biochemical signature of CPMV was maintained after melt processing with the PLGA/PEG8000 blend. The maintenance of the biochemical patterns on the surface of CPMV is essential for the successful application as an in situ vaccine, as the PAMPs on the surface are necessary to elicit a strong anti-tumoral response. The ELISA study utilized a polyclonal antibody purified from rabbit specifically against CPMV that specifically recognize the pattern of the coat protein assembly on the viral surface. ELISA plates were coated with wild type CPMV, CPMV extracted from rod samples that were melt processed with the syringe extruder, and CPMV extracted from the further melt processed microneedle array. The CPMV from the melt processed samples was extracted via ethyl acetate to represent all of the CPMV present in the sample. The melt processed viruses were also spin filtered to remove all free RNA after extracting to ensure the ELISA response would only be due to the coat protein assemble of CPMV. The results of the ELISA analysis were normalized to the response from wild type CPMV (FIG. 30). CPMV subjected to the initial melt processing exhibited an antibody recognition of 93.2±2.1% of the wild type CPMV recognition. Analysis via a two tailed t-test against wild type CPMV indicated that there was no statistical difference between the ELISA response of wild type and melt processed CPMV. Therefore, within error, the melt processing via syringe extrusion had no effect on the biochemical signature of CPMV. Further melt processing to create microneedle arrays yielded CPMV with an antibody recognition of 92.4±5.3% relative to the wild type. Statistical analysis of the microneedle processed CPMV against wild type CPMV yielded a p value less than 0.05, indicating that there was statistical difference between the samples. The lowered recognition due to melt processing could potentially be due to some denaturation of the particle or decreased surface for antibody binding due to aggregation jamming particles together. However, the diminishment in antibody recognition of the microneedle sample was only 7.6% indicating that the majority of particles retain the biochemical character of CPMV after extensive melt processing.

Ovarian Cancer Treatment with CPMV/PLGA/PEG8000 Microparticles

CPMV has previously been shown to effectively treat an ID8-Defb29/Vegf-A aggressive ovarian cancer (OVCA) model in a mice when administered in weekly doses. We sought to utilize CPMV formulated into the polymer blend via melt processing and milling into microparticles as a single administration depot to replace the multiple injections of CPMV necessary for treatment. As the melt processed formulation has been shown to maintain the structural and biochemical properties of wild type CPMV and the ability to be released, we hypothesized that a single injection of microparticles into the intraperitoneal space of the mice can successfully release CPMV and elicit an anti-tumoral response. Mice were inoculated via intraperitoneal injection with the aggressive ovarian cancer ID8-Defb29/Vegf-A cells transformed to express luciferase as a reporter for tumor growth. Treatment began 7 days after tumor cell inoculation with 12 mg of CPMV microparticles suspended in 1 mL of PBS and injected into the intraperitoneal space of each treated mouse. This amount of microparticles was chosen to release 300 µg over 20 days based on the in vitro release study and would correlate to 3 weekly injections of CPMV in 100 µg doses. The control group were injected with the same amount of PLGA/PEG8000 microparticles without CPMV present. Three other treatment groups were injected 4 times on a weekly basis with 30, 100, or 500 µg of CPMV in solution (FIG. 31A).

Figure 32:
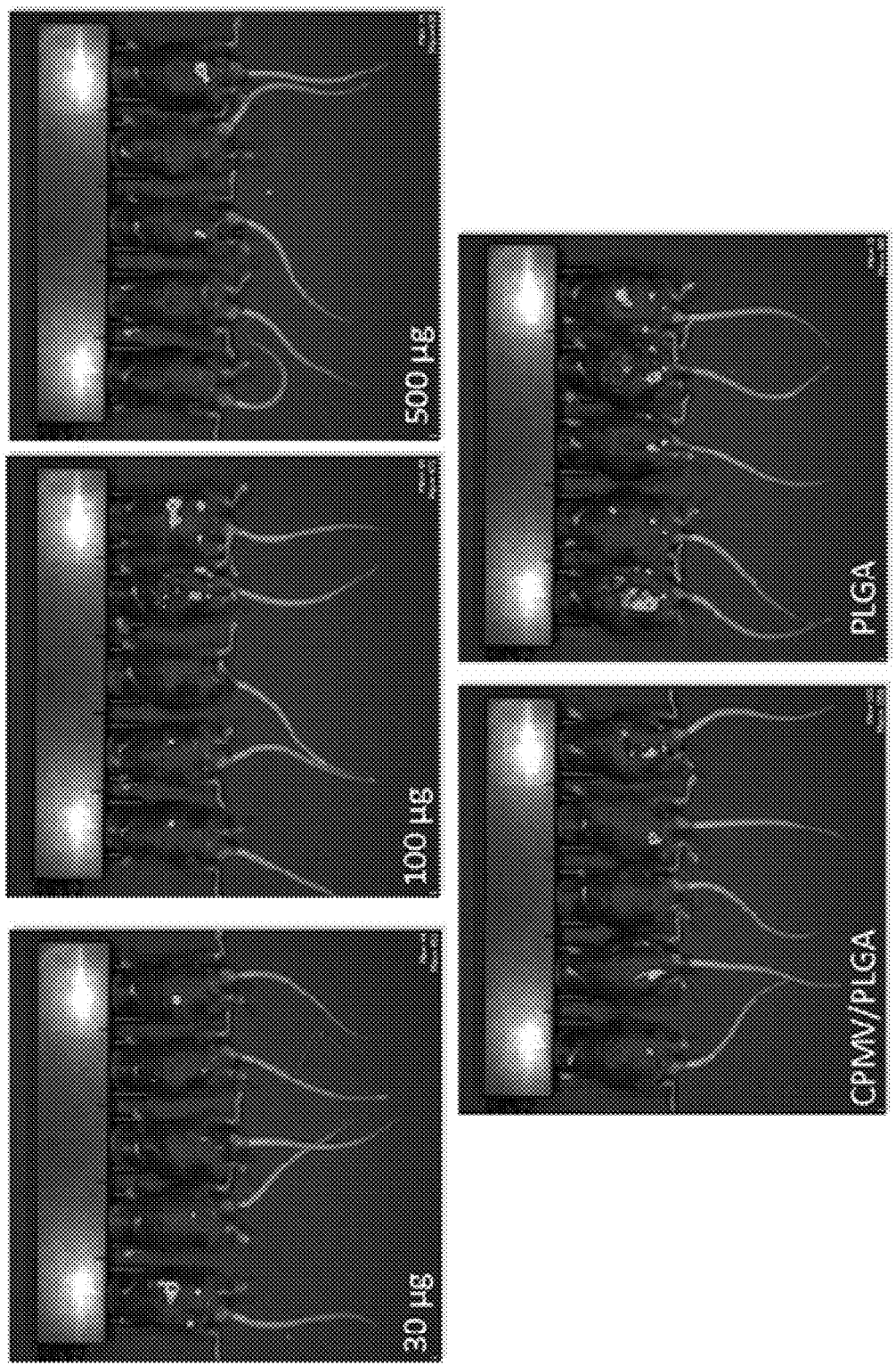
FIG. 32 illustrates images of luminescence from the luciferase reporter in the ID8-Debf29/Vegf-A ovarian cancer cells for treatment groups on day 57.

Tumor growth was monitored on a biweekly basis by measuring the luminescence from the luciferase reporter in the OVCA cells, the circumference of the mouse abdomen, and the weight (FIGS. 31B-C). The luminescence result both indicated that the single administration of PLGA/PEG8000 microparticles loaded with CPMV had a moderate effect in preventing tumor growth, with the luminescence value of mice treated with the microparticles having roughly 50% the luminescence of the control group at day 57. The mice treated with multiple injections of CPMV at all dosages exhibited higher suppression of tumor growth relative to the microparticle and control group, exhibited total luminescence values 75% lower than the control group. The abdominal circumference measurement was also indicative of OVCA tumor growth due to the fluid retention and swelling in response to the spread of OVCA. Circumference measurements yielded similar results to the luminescence measurements, with CPMV loaded microparticle treated mice having an increase in circumference lower than the control group but higher than the mice treated via repeat injection. The weight measurements also had a lower average weight for the CPMV microparticle treatment group and the control group, while the CPMV injection treated group was consistently lower than both groups. Luminescence images of the treatment groups on day 57 (FIG. 32) clearly showed the CPMV microparticle group had lower tumor growth than the control group.

Figure 33:
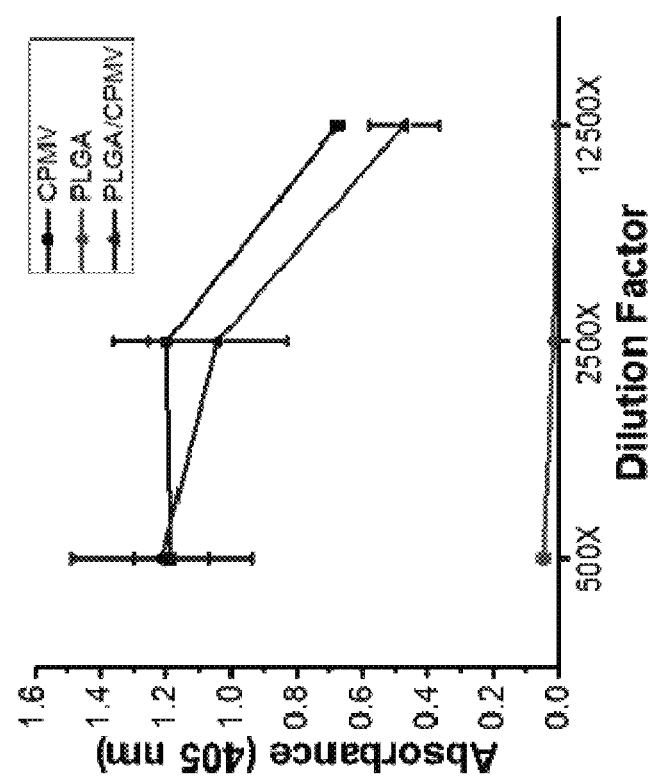
FIG. 33 illustrates ELISA results for anti-CPMV IgG from sera collected on day 46 for mice treated with 4 weekly injections of 100 μg CPMV (CPMV), mice treated with a single injection of PLGA/PEG8000 microparticles (PLGA), and mice treated with a single injection of CPMV loaded PLGA/PEG8000 microparticles (PLGA/CPMV). Three dilution factors of 500, 2500, and 12500 times dilution were used for the assay. The results are reported as the average and standard deviation of 2 mice for each treatment group.

Effective stimulation of the immune system against CPMV is essential for the simultaneous generation of an immune response against the OVCA tumor antigens for anti-tumoral activity. We had previously shown that the CPMV subjected to melt processed retained recognition by anti-CPMV IgG and sought to demonstrate that treatment with the CPMV loaded microparticles generated similar levels of anti-CPMV IgG as the mice treated with repeated injections of a CPMV solution. Mice that were treated with the PLGA/PEG8000 microparticles, the CPMV loaded microparticles, and repeated 100 µg injections had sera collected via retro-orbital bleeds on day 46 from 2 mice for each group to determine the anti-CPMV IgG levels. The sera was assayed via ELISA against wild type CPMV for 3 different dilution levels to ensure signal saturation was not occurring from the ELISA result (FIG. 33). The mice treated with 100 µg CPMV and the CPMV microparticles exhibited similar levels of anti-CPMV IgG for all dilutions, while the control microparticle mice had no response as expected. This result demonstrated that the CPMV microparticles release intact CPMV in vivo and elicit a similar immune response as repeated injections of CPMV, validating that the CPMV polymeric devices can release CPMV over an extended period of time in vivo and serve as a single administration vaccine.

Ovarian Cancer Treatment with CPMV/PLGA/PEG8000 Microparticles Co-Administered With Soluble CPGMV The results in the in vivo OVCA treatment example demonstrated that the CPMV microparticles suppressed tumor growth in an aggressive ovarian cancer model relative to untreated group. However, the CPMV particles were not as efficacious as repeated administration of CPMV solution. In the present example, we sought to overcome these effects by the co-administration of CPMV in solution alongside the microparticles to provide an initial immune response before sustained CPMV release. Mice were inoculated via intraperitoneal injection with the aggressive ovarian cancer ID8-Defb29/Vegf-A cells transformed to express luciferase as a reporter for tumor growth. Treatment began 7 days after tumor cell inoculation with CPMV microparticles suspended and soluble CPMV in PBS and injected into the intraperitoneal space of each treated mouse. The control group was injected with the same amount of PLGA/PEG8000 microparticles without CPMV present and with CPMV in solution.

Figure 34:
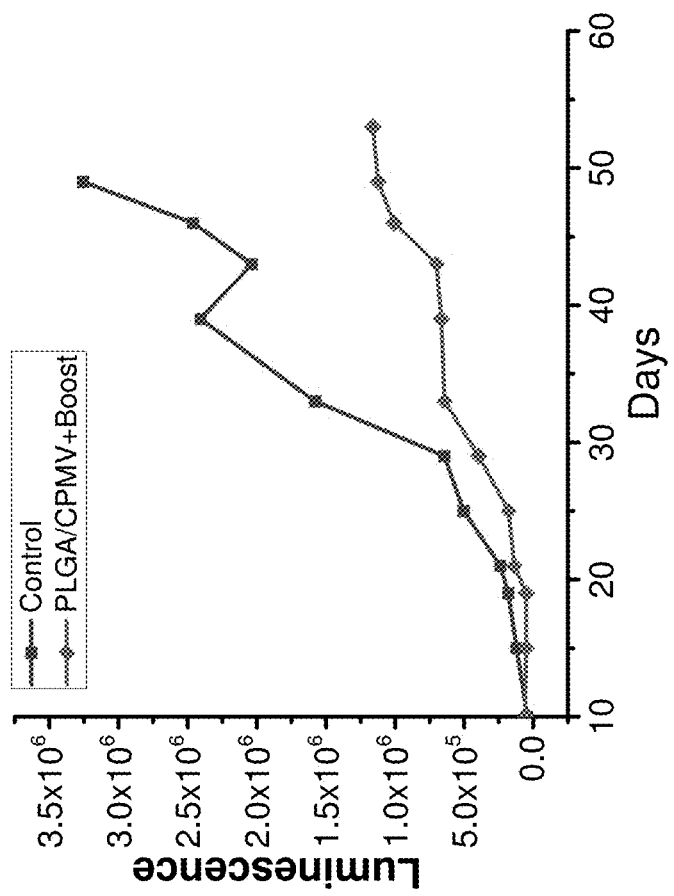
FIG. 34 illustrates a plot showing total luminescence from the luciferase reporter gene in the ID8-Debf29/Vegf-A ovarian cancer cells of mice injected with single dosage of either PLGA/PEG8000 microparticles or CPMV/PLGA/PEG8000 microparticles coadministered with soluble CPMV boost.

Tumor growth was monitored on a biweekly basis by measuring the luminescence from the luciferase reporter in the OVCA cells (FIG. 34). The luminescence result indicated that the single administration of PLGA/PEG8000 microparticles loaded with CPMV and with CPMV in solution exhibited enhanced suppression of tumor growth, with exhibited total luminescence values 75% lower than the control group at day 57.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A melt processed degradable viral nanoparticle construct for delivery of virus or virus-like particles to a site of interest, the nanoparticle construct comprising:
   a degradable polymer matrix, and
   a plurality of virus or virus-like particles encapsulated within the degradable polymer matrix, the nanoparticle construct upon administration to the site of interest providing a sustained release of the virus or virus-like particles upon degradation of the polymer matrix, the virus or virus-like particles upon release from the degradable polymer matrix having the same or substantially similar structural and/or biochemical characteristics as the virus or virus-like particles prior to melt processing.

2. The nanoparticle construct of claim 1, wherein the degradable polymer matrix comprises a melt processable degradable polymer material that is biocompatible and, upon degradation, produces substantially non-toxic products.

3. The nanoparticle construct of claim 2, wherein the site of interest is a cell or tissue of a subject.

4. The nanoparticle construct of claim 2, wherein the site of interest is a plant propagation material, a plant, part of a plant and/or plant organ.

5. The nanoparticle construct of claim 2, wherein the melt processable degradable polymer material is a melt processable biodegradable polymer.

6. The nanoparticle construct of claim 3, the virus or virus-like particles having a release profile from the degradable polymer matrix at least partially defined by the degradation of the degradable polymer material under physiological conditions.

7. The nanoparticle construct of claim 2, wherein the melt processing of degradable polymer material and the virus or virus-like particles is at a Peclet number of about 5 to about 25, wherein the Peclet number is determined by the following equation:

$$Pe = \frac{6\pi\eta\dot{\gamma}R^3}{k_b T}$$

where: $\eta$=viscosity of the polymer melt (Pa·s)
$\dot{\gamma}$=shear rate applied to the system ($s^{-1}$)
R=weight average radius of the particles before shear application (m)
$k_b$=Boltzmann's constant ($J \cdot K^{-1}$)
T=temperature of the system (K).

8. The nanoparticle construct of claim 1, wherein the virus or virus-like particles are substantially uniformly dispersed in the degradable polymer matrix.

9. The nanoparticle construct 2, wherein the degradable polymer material has melt temperature below the degradation temperature of the virus or virus-like particles.

10. The nanoparticle construct of claim 2, wherein the degradable polymer material comprises poly(lactic-co-glycolic acid) (PLGA) or a copolymer thereof.

11. The nanoparticle construct of claim 1, further comprising at least one porogen.

12. The nanoparticle construct of claim 1, wherein the virus or virus-like particle is a bacteriophage or plant virus or virus like-particle.

13. The nanoparticle construct of claim 1, wherein the virus or virus-like particle is a plant picornavirus or a filamentous plant virus or virus-like particle.

14. The nanoparticle construct of claim 12, wherein the plant virus or virus-like particle is a Qβ bacteriophage or virus-like particle, a cowpea mosaic virus-like particle or potato virus X virus-like particle.

15. The nanoparticle construct of claim 12, wherein the plant virus particle or virus-like particle is a rod-shaped virus particle.

16. The nanoparticle construct of claim 1, wherein the virus or virus-like particle is loaded with or bonded to a cargo molecule.

17. The nanoparticle construct of claim 16, wherein the cargo molecule comprises at least one of a therapeutic agent, detectable moiety, or targeting agent.

18. The nanoparticle construct of claim 17, the therapeutic agent comprising an anticancer agent.

19. The nanoparticle construct of claim 1, providing in situ delivery of the virus or virus-like particles upon administration to a subject.

20. The nanoparticle construct of claim 1, being provided in the shape of a plurality of microparticles or microneedles.

* * * * *

SEQUENCE LISTING

```
Sequence total quantity: 5
SEQ ID NO: 1           moltype = AA  length = 28
FEATURE                Location/Qualifiers
REGION                 1..28
                       note = Synthetic Construct
```

```
source                  1..28
                        mol_type = protein
                        organism = synthetic construct
SEQUENCE: 1
GGSGSGGPES FDGDPASNTA PLQPEQLQ                                          28

SEQ ID NO: 2            moltype = AA  length = 26
FEATURE                 Location/Qualifiers
REGION                  1..26
                        note = Synthetic Construct
source                  1..26
                        mol_type = protein
                        organism = synthetic construct
SEQUENCE: 2
GGSGSGGYQD MVLWKDVFRK NNQLAP                                            26

SEQ ID NO: 3            moltype = DNA  length = 474
FEATURE                 Location/Qualifiers
misc_feature            1..474
                        note = Synthetic Construct
source                  1..474
                        mol_type = other DNA
                        organism = synthetic construct
SEQUENCE: 3
gatataccat ggcaaaatta gagactgtta ctttaggtaa catcgggaaa gatggaaaac        60
aaactctggt cctcaatccg cgtggggtaa atcccactaa cggcgttgcc tcgctttcac       120
aagcgggtgc agttcctgcg ctggagaagc gtgttaccgt ttcggtatct cagccttctc       180
gcaatcgtaa gaactacaag gtccaggtta agatccagaa cccgaccgct tgcactgcaa       240
acggttcttg tgacccatcc gttactcgcc aggcatatgc tgacgtgacc ttttcgttca       300
cgcagtatag taccgatgag gaacgagctt ttgttcgtac agagcttgct gctctgctcg       360
ctagtcctct gctgatcgat gctattgatc agctgaaccc agcgtatctg gtggtccgga       420
atctttcgac ggtgacccgg cttctaacac cgctccgctg cagccggaac agct             474

SEQ ID NO: 4            moltype = DNA  length = 32
FEATURE                 Location/Qualifiers
misc_feature            1..32
                        note = Synthetic Construct
source                  1..32
                        mol_type = other DNA
                        organism = synthetic construct
SEQUENCE: 4
gcagtaataa ggatgactcg agtctggctg ca                                     32

SEQ ID NO: 5            moltype = DNA  length = 513
FEATURE                 Location/Qualifiers
misc_feature            1..513
                        note = Synthetic Construct
source                  1..513
                        mol_type = other DNA
                        organism = synthetic construct
SEQUENCE: 5
gatataccat ggcaaaatta gagactgtta ctttaggtaa catcgggaaa gatggaaaac        60
aaactctggt cctcaatccg cgtggggtaa atcccactaa cggcgttgcc tcgctttcac       120
aagcgggtgc agttcctgcg ctggagaagc gtgttaccgt ttcggtatct cagccttctc       180
gcaatcgtaa gaactacaag gtccaggtta agatccagaa cccgaccgct tgcactgcaa       240
acggttcttg tgacccatcc gttactcgcc aggcatatgc tgacgtgacc ttttcgttca       300
cgcagtatag taccgatgag gaacgagctt ttgttcgtac agagcttgct gctctgctcg       360
ctagtcctct gctgatcgat gctattgatc agctgaaccc agcgtatggt ggttctggtt       420
ctggtggtta ccaggacatg gttctgtgga aagacgtttt ccgtaaaaac aaccagctgg       480
ctccgtaata aggatgactc gagtctggct gca                                    513
```